US008268635B2

(12) United States Patent
Ferrante et al.

(10) Patent No.: US 8,268,635 B2
(45) Date of Patent: Sep. 18, 2012

(54) METHODS OF IDENTIFYING AGENTS THAT SELECTIVELY ACTIVATE P38 AND/OR NKKB SIGNALING

(76) Inventors: Antonio Ferrante, North Adelaide (AU); Charles S. T. Hii, Marino (AU)

( * ) Notice: Subject to any disclaimer, the term of this patent is extended or adjusted under 35 U.S.C. 154(b) by 0 days.

(21) Appl. No.: 12/301,429

(22) PCT Filed: May 18, 2007

(86) PCT No.: PCT/AU2007/000690
§ 371 (c)(1),
(2), (4) Date: Jun. 19, 2009

(87) PCT Pub. No.: WO2007/134384
PCT Pub. Date: Nov. 29, 2007

(65) Prior Publication Data
US 2009/0291899 A1 Nov. 26, 2009

(30) Foreign Application Priority Data

May 19, 2006 (AU) .................... 2006902704
Nov. 1, 2006 (AU) .................... 2006906064

(51) Int. Cl.
G01N 33/566 (2006.01)
G01N 33/53 (2006.01)
G01N 33/567 (2006.01)
(52) U.S. Cl. .................. 436/501; 435/7.1; 435/7.2
(58) Field of Classification Search .................. None
See application file for complete search history.

(56) References Cited

U.S. PATENT DOCUMENTS

| 5,587,457 | A | * | 12/1996 | Rathjen et al. | ........... 530/326 |
| 5,665,859 | A | | 9/1997 | Wallach et al. | |
| 5,965,439 | A | * | 10/1999 | Tenner et al. | ........... 435/455 |
| 7,410,634 | B2 | | 8/2008 | Gupte et al. | ........... 424/9.3 |
| 2004/0254446 | A1 | | 12/2004 | Miller et al. | ........... 600/410 |
| 2006/0218010 | A1 | * | 9/2006 | Michon et al. | ........... 705/3 |
| 2010/0069297 | A1 | * | 3/2010 | Fenton et al. | ........... 514/12 |

OTHER PUBLICATIONS

Bulgin D, et al. Thyroid. 16(3):217-24, Mar. 2006.*
Lee JC, et al. Pharmacol. Ther. 82(2-3):389-397, 1999.*
Enslen H, et al. J. Biol. Chem. 273:1741-8, 1998.*
Enslen H, et al. EMBO J. 19(6):1301-1311, 2000.*
Geng Y, et al. J. Clin. Invest. 98(10):2425-2430, 1996.*
Michael D. Noseworthy, Daniel P. Bulte, and Jeff Alfonsi, *Bold Magnetic Resonance Imaging of Skeletal Muscle*, Seminars in Musculoskeletal Radiology, Thieme Medical Publishers, New York, N.Y., vol. 7, No. 4, 2003, pp. 307-315. Abstract; p. 307, paragraph 1-p. 309, col. 1, paragraph 3; p. 311, col. 2, paragraph 3-p. 312, col. 2, paragraph 4.
Matthias Weigel, *Dynamische NMR-Messungen zur Gehirnfunktion bei variablem Sauerstoffangebot*, Thesis, Wurzburg, Germany, Dec. 2000. pp. 1-2; pp. 28-31; pp. 63-82.
Christoph Losert, Michael Peller, Phillipp Schneider, and Maximilian Reiser, *Oxygen-Enhanced MRI of the Brain*, Magnetic Resonance in Medicine, vol. 48, pp. 271-277 (2002).
Hii et al., "Stimulation of p38 Phosphorylation and Activity by Arachidonic Acid in HeLa Cells, HL60 Promyelocytic Leukemic Cells, and Human Neutrophils." Journal of Biological Chemistry (1998) vol. 273, No. 30, pp. 19277-19282.
Briscoe et al., "A novel tumor necrosis factor (TNF) mimetic peptide prevents recrudescence of *Mycobacterium bovis* bacillus Calmette-Guerin (BCG) infection in CD4+ T cell-depleted mice." Journal of Leukocyte Biology (2000) vol. 68, pp. 538-544.
Tucker et al., "Switching Leukemia Cell Phenotype Between Life and Death." PNAS (2004) vol. 101(35) pp. 12940-12945.
Murali et al., "Disabling TNF Receptor signaling by Induced Conformational Perturbation of Tryptophan-107." PNAS (2005) vol. 102(31) pp. 10970-10975.
International Search Report for International Application No. PCT/AU2007/000690.
Fournel et al., "$C_3$-symmetric peptide scaffolds are functional mimetics of trimeric CD40L", Nature Chemical Biology, vol. 1, No. 7, Dec. 2005, 377-382.
Kumaratilake et al., "A Synthetic Tumor Necrosis Factor-α Agonist Peptide Enhances Human Polymorphonuclear Leukocyte-mediated Killing of *Plasmodium falciparum* in Vitro and Suppresses *Plasmodium chabaudi* Infection in Mice", Journal of Clinical Investigation, vol. 95, May 1995, 2315-2323.
Rathjen et al., "Differential effects of small tumour necrosis factor-α peptides on tumour cell cytotoxicity, neutrophil activation and endothelial cell procoagulant activity", Immunology 1993, 80, 293-299.
Smith et al., "Novel Ketal ligands for the glucocorticoid receptor: in vitro and in vivo activity", Bioorganic & Medicinal Chemistry Letters 15 (2005) 2926-2931.
European Search Report, Application No. 07718936.3, dated: Aug. 19, 2010.

* cited by examiner

*Primary Examiner* — Robert Landsman
(74) *Attorney, Agent, or Firm* — Heslin Rothenberg Farley & Mesiti P.C.

(57) ABSTRACT

The present invention relates to a method of selectively modulating a signalling pathway of interest controlled by a cell receptor involved in signalling through multiple pathways. The method includes exposing the receptor to an agent that modulates signalling by the receptor through the signalling pathway of interest and does not substantially modulate signalling through one or more other signalling pathways controlled by the receptor.

3 Claims, 22 Drawing Sheets

SEQUENCE LISTING

```
<160> NUMBER OF SEQ ID NOS: 12

<210> SEQ ID NO 1
<211> LENGTH: 455
<212> TYPE: PRT
<213> ORGANISM: Homo sapiens

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
```

```
              50                  55                  60
Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
450                 455

<210> SEQ ID NO 2
<211> LENGTH: 461
```

<212> TYPE: PRT
<213> ORGANISM: Homo sapiens

<400> SEQUENCE: 2

```
Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400
```

```
Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Gly Thr Leu Leu Gly Ser Thr Glu Glu Lys Pro
        435                 440                 445

Leu Pro Leu Gly Val Pro Asp Ala Gly Met Lys Pro Ser
    450                 455                 460

<210> SEQ ID NO 3
<211> LENGTH: 11
<212> TYPE: PRT
<213> ORGANISM: Homo sapiens

<400> SEQUENCE: 3

Pro Ser Thr His Val Leu Leu Thr His Thr Ile
1               5                   10

<210> SEQ ID NO 4
<211> LENGTH: 11
<212> TYPE: PRT
<213> ORGANISM: Homo sapiens

<400> SEQUENCE: 4

Pro Ser Thr His Val Leu Ile Thr His Thr Ile
1               5                   10

<210> SEQ ID NO 5
<211> LENGTH: 19
<212> TYPE: PRT
<213> ORGANISM: Homo sapiens

<400> SEQUENCE: 5

Leu Ser Ala Glu Ile Asn Arg Pro Asp Tyr Leu Asp Phe Ala Glu Ser
1               5                   10                  15

Gly Gln Val

<210> SEQ ID NO 6
<211> LENGTH: 3
<212> TYPE: PRT
<213> ORGANISM: Homo sapiens

<400> SEQUENCE: 6

Gly Thr Thr
1

<210> SEQ ID NO 7
<211> LENGTH: 6
<212> TYPE: PRT
<213> ORGANISM: Homo sapiens

<400> SEQUENCE: 7

Leu Lys Pro Gly Thr Thr
1               5

<210> SEQ ID NO 8
<211> LENGTH: 12
<212> TYPE: PRT
<213> ORGANISM: Homo sapiens

<400> SEQUENCE: 8

His His His His His His Leu Lys Pro Gly Thr Thr
1               5                   10
```

```
<210> SEQ ID NO 9
<211> LENGTH: 9
<212> TYPE: PRT
<213> ORGANISM: Homo sapiens

<400> SEQUENCE: 9

Gly Thr Glu Asp Ser Gly Thr Thr Val
1               5

<210> SEQ ID NO 10
<211> LENGTH: 6
<212> TYPE: PRT
<213> ORGANISM: Homo sapiens

<400> SEQUENCE: 10

Glu Asp Ser Gly Thr Thr
1               5

<210> SEQ ID NO 11
<211> LENGTH: 157
<212> TYPE: PRT
<213> ORGANISM: Homo sapiens

<400> SEQUENCE: 11

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 12
<211> LENGTH: 9
<212> TYPE: PRT
<213> ORGANISM: Artificial
<220> FEATURE:
<223> OTHER INFORMATION: control peptide

<400> SEQUENCE: 12

Gly Gly Asp Pro Gly Ile Val Thr His
1               5
```

US 8,268,635 B2

METHODS OF IDENTIFYING AGENTS THAT SELECTIVELY ACTIVATE P38 AND/OR NKKB SIGNALING

CROSS REFERENCE TO RELATED APPLICATIONS

This application is a national phase filing under 35 U.S.C. §371 of PCT International Application PCT/AU2007/000690, filed May 18, 2007, and published under PCT Article 21(2) in English as WO 2007/134384 A2 on Nov. 29, 2007. PCT/AU2007/000690 claimed priority from Australian application Nos. 2006902704 filed on May 19, 2006 and 2006906064 filed on Nov. 1, 2006. The entire contents of each of the prior applications are incorporated herein by reference.

REFERENCE TO A SEQUENCE LISTING

This application contains a sequence listing, provided as a paper copy, as required under 37 C.F.R. §1.821(c), and is herein incorporated by reference in its entirety, as required under 37 C.F.R. §1.52(e)(5). A copy of the sequence listing is also provided under 37 C.F.R. §1.821(e), as a computer readable form.

FIELD OF THE INVENTION

The present invention relates to a method of selectively modulating signalling through a cell receptor.

BACKGROUND OF THE INVENTION

Receptors play a fundament role in both normal biological and pathological processes. Receptors generally bind a molecule and transduce the original signal produced upon binding of the molecule into a biological response by way of a cascade of intracellular signalling molecules.

In many cases, the binding of a molecule to a receptor modulates the activity of a number of intracellular signalling pathways, each of which may result in a specific biological response. For example, binding of the TNF-α to TNF Receptor-1 (TNFR1) activates multiple intracellular signalling pathways, including the p38, JNK and ERK1/2 signalling pathways.

In this regard, activation of p38 signalling by TNF receptor-1 upon binding of TNF-α is associated with an anti-inflammatory response and killing of tumour cells. Activation of the JNK and ERK1/2 pathways upon binding of TNF-α is important, for example, for cell regeneration. However, activation of the JNK and/or ERK1/2 signalling pathways is also associated with pathogenetic responses. This example underscores the fact that in many circumstances the modulation of multiple signalling pathways produces both beneficial and unwanted biological responses.

Given that receptors and their intracellular signalling pathways play a fundamental in both the biology of normal and pathological processes, receptor activity and intracellular signalling are potential targets for therapeutic intervention. However, a deficiency with many drugs that modulate receptor activity and/or the activity of their intracellular signalling pathways is that the drugs do not have the capacity to selectively target one or more intracellular signalling pathways, and as such promiscuously modulate other signalling pathways.

Accordingly, there is a need for new therapeutic agents and new therapeutic strategies that have the capacity to selectively target specific intracellular signalling pathways. The present invention relates to a method of selectively modulating signalling through a receptor that is involved in signalling through multiple intracellular signalling pathways.

A reference herein to a patent document or other matter which is given as prior art is not to be taken as an admission that that document or matter was known or that the information it contains was part of the common general knowledge as at the priority date of any of the claims.

SUMMARY OF THE INVENTION

The present invention arises out of the studies into signalling by TNF receptors. In particular, it has been found that it is possible to selectively modulate receptor signaling using mimetic peptides of the ligands for the receptor. The ability to selectively modulate signalling indicates that it possible to selectively modulate biological responses controlled by receptors generally, and the ability to screen for agents that can modulate signalling by receptors.

In addition, the site on the TNF receptor responsible for modulating signalling through a specific signalling pathway, the p38 signalling pathway, has been identified. This finding indicates generally that the selective modulation of signalling is associated with specific regions on a receptor.

It has also been found that mimetics of such regions of the receptor act as modulators of signalling. For example, in the case of the TNF Receptor, peptide mimetics of this region act as antagonists of TNF-α induced p38 signalling.

The present invention provides a method of selectively modulating a signalling pathway of interest controlled by a cell receptor involved in signalling through multiple signalling pathways, the method including exposing the receptor to an agent that modulates signalling by the receptor through the signalling pathway of interest and does not substantially modulate signalling through one or more other signalling pathways controlled by the receptor.

The present invention also provides a method of selectively modulating p38 signalling by TNFR1 or TNFR2 without substantially modulating one or more of JNK, ERK1/2 and PI3K signalling by the receptor, the method including exposing the receptor to an agent that modulates p38 signalling and does not substantially modulate signalling through one or more of the JNK, ERK1/2 and PI3K signalling pathways controlled by the receptor.

The present invention also provides a method of selectively modulating one or more of JNK, ERK1/2 and PI3K signalling by TNFR1 or TNFR2 without substantially modulating p38 signalling by the receptor, the method including exposing the receptor to an agent that modulates one or more of JNK, ERK1/2 and PI3K signalling and does not substantially modulate signalling through the p38 signalling pathway controlled by the receptor.

The present invention also provides a method of modulating one or more of JNK, ERK1/2 and PI3K signalling upon binding of TNF-α to TNFR1 and/or TNFR2 on a cell, the method including exposing the cell to an agent that alters the activity of TNF-α to modulate one or more of JNK, ERK1/2 and PI3K signalling upon binding of TNF-α to the receptor.

The present invention also provides a method of modulating p38 and/or NFκB signalling upon binding of TNF-α to TNFR1 and/or TNFR2 on a cell, the method including exposing the cell to an agent that alters the activity of TNF-α to modulate p38 and/or NFκB signalling upon binding of TNF-α to the receptor.

The present invention also provides a method of preventing and/or treating a p38-mediated disease, condition or state in a subject, the method including administering to the subject an agent that selectively modulates p38 signalling pathway in the subject and does not substantially modulate one or more of the JNK, ERK1/2 and PI3K signalling pathways in the subject.

The present invention also provides a method of identifying an agent that selectively modulates signalling through one or more signalling pathways controlled by a cell receptor, the method including identifying an agent that modulates signalling by the receptor through one or more signalling pathways without substantially modulating signalling by the receptor through one or more other signalling pathways.

The present invention also provides a method of identifying an agent that modulates p38 signalling by a TNF receptor, the method including:

identifying an agent that interacts with a region of TNFR1 that includes one or more of amino acids 209 to 211 of SEQ ID NO.1 and/or identifying an agent that interacts with a region of TNFR2 that includes one or more of amino acids 253 to 255 of SEQ ID NO.2;

determining the ability of the agent so identified to modulate p38 signalling by a TNF receptor; and identifying the agent as an agent that modulates p38 signalling by the TNF receptor.

The present invention also provides a method of identifying an agent that modulates signalling by a cell receptor, the method including:

identifying an agent that interacts with a region of the receptor that is involved in selective modulation of signalling by the receptor; and/or identifying an agent that modulates interaction of a molecule with a region of the receptor that is involved in selective modulation of signalling by the receptor;

determining the ability of the agent to modulate signalling by the receptor; and identifying the agent as an agent that modulates signalling by the receptor.

The present invention also provides a method of identifying an agent that modulates one or more of p38, JNK and ERK1/2 signalling by a TNF receptor, the method including:

identifying an agent that interacts with a region of TNFR1 that includes one or more of amino acids 209 to 211 of SEQ ID NO.1; and/or identifying an agent that interacts with a region of TNFR2 that includes one or more of amino acids 253 to 255; and/or identifying an agent that modulates interaction of a molecule that includes an amino acid sequence of SEQ ID NO.3, or a variant thereof, with the TNF receptor; and/or identifying an agent that modulates interaction of a molecule that includes an amino acid sequence of SEQ ID NO.4, or a variant thereof, with the TNF receptor; and/or identifying an agent that modulates interaction of a molecule that includes the amino acid sequence of SEQ ID NO.5 or a variant thereof, with the TNF receptor;

determining the ability of the agent to modulate one or more of p38, JNK and ERK1/2 signalling by the TNF receptor; and identifying the agent as an agent that modulates one or more of p38, JNK and ERK1/2 signalling by the TNF receptor.

The present invention also provides a receptor consisting of:

(i) amino acids 209 to 211 as provided in SEQ ID NO. 1, or amino acids 253 to 255 of the receptor as provided in SEQ ID NO. 2, or a variant thereof;

(ii) a transmembrane domain; and (iii) all or part of a cytoplasmic domain of a receptor, or a functional variant thereof, the all or part of the cytoplasmic domain sufficient to mediate signalling through one or more of the p38, NFκB, JNK and ERK1/2 pathways; and wherein the isolated receptor optionally includes one or more exogenous amino acids.

The present invention also provides an antagonist of a ligand of a cell receptor, wherein the antagonist includes and/or mimics a region of the receptor that is involved with selective modulation of one or more signalling pathways controlled by the receptor upon binding of the ligand to the receptor.

The present invention also provides an agonist of a ligand of a cell receptor, wherein the agonist includes or mimics a region of the receptor that is involved with selective modulation of one or more signalling pathways controlled by the receptor upon binding of the ligand to the receptor.

The present invention also provides a soluble TNF-α antagonist including SEQ ID NO:8, or variant thereof.

The present invention also provides an isolated peptide selected from the group consisting of Gly-Thr-Thr (SEQ ID NO.8), Leu-Lys-Pro-Gly-Thr-Thr (SEQ ID NO.9), $His_6$-Leu-Lys-Pro-Gly-Thr-Thr (SEQ ID NO.10), and Gly-Thr-Glu-Asp-Ser-Gly-Thr-Thr-Val (SEQ ID NO.11) and Glu-Asp-Ser-Gly-Thr-Thr (SEQ ID NO.12), or a variant thereof.

Various terms that will be used throughout the specification have meanings that will be well understood by a skilled addressee. However, for ease of reference, some of these terms will now be defined.

The term "receptor" as used throughout the specification is to be understood to mean a molecule or molecular structure within a cell, or on the surface of a cell, that has the property of binding a specific molecule (eg a cytokine, a hormone, and natural or synthetic mediators) and which produces a biological effect upon binding of the specific molecule by transducing a signal from the receptor. It will be appreciated that the receptor may be for example a natural receptor, a variant of a natural receptor, or a synthetic receptor.

The term "subject" as used throughout the specification is to be understood to mean any human or animal subject. In this regard, it will be understood that the present invention includes within its scope veterinary applications. For example, the animal subject may be a mammal, a primate, a livestock animal (eg. a horse, a cow, a sheep, a pig, or a goat), a companion animal (eg. a dog, a cat), a laboratory test animal (eg. a mouse, a rat, a guinea pig, a bird), an animal of veterinary significance, or an animal of economic significance.

The term "biological system" as used throughout the specification is to be understood to mean any multi-cellular system. For example, the biological system may be isolated cells, the part or whole of a tissue or organ, or an entire multi-cellular organism, such as a human or animal.

The term "variant" as used throughout the specification is to be understood to mean an amino acid sequence of a polypeptide or protein that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids. A variant may also be a form of the protein that has one or more deleted amino acids (eg a truncated form of the protein), and/or a form of the protein that has one or more additional exogenous amino acids (eg a form of the protein fused to another polypeptide sequence). It will be appreciated that a variant will therefore include within its scope a fragment of a protein.

Generally, the variant will be a functional variant, that is, a variant that retains the functional ability of the progenitor protein.

Possible functional variants include: (i) a variant that has one or more "conservative" changes, wherein a substituted amino acid has similar structural or chemical properties to the replaced amino acid; and/or (ii) a variant that has one or more "non-conservative" changes; and/or (iii) a variant that has a deletion and/or insertion of one or more amino acids.

Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Under some circumstances, substitutions within the aliphatic group alanine, valine, leucine and isoleucine are also considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative.

The term "nucleic acid" as used throughout the specification is to be understood to mean to any oligonucleotide or polynucleotide. The nucleic acid may be DNA or RNA and may be single stranded or double stranded. The nucleic acid may be any type of nucleic acid, including a nucleic acid of genomic origin, cDNA origin (ie derived from a mRNA), derived from a virus, or of synthetic origin.

In this regard, an oligonucleotide or polynucleotide may be modified at the base moiety, sugar moiety, or phosphate backbone, and may include other appending groups to facilitate the function of the nucleic acid. The oligonucleotide or polynucleotide may be modified at any position on its structure with constituents generally known in the art. For example, an oligonucleotide may include at least one modified base moiety which is selected from the group including 5-fluorouracil, 5-bromouracil, 5-chlorouracil, 5-iodouracil, hypoxanthine, xanthine, 4-acetylcytosine, 5-(carboxyliydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The oligonucleotide or polynucleotide may also include at least one modified sugar moiety selected from the group including, but not limited to, arabinose, 2-fluoroarabinose, xylulose, and hexose. In addition, the oligonucleotide or polynucleotide may include at least one modified phosphate backbone, such as a phosphorothioate, a phosphorodithioate, a phosphoramidothioate, a phosphoramidate, a phosphordiamidate, a methylphosphonate, an alkyl phosphotriester, and a formacetal or any analogue thereof.

The term "modulate" or variants thereof as used throughout the specification is to be understood to mean any alteration in the activity of a process. For example, alteration may result in activation of a process, inhibition of a process, a change in the timing of a process or a change in probability that a process may occur.

In this regard, the term "inhibit" or variants thereof as used throughout the specification is to be understood to mean a reduction in the progress of a process, including any one or more of the start, continuation or termination of a process. Conversely, the term "activate" or variants thereof as used throughout the specification is to be understood to mean an increase in the progress of a process, including any one or more of the start, continuation or termination of a process.

The term "isolated" as used throughout the specification is to be understood to mean an entity, for example a polypeptide, nucleic acid, antibody or a cell, which is removed from its natural environment.

The term "polypeptide" as used throughout the specification is to be understood to mean any polypeptide comprising two or more amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than those normally encoded by a codon.

Polypeptides may also include amino acid sequences modified either by natural processes, such as post-translational processing, or by chemical modification techniques that are well known in the art. Modifications may occur anywhere in a polypeptide, including the peptide backbone, the amino acid side-chains and the amino or carboxyl termini.

GENERAL DESCRIPTION OF THE INVENTION

Figure 1:
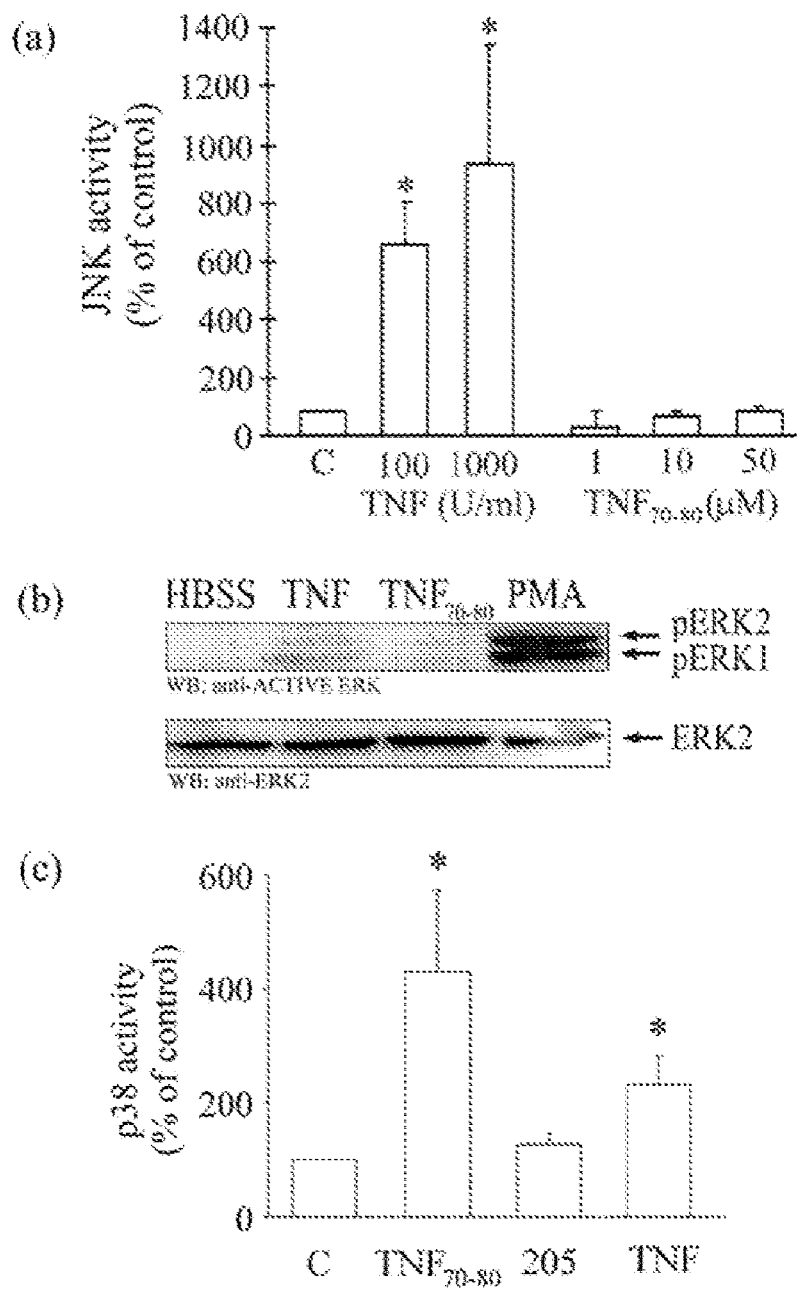
FIG. 1(a)-(c) show activation of MAP kinases in human umbilical vein endothelial cells by TNF but not by $TNF_{70-50}$. (a) To investigate the activation of JNK, HUVEC were incubated in the absence or presence of TNF (100 or 1000 U/ml) or $TNF_{70-80}$ (1-50 µM) for 15 min. The cells were lysed, and JNK activity was assayed using GST-jun (1-79) as a substrate. The data is presented as means+−sem of 3 experiments. Significance of difference between control and TNF: *$p<0.05$. (b) To assess the effects on ERK1/ERK2 dual phosphorylation, cells were incubated in the presence or absence of TNF (100 U/ml), $TNF_{70-80}$ (10 µM) or PMA (100 nM) for 15 (TNF and $TNF_{70-80}$) or 5 (PMA) min. The cells were lysed and the level of dual-phosphorylated ERK1/ERK2 was assessed by western blot analysis using the anti-ACTIVE ERK antibody (top panel). The blot was stripped and re-probed with an anti-ERK2 antibody (lower panel) to compare the level of ERK2 protein. The results are representative of 3 experiments, each conducted with cells from a different cord. (c) To investigate the effects on p38 activation, cells were incubated with either TNF (1,000 U/ml), $TNF_{70-80}$ (10 µM) or control peptide 205 (10 µM) for 5 min, lysed, and p38 activity was assayed. The level of myelin basic protein phosphorylation was quantitated by an Instant Imager. Results are presented as the means+−sem of 3 experiments. Statistical analysis: significant difference between control and stimulated cells, *$p<0.05$.

As described above, in one embodiment the present invention provides a method of selectively modulating a signalling pathway of interest controlled by a cell receptor involved in signalling through multiple signalling pathways, the method including exposing the receptor to an agent that modulates signalling by the receptor through the signalling pathway of interest and which does not substantially modulate signalling through one or more other signalling pathways controlled by the receptor.

Receptors and their intracellular signalling pathways play a fundamental in both the biology of normal and pathological processes. The present invention is based on the finding that it is possible to selectively modulate receptor signalling using mimetic peptides of ligands. The ability to selectively modulate signalling indicates that it possible to modulate biological responses controlled by receptors, and therefore the present invention provides a means for therapeutic intervention in many diseases, conditions and states.

The cell receptor in the various embodiments of the present invention may be a human or animal receptor, or a receptor derived from a human or animal receptor, such as a variant of a receptor.

Although the present invention is primarily directed to selective modulation of cell signalling for a receptor present in a cell, it will be understood that the invention is not to be so limited, and that the invention includes for example within its scope the modulation of signalling in a cell-free in vitro system.

In one embodiment, the receptor is present in a cell in vivo or in vitro.

For example, the receptor may be a receptor associated with a cell in in vitro cell culture. Alternatively, the receptor may be present in a cell that is part of a biological system, such as a cell present in vivo, including a cell that is associated with a disease, condition or state in a subject.

In this regard, the term "biological system" is to be understood to mean any multi-cellular system and includes isolated groups of cells to whole organisms. For example, the biological system may be a tissue or organ, or an entire subject.

The cell receptor may be for example an endogenous receptor, an exogenous receptor, a naturally occurring receptor, a variant of a naturally occurring receptor, or a synthetic receptor.

In the case of introducing exogenous receptor into cells, such methods are known in the art. For example, a nucleic acid encoding a receptor may be introduced into a cell and the receptor expressed in the cell. Methods for cloning, introducing nucleic acids into cells, and expressing proteins in the various embodiments are as previously described herein.

Nucleic acid may be introduced into a cell by various methods known in the art, including transformation using calcium phosphate, viral infection, electroporation, lipofection, and particle bombardment. Methods for introducing DNAs into cells are described in Sambrook, J, Fritsch, E. F. and Maniatis, T. Molecular Cloning: A Laboratory Manual 2nd. ed. Cold Spring Harbor Laboratory Press, New York. (1989).

In one embodiment, the cell receptor of the present invention is a cell surface molecule, such as a cytokine receptor.

Examples of cytokine receptors include Hematopoetin Receptors such as IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, CD4, IL-17 receptor, IL-17E receptor, IL-19 receptor, IL-21 receptor, IL-22 receptor, GMCSF receptor, GCSF receptor, EPO receptor, LIF receptor, OSM receptor I, OSM receptor II, and CNTF receptor; Interleukin-1 Receptors such as IL-1RI, IL-1RII, ST2, IL-18 receptor, IL-IRrp2, TIGGR-1, IL1RAPL, Toll-1, Toll-2, Toll-3, Toll-4, Toll-5, Toll-6, Toll-7, Toll-9; and TNF receptors such as TNFR1, TNFR2, LTβR, HVEM, CD27, 4-1BB, FAS, OX40, SITR, DR3, CD30, TRAIL-R1, TRAIL-R2, TRAIL-R3, TRAIL-R4, RANK, BAFFR, TACI, BCMA, Fn14, CD40, EDAR, XEDAR, DR6, RELT, NGFR, and TROY.

In one embodiment, the cell receptor of the present invention is TNF Receptor 1 (TNFR1) or TNF Receptor 2 (TNFR2).

In this regard, TNF mediates its effects through two major receptors, TNFR1 (also called p55 or p60) and TNFR2 (also called p75 or p80). TNFR1 is expressed on all cell types in the body, while TNFR2 is expressed selectively on endothelial cells and on cells of the immune system.

Methods are known in the art for identifying receptors. For example, a person skilled in the art can readily identify a cytokine receptor, and receptors that belong to different families of cytokine receptors. Cytokine receptors and their ligands are for example as described in "Cytokines and Cytokine Receptors-Physiology and Pathological Disorders" (2000) ed. by C. A. Bona and J-P. Revillard OPA N.V.

In this regard, the accession number for the amino acid sequence of human TNFR1 for example is P19438, and is designated SEQ ID NO.1. The accession number for the amino acid sequence of human TNFR2 is P20333, and is designated SEQ ID NO.2. TNFR1 and TNFR2 receptors from other species may be readily identified, for example by use of the BLAST algorithm, which determines the extent of homology between two nucleotide sequences (blastn) or the extent of homology between two amino acid sequences (blastp). BLAST identifies local alignments between the sequences in the database and predicts the probability of the local alignment occurring by chance. The BLAST algorithm is as described in Altschul et al. (1990) *J. Mol. Biol.* 215:403-410.

In the case of TNFR1 or TNFR2, in one embodiment the signalling pathway of interest is the p38 signalling pathway and/or the NFκB signalling pathway.

In one embodiment, the one or more other signalling pathways is one or more of the JNK signalling pathway, the ERK1/2 signalling pathway, and the PI3K signalling pathway.

Thus, in the case of TNFR1 and TNFR2, the present invention may be used for example to selectively modulate p38 and/or the NFκB signaling by the receptor, by exposing the receptor to an agent that modulates p38 and/or the NFκB signalling by the receptor and which does not substantially modulate signalling through one or more of the JNK, ERK1/2 and PI3K signalling pathways controlled by the receptor.

Accordingly, the present invention also provides a method of selectively modulating p38 and/or NFκB signalling by TNFR1 or TNFR2 without substantially modulating one or more of JNK, ERK1/2 and PI3K signalling by the receptor, the method including exposing the receptor to an agent that modulates p38 and/or the NFκB signalling and does not substantially modulate signalling through one or more of the JNK, ERK1/2 and PI3K signalling pathways controlled by the receptor.

In this regard, pro-inflammatory cytokines, such as TNF, stimulate the activities of a number of intracellular signalling molecules, including MAP kinases, sphingomyelinases, members of the NFκB module and those which signal for cell death.

TNF for example has roles in immune surveillance, tumour regression, haematopoiesis, protection from bacterial infection and innate immunity.

One of the key mediators of the actions of TNF is the MAP kinase, p38. p38 consists of $\alpha$, $\beta$, $\gamma$ and $\delta$ isoforms which are activated when cells respond to inflammatory stimuli and stress. Inhibitors of p38 kinase block the production of inflammatory cytokines TNF, IL-1 and IL-6, and the actions of these cytokines. p38 plays a major role in the regulation of expression of inflammatory response genes and in regulation of IL-6 and IL-8 mRNA. The crucial role played by p38 in both the production and action of TNF and other inflammatory cytokines make the p38 module a therapeutic target to treat a number of diseases, including inflammatory diseases.

In one embodiment, the method may used to selectively activate p38 and/or NFκB signalling by the receptor without substantially activating one or more of JNK, ERK1/2 and PI3K signalling by the receptor, by exposing the receptor to an agent that activates p38 and/or NFκB signalling and does not substantially activate signalling through one or more of the JNK, ERK1/2 and PI3K signalling pathways controlled by the receptor.

Alternatively, the method may be used to selectively inhibit p38 and/or NFκB signalling by TNFR1 or TNFR2, by exposing the receptor to an agent that inhibits p38 and/or NFκB signalling by the receptor and does not substantially inhibit signalling through one or more of the JNK, ERK1/2 and PI3K signalling pathways controlled by the receptor.

In this regard, p38 is known to play a role in many diseases, conditions and states, including those known caused by IL-1, TNF, IL-6 or IL-8 overproduction.

Such diseases, conditions and states are referred to herein as p38-mediated diseases, conditions or states and include for example inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Examples of inflammatory diseases include cystic fibrosis, acute pancreatitis, chronic pancreatitis, asthma, allergies, and adult respiratory distress syndrome.

Examples of autoimmune diseases include glomerulonephritis, rheumatoid arthritis, systemic lupus erythematosus, scleroderma, chronic thyroiditis, Graves' disease, autoimmune gastritis, diabetes (and complications thereof including nephropathy, neuropathy, retinopathy, and cardiovascular disease), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Examples of destructive bone disorders include osteoporosis, osteoarthritis and multiple myeloma-related bone disorder.

Examples of proliferative diseases include acute myelogenous leukemia, chronic myelogenous leukemia, metastatic melanoma, Kaposi's sarcoma, and multiple myeloma.

Examples of angiogenic disorders include solid tumors, ocular neovasculization, infantile haemangiomas.

Examples of infectious diseases include sepsis, septic shock, and Shigellosis.

Examples of viral diseases include acute hepatitis infection (including hepatitis A, hepatitis B and hepatitis C), influenza A and B, HIV infection and CMV retinitis.

Examples of neurodegenerative diseases include Alzheimer's disease, Parkinson's disease, cerebral ischemias or neurodegenerative disease caused by traumatic injury.

Other conditions include ischemia/reperfusion in stroke, heart attacks, myocardial ischemia, organ hypoxia, vascular hyperplasia, cardiac hypertrophy, and thrombin-induced platelet aggregation.

Inhibitors of p38 inhibitors are also capable of inhibiting the expression of inducible pro-inflammatory proteins such as prostaglandin endoperoxide synthase-2 (PGHS-2), also referred to as cyclooxygenase-2 (COX-2). Therefore, other p38-mediated conditions include edema, analgesia, fever and pain, such as neuromuscular pain, headache, cancer pain, dental pain and arthritis pain.

Diseases, conditions and states that may be treated or prevented by p38 inhibitors may also be conveniently grouped by the cytokine (IL-1, TNF, IL-6, IL-8) that is believed to be responsible for the disease.

IL-1-mediated diseases, conditions and states include for example rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes (and complications thereof including nephropathy, neuropathy, retinopathy, and cardiovascular disease), pancreatic.beta.-cell disease and Alzheimer's disease.

TNF-mediated diseases, conditions and states include fever, psoriasis, allergic asthma, inflammatory bowel disease, pulmonary fibrosis, tumourigenesis, lymphoproliferative disease, sclerodema, osteoporosis and bone resorption, Alzheimer's disease, Diabetes (type II), heart failure, atherosclerosis, hepatitis, multiple sclerosis, AIDS, pruritic inflammatory disease, mucocutaneous disease, systemic lupus erythematosus, transplant rejection, atopic dermatitis, sarcoidosis, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated diseases, conditions and states include diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, conditions caused or exacerbated by IL-1 or TNF include inflamed joints, eczema, psoriasis, inflammatory skin conditions such as sunburn, inflammatory eye conditions such as conjunctivitis, pyresis, pain and other conditions associated with inflammation.

The agent in the various relevant embodiments of the present invention may modulate signalling through one or more pathways of interest by acting through a region of the receptor that is involved in modulation of signalling.

In one embodiment, the agent may interact with, or bind to, a region of the receptor to effect selective modulation of signalling.

For example, in the case of modulating the activity of the p38 signalling pathway in TNFR1 or TNFR2, the agent may act through a region of TNFR1 including one or more amino acids 209 to 211 of the receptor as provided in SEQ ID NO. 1, or the agent may act through a region of TNFR2 including one or more of amino acids 253 to 255 of the receptor as provided in SEQ ID NO. 2.

Accordingly, in one embodiment the agent interacts with a region of TNFR1 that includes one or more of amino acids 209 to 211 of SEQ ID NO.3 and/or interacts with a region of TNFR2 that includes one or more of amino acids 253 to 255 of SEQ ID NO.2.

In the case of TNFR1 or TNFR2, the signalling pathway of interest may also be one or more of the JNK signalling pathway, the ERK1/2 signalling pathway, and the PI3K signalling pathway, and the one or more other signalling pathways may be the p38 signalling pathway and/or the NFκB signalling pathway.

Accordingly, the present invention may also be used to selectively modulate one or more of JNK, ERK1/2 and PI3K signalling by TNFR1 or TNFR2 without substantially modulating p38 and/or NFκB signalling by the receptor, by exposing the receptor to an agent that modulates one or more of JNK, ERK1/2 and PI3K signalling and which does not substantially modulate signalling through the p38 and/or the NFκB signalling pathways controlled by the receptor.

In one embodiment, the method may be used to selectively activate one or more of JNK, ERK1/2 and PI3K signalling by TNFR1 or TNFR2, by exposing the receptor to an agent that activates one or more of JNK, ERK1/2 and PI3K signalling by the receptor and does not substantially activate signalling through the p38 and/or the NFκB signalling pathway controlled by the receptor.

In another embodiment, the method may be used to selectively inhibit one or more of JNK, ERK1/2 and PI3K signalling by TNFR1 or TNFR2, by exposing the receptor to an agent that inhibits one or more of JNK, ERK1/2 and PI3K signalling by the receptor and does not substantially inhibit signalling through the p38 and/or the NFκB signalling pathways controlled by the receptor.

It will be appreciated that the selective modulation of signalling in the various embodiments of the present invention includes modulating signalling of an intracellular signalling pathway downstream of a receptor.

For example, the modulation of an intracellular signalling pathway downstream of the receptor may be achieved by exposing a cell having the cell receptor to an agent that modulates the intracellular signalling pathway directly or indirectly.

The present invention may also be used to modulate one or more of JNK, ERK1/2 and PI3K signalling upon binding of TNF-α to TNFR1 and/or TNFR2 on a cell by exposing the cell to an agent that alters the activity of TNF-α to modulate one or more of JNK, ERK1/2 and PI3K signalling upon binding of TNF-α to the receptor.

Accordingly, in another embodiment the present invention provides a method of modulating one or more of JNK, ERK1/2 and PI3K signalling upon binding of TNF-α to TNFR1 and/or TNFR2 on a cell, the method including exposing the cell to an agent that alters the activity of TNF-α to modulate one or more of JNK, ERK1/2 and PI3K signalling upon binding of TNF-α to the receptor.

In one embodiment, the method is used to inhibit one or more of JNK, ERK1/2 and PI3K signalling.

In one embodiment, the agent interacts with a region of TNF-α including one or more of amino acids 132 to 150.

In one embodiment, the agent interacts with a region of TNFR1 that includes one or more of amino acids 209 to 211 of SEQ ID NO. 1 and/or interacts with a region of TNFR2 that includes one or more of amino acids 253 to 255 of SEQ ID NO. 2.

In one embodiment, the agent does not substantially inhibit p38 and/or NFκB signalling upon binding of TNF-α to the receptor.

The present invention may also be used to modulate p38 and/or NFκB signalling upon binding of TNF-α to TNFR1 and/or TNFR2 on a cell by exposing the cell to an agent that alters the activity of TNF-α to modulate p38 and/or NFκB signalling upon binding of TNF-α to the receptor.

Accordingly, in another embodiment the present invention provides a method of modulating p38 and/or NFκB signalling upon binding of TNF-α to TNFR1 and/or TNFR2 on a cell, the method including exposing the cell to an agent that alters the activity of TNF-α to modulate p38 and/or NFκB signalling upon binding of TNF-α to the receptor.

In one embodiment, the agent interacts with a region of the TNFR1 that includes one or more of amino acids 209 to 211 of SEQ ID NO. 1 and/or interacts with a region of TNFR2 that includes one or more of amino acids 253 to 255 of SEQ ID NO. 2.

In one embodiment, the method is used to inhibit p38 and/or NFκB signalling.

In one embodiment, the agent binds to a region of TNF-α including one or more of amino acids 70 to 80.

In one embodiment, the agent does not substantially inhibit one or more of JNK, ERK1/2 and PI3K signalling upon binding of TNF-α to the receptor.

Examples of agents in the various embodiments of the present invention include a small molecule, a nucleic acid, an oligonucleotide, a peptide, a polypeptide, a protein, a peptide mimetic, a non-peptide mimetic, an enzyme, a polysaccharide, a glycoprotein, a lipid, an antibody or a part thereof, and an aptamer, or any combination thereof.

In one embodiment, the agent is a mimetic of a ligand of the receptor. Methods for producing ligand mimetics are known in the art. A ligand mimetic may be, for example, a peptide mimetic or a non-peptide mimetic.

For example, in the case of selectively modulating p38 signalling controlled by a TNF receptor, in one embodiment the agent is a TNF-α mimetic (including a peptide mimetic or a non-peptide mimetic).

Examples of TNF-α mimetic peptides that may be used to selectively activate p38 signalling without substantially activating JNK and ERK1/2 signalling includes an agent including the amino acid sequence Pro-Ser-Thr-His-Val-Leu-Leu-Thr-His-Thr-Ile (SEQ ID NO. 3), or a variant thereof, or an agent including the amino acid sequence Pro-Ser-Thr-His-Val-Leu-Ile-Thr-His-Thr-Ile-OH (SEQ ID NO. 4), or a variant thereof.

In this regard, SEQ ID NO. 3 corresponds to amino acids 70 to 80 of the processed form of human TNF-α, while SEQ ID NO. 4 corresponds to a Leu to Ile variant of this sequence. The amino acid sequence of the processed form of human TNF-α is provided as SEQ ID NO. 11.

In one embodiment, the agent includes an amino acid sequence as provided in SEQ ID NO. 3 and/or SEQ ID NO.4, or a variant thereof.

In one specific embodiment, the agent is a polypeptide with the amino acid sequence Pro-Ser-Thr-His-Val-Leu-Leu-Thr-His-Thr-Ile (SEQ ID NO. 3), or a variant thereof, or a polypeptide with the amino acid sequence Pro-Ser-Thr-His-Val-Leu-Ile-Thr-His-Thr-Ile-OH (SEQ ID NO. 4) or a variant thereof, which is also alternatively referred to herein as "Peptide A" or $TNF_{70-80}$.

In another embodiment, the agent is a non-peptide mimetic of the polypeptide with the amino acid sequence as provided in SEQ ID NO. 3 and/or SEQ ID NO.4.

In the case of selectively modulating JNK and ERK1/2 signalling controlled by a TNF receptor, in one embodiment the agent is also a TNF-α mimetic.

Examples of TNF-α mimetic peptides that may be used to selectively activate JNK and ERK1/2 signalling without substantially activating p38 signalling include polypeptides that include the amino acid sequence Leu-Ser-Ala-Glu-Ile-Asn-Arg-Pro-Asp-Tyr-Leu-Asp-Phe-Ala-Glu-Ser-Gly-Gln-Val (SEQ ID NO. 5), or a variant thereof. SEQ ID NO. 5 corresponds to amino acids 132 to 150 of the processed form of human TNF-α, and which is also alternatively referred to herein as "$TNF_{132-150}$" or "Peptide B".

In one embodiment, the agent includes an amino acid sequence as provided in SEQ ID NO. 5, or a variant thereof.

In another embodiment, the agent is a polypeptide with the amino acid sequence as provided in SEQ ID NO.5, or a variant thereof.

In another embodiment, the agent is a non-peptide mimetic of the polypeptide with the amino acid sequence as provided in SEQ ID NO. 5.

Methods for determining whether a signalling pathway has been modulated are known in the art.

As discussed previously herein, the ability to selectively modulate signalling demonstrates that it possible to modulate one or more biological responses controlled by a receptor. The biological responses may be produced by a cell, a biological system or a subject.

Accordingly, in another embodiment the present invention provides a method of selectively modulating a biological response of interest produced by signalling through a cell receptor involved in signalling through multiple signalling pathways, the method including selectively modulating signalling through one or more specific signalling pathways controlled by the cell receptor without substantially modulating signalling through one or more other signalling pathways controlled by the cell receptor, wherein the selective modulation of signalling through the one or more specific signalling pathways modulates the biological response of interest without substantially modulating one or more other biological responses produced by signalling through the one or more other signalling pathways.

In the case of TNFR1 or TNFR2, the biological response of interest may be, for example, one or more of immunity against infection by a virus or a pathogen, phagocyte and/or natural killer cell killing of tumour cells, activation of immune function, suppression of immune function, pain, sepsis and leukocyte activation.

In one embodiment, the one or more specific signalling pathways is the p38 signalling pathway and/or the NFκB signalling pathway.

In one embodiment, the one or more other signalling pathways is one or more of the JNK signalling pathway, the ERK1/2 signalling pathway, and the PI3K signalling pathway.

For example, the biological response of interest may be associated with activation of p38 signalling through the TNF receptor, such as immunity against infection and/or killing of tumour cells, and the one or more other biological responses is a pathogenetic response associated with activation of JNK and/or ERK1/2 signalling through the TNF receptor.

In another embodiment, the biological response of interest is associated with inhibitor of p38 signalling.

The method of modulating a biological response of interest may include exposing the cell receptor to an agent that modulates signalling by the receptor through the one or more specific signalling pathways and which does not substantially modulate signalling through the one or more other signalling pathways controlled by the receptor. Thus, exposing the cell with the receptor may be used to modulate the biological response of interest.

In one embodiment, the agent interacts with a region of the receptor that selectively modulates the signalling pathway of interest by the receptor. For example, in the case of modulating the activity of the p38 signalling pathway in TNFR1 or TNFR2, the agent may act through a region of TNFR1 including one or more of amino acids 209 to 211 of TNFR1 as provided in SEQ ID NO. 1, or the agent may act through a region of TNFR2 including one or more of amino acids 253 to 255 of the receptor as provided in SEQ ID NO. 2.

In another embodiment, the one or more specific signalling pathways is one or more of the JNK signalling pathway, the ERK1/2 signalling pathway and the PI3K signalling pathway.

In another embodiment, the one or more other signalling pathways is the p38 and/or the NFκB signalling pathway.

In one specific embodiment the biological response of interest is associated with activation of one or more of JNK and/or ERK1/2 signalling through the TNF receptor, such as sepsis.

In another specific embodiment, the biological response of interest is associated with inhibition of one or more of JNK and/or ERK1/2 signalling through the TNF receptor The present invention may also be used to prevent and/or treat a disease, condition or state in a subject that would benefit from selective modulation of the one or more signalling pathways controlled by the receptor in the subject.

Accordingly, in another embodiment the present invention provides a method of preventing and/or treating a disease, condition or state in a subject that would benefit from selective modulation of the one or more signalling pathways controlled by a cell receptor in the subject, the method including administering to the subject an effective amount of an agent that modulates signalling through the one or more signalling pathways and which does not modulate signalling through one or more other signalling pathways controlled by the receptor.

Other diseases, conditions and states that may be prevented and/or treated are as previously discussed herein.

For example, in the case of TNFR1 or TNFR2, the method may be used to prevent and/or treat in a subject one or more of fever, psoriasis, Chrohn's disease, asthma including allergic asthma, septic shock, inflammatory bowel disease, pulmonary fibrosis, tumorigenesis, lymphoproliferative diseases, scleroderma, osteoporosis, bone resportion, Alzheimer's disease, Diabetes (type I and type II and complications thereof including nephropathy, neuropathy, retinopathy, and cardiovascular disease), heart failure, atherosclerosis, hepatitis, multiple sclerosis, AIDS, pruritic inflammatory disease, mucocutaneous disease, systemic lupus erythematosus, rheumatoid arthritis, transplant rejection, atopic dermatitis, sarcoidosis, infection by a virus, infection by a pathogen, cancer, an inflammatory disease, an allergic reaction, sepsis, pain, autoimmune diseases, cystic fibrosis and other p38-mediated diseases, IL-1 mediated diseases, TNF-mediated diseases, and IL-8 mediated diseases previously discussed herein.

These diseases, conditions and states may be prevented and/or treated by selectively modulating one or more of the p38, NFκB, JNK, ERK1/2 and PI3K signalling pathways of the receptor.

In one embodiment, the diseases, conditions and states may be prevented and/or treated by administering to the subject an agent that selectively activates the p38 and/or NFκB signalling pathway in TNFR1 or TNFR2 in the subject and does not substantially activate one or more of the JNK, ERK1/2 and PI3K signalling pathways in TNFR1 or TNFR2 in the subject.

For example, in the case of cystic fibrosis (CF) although at present CF individuals are living longer because of better management and antibiotic application, they rarely survive past their mid-thirties. Approximately 90% of CF mortalities are a result of recurrent pulmonary infection and ultimately pulmonary failure. The major cause of morbidity and mortality in cystic fibrosis is the self-perpetuating cycle of airway obstruction, chronic bacterial infection and vigorous inflammation. The lung damage is primarily due to an influx of a large number of white cells called neutrophils. As such, treating inflammation in cystic fibrosis is a major goal. The present invention allows signalling selectively via p38 through TNF receptor and thereby overcome the major problems with previous therapeutic strategies. For example, agents as described herein can be used to selectively block this pathway and hence the inflammation seen in CF.

It will also be appreciated that in a number of chronic inflammatory diseases, TNF is a key cytokine which either acts directly to stimulate oxygen reactive species generation and release of lysosomal enzymes or indirectly by stimulating IL-1, IL-6 and IL-8 production from both neutrophils and macrophages. Thus, the present invention may be used to prevent and/or treat inflammatory disorders, such as rheumatoid arthritis and CF.

In one embodiment, the present invention may be used to prevent and/or treat in a subject one or more of infection by a virus, infection by a pathogen, cancer, an inflammatory disease, asthma, an allergic reaction, atherosclerosis, diabetes (and complications thereof including nephropathy, neuropathy, retinopathy, and cardiovascular disease), sepsis, pain, autoimmune diseases, cystic fibrosis, and rheumatoid arthritis, by administering to the subject an agent that selectively activates the p38 and/or NFκB signalling pathway in TNFR1 or TNFR2 in the subject and does not substantially activate one or more of the JNK, ERK1/2 and PI3K signalling pathways in TNFR1 or TNFR2 in the subject.

In another embodiment, the present invention may be used to prevent and/or treat sepsis in a subject, by administering to the subject an agent that selectively activates one or more of the JNK, ERK1/2 and PI3K signalling pathways in TNFR1 or TNFR2 in the subject and does not substantially activate the p38 and/or NFκB signalling pathways in TNFR1 or TNFR2 in the subject.

In another embodiment, the present invention may be used to prevent and/or treat a viral or pathogen infection in a subject, by administering to the subject an effective amount of an agent that activates p38 signalling by TNFR1 or TNFR2 and does not substantially activate JNK and/or ERK1/2 signalling by the receptor.

In another embodiment, the present invention may be used to prevent and/or treat a cancer in a subject, by administering to the subject an effective amount of an agent that activates p38 signalling by TNFR1 or TNFR2 receptor and does not substantially activate JNK and/or ERK1/2 signalling by the receptor.

In another embodiment, the present invention may be used to prevent and/or treat sepsis in a subject, by administering to the subject an effective amount of an agent that activates JNK and/or ERK1/2 signalling by TNFR1 or TNFR2 and does not substantially activate p38 signalling by the receptor.

Other diseases, conditions and states that may be prevented and/or treated are as previously discussed herein, including p38-mediated diseases, IL-1 mediated diseases, TNF-mediated diseases, and IL-8 mediated diseases.

In one embodiment, the agent for administration to a subject includes an amino acid sequence as provided in SEQ ID NO. 3 and/or SEQ ID NO. 4, or a variant thereof.

In one embodiment, the agent for administration to a subject is a polypeptide with the amino acid sequence as provided in SEQ ID NO.3 or SEQ ID NO.4, or a variant thereof.

In another embodiment, the agent for administration to a subject is a non-peptide mimetic of the polypeptide with the amino acid sequence as provided in SEQ ID NO. 3 or SEQ ID NO.4.

In one embodiment, the agent for administration to a subject interacts with a region of the TNFR1 that includes one or more of amino acids 209 to 211 of SEQ ID NO. 1 and/or interacts with a region of TNFR2 that includes one or more of amino acids 253 to 255 of SEQ ID NO. 2.

In another embodiment, the agent for administration to a subject interacts with a region of TNF-α including one or more of amino acids 132 to 150.

In another embodiment, the agent for administration to a subject includes an amino acid sequence as provided in SEQ ID NO. 5, or a variant thereof.

In another embodiment, the agent for administration to a subject is a polypeptide with the amino acid sequence as provided in SEQ ID NO. 5, or a variant thereof.

In another embodiment, the agent for administration to a subject is a non-peptide mimetic of the polypeptide with the amino acid sequence as provided in SEQ ID NO. 5.

The present invention may also be used in the preparation of a medicament for preventing and/or treating a disease, condition or state in a subject that would benefit from selective modulation of the one or more signalling pathways controlled by a cell receptor in the subject.

In one embodiment, the present invention provides the use of an agent that selectively activates p38 signalling by TNFR1 or TNFR2 and does not substantially activate JNK and/or ERK1/2 signalling by the receptor in the preparation of a medicament for preventing and/or treating a viral or pathogen infection in a subject.

In another embodiment, the present invention provides the use of an agent that selectively activates p38 signalling by TNFR1 or TNFR2 and does not substantially activate JNK and/or ERK1/2 signalling by the receptor in the preparation of a medicament for preventing and/or treating cancer.

In another embodiment, the present invention provides the use of an agent that selectively activates JNK and/or ERK1/2 signalling by TNFR1 or TNFR2 and does not substantially activate p38 signalling by the receptor in the preparation of a medicament for preventing and/or treating sepsis.

In the case of an agent being exposed to a receptor to selectively modulate signalling in the various embodiments of the present invention, a suitable method for exposing the agent to a receptor associated with a cell is by direct exposure of the agent to, or by contact of the agent with, the cell.

In the case of the agent being exposed to a cell in a biological system such as a subject, the agent may be administered to the biological system. The agent may be delivered in a form and at a concentration suitable to allow the agent to reach the desired site of action and have the effect of selectively modulating signalling.

In this case, the administration of the agent may be within any time suitable to produce the desired effect of selectively modulating signalling. For example, in a human or animal subject, the agent may be administered orally, parenterally, topically or by any other suitable means, and therefore transit time of the agent must be taken into account.

The agent may be formulated into a pharmaceutical composition for administration to a subject, and as such the composition may be packaged in a suitably sterilized container such as an ampoule, bottle, or vial, either in multi-dose or in unit dosage forms. The containers will generally be hermetically sealed. Methods are known in the art for the packaging of components for pharmaceutical administration.

As discussed previously herein, the agent may also be used in the preparation of a medicament to prevent and/or treat a disease, condition or state in a subject that would benefit from selective modulation of the one or more signalling pathways controlled by the receptor in the subject. Diseases, conditions and states are as previously discussed herein.

For example, in the case of TNFR1 and TNFR2, an agent that selectively modulates one or more of the p38, NFκB, JNK, ERK1/2 and PI3K signalling pathways of the receptor may be used in the preparation of a medicament to prevent and/or treat in a subject infection by a virus, infection by a pathogen, cancer, an inflammatory disease, asthma, an allergic reaction, atherosclerosis, diabetes, sepsis and pain.

Accordingly, in one embodiment the present invention provides use of an agent that activates the p38 and/or NFκB signalling pathways in TNFR1 or TNFR2 in a subject and which does not substantially activate one or more of the JNK, ERK1/2 and PI3K signalling pathways in TNFR1 or TNFR2 in the subject, in the preparation of a medicament for preventing and/or treating in the subject one or more of infection by a virus, infection by a pathogen, cancer, an inflammatory disease, asthma, an allergic reaction, atherosclerosis, diabetes, and pain.

In another embodiment, the present invention provides use of an agent that activates one or more of the JNK, ERK1/2 and PI3K signalling pathways in TNFR1 or TNFR2 in a subject and which does not substantially activate the p38 and/or NFκB signalling pathways in TNFR1 or TNFR2 in the subject, in the preparation of a medicament for preventing and/or treating sepsis in a subject.

The effective amount of the agent to be administered to the subject in the various embodiments of the present invention is not particularly limited, so long as it is within such an amount and in such a form that generally exhibits a useful or therapeutic effect. The term "therapeutically effective amount" is the quantity which, when administered to a subject in need of treatment, improves the prognosis and/or state of the subject. The amount to be administered to a subject will depend on the particular characteristics of the disease, condition or state in the subject, the mode of administration, and the characteristics of the subject, such as general health, other diseases, age, sex, genotype, body weight and tolerance to drugs. A person skilled in the art will be able to determine appropriate dosages depending on these and other factors.

As discussed previously herein, administration and delivery of the compositions according to the invention may be by the intravenous, intraperitoneal, subcutaneous, intramuscular, oral, or topical route, or by direct injection. The mode and route of administration in most cases will depend on the type of disease, condition or state being treated.

The dosage form, frequency and amount of dose will depend on the mode and route of administration.

For example, effective amounts of the agent typically range between about 0.1 mg/kg body weight per day and about 1000 mg/kg body weight per day, and in one form between 1 mg/kg body weight per day and 100 mg/kg body weight per day.

As described above, the administration of the pharmaceutical compositions may also include the use of one or more pharmaceutically acceptable additives, including pharmaceutically acceptable salts, amino acids, polypeptides, polymers, solvents, buffers, excipients, preservatives and bulking agents, taking into consideration the particular physical, microbiological and chemical characteristics of the agent to be administered.

The preparation of such pharmaceutical compositions is known in the art, for example Remington's Pharmaceutical Sciences, 18th ed., 1990, Mack Publishing Co., Easton, Pa. and U.S. Pharmacopeia: National Formulary, 1984, Mack Publishing Company, Easton, Pa.

For example, the agent can be prepared into a variety of pharmaceutically acceptable compositions in the form of, e.g., an aqueous solution, an oily preparation, a fatty emulsion, an emulsion, a lyophilised powder for reconstitution, etc. and can be administered as a sterile and pyrogen free intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, caplets, capsules, granules or powders; liquid preparations such as syrup, emulsions, dispersions or suspensions).

Compositions containing the agent may also contain one or more pharmaceutically acceptable preservatives, buffering agents, diluents, stabilisers, chelating agents, viscosity enhancing agents, dispersing agents, pH controllers, or isotonic agents. These excipients are well known to those skilled in the art.

Examples of suitable preservatives are benzoic acid esters of para-hydroxybenzoic acid, propylene glycol, phenols, phenylethyl alcohol or benzyl alcohol. Examples of suitable buffers are sodium phosphate salts, citric acid, tartaric acid and the like. Examples of suitable stabilisers are, antioxidants such as alpha-tocopherol acetate, alpha-thioglycerin, sodium metabisulphite, ascorbic acid, acetylcysteine, 8-hydroxyquinoline, chelating agents such as disodium edetate. Examples of suitable viscosity enhancing agents, suspending or dispersing agents are substituted cellulose ethers, substituted cellulose esters, polyvinyl alcohol, polyvinylpyrrolidone, polyethylene glycols, carbomer, polyoxypropylene glycols, sorbitan monooleate, sorbitan sesquioleate, polyoxyethylene hydrogenated castor oil 60.

Examples of suitable pH controllers include hydrochloric acid, sodium hydroxide and the like. Examples of suitable isotonic agents are glucose, D-sorbitol or D-mannitol, sodium chloride.

The administration of the agent in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, glidant, antiadherant, binder, flavorant or sweetener, taking into account the physical, chemical and microbiological properties of the agent being administered.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile, pyrogen free injectable form (solution, suspension or emulsion, which may have been reconstituted prior to use) which is typically isotonic with the blood of the recipient with a pharmaceutically acceptable carrier. Examples of such sterile injectable forms are sterile injectable aqueous or oleaginous suspensions. These suspensions may be formulated according to techniques known in the art using suitable vehicles, dispersing or wetting agents and suspending agents. The sterile injectable forms may also be sterile injectable solutions or suspensions in non-toxic parenterally acceptable diluents or solvents, for example, as solutions in 1,3-butanediol. Among the pharmaceutically acceptable vehicles and solvents that may be employed are water, ethanol, glycerol, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

In addition, the composition may be in a form to be reconstituted prior to administration. Examples include lyophilisation, spray drying and the like to produce a suitable solid form for reconstitution with a pharmaceutically acceptable solvent prior to administration.

Compositions may include one or more buffers, bulking agents, isotonic agents and cryoprotectants and lyoprotectants. Examples of excipients include, phosphate salts, citric acid, non-reducing such as sucrose or trehalose, polyhydroxy alcohols, amino acids, methylamines, and lyotropic salts are generally preferred to the reducing sugars such as maltose or lactose.

When administered orally, the agent will usually be formulated into unit dosage forms such as tablets, caplets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include excipients such as lactose, dextrose, sucrose, sorbitol, mannitol, starches, gum acacia, calcium phosphate, mineral oil, cocoa butter, oil of theobroma, alginates, tragacanth, gelatin, syrup, substituted cellulose ethers, polyoxyethylene sorbitan monolaurate, methyl hydroxybenzoate, propyl hydroxybenzoate, talc, magnesium stearate, and the like.

A tablet may be made by compressing or molding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the agent may also utilize controlled release technology.

The agent may also be administered as a sustained-release pharmaceutical composition. To further increase the sustained release effect, the agent may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof, carboxymethylcellulose sodium hydroxypropylcellulose ether, collagen polyethylene glycol polyethylene oxide, hydroxypropylmethylcellulosemethylcellulose, polyvinyl alcohol, polyvinylpyrrolidone.

Alternatively, the agent may be incorporated into a hydrophobic polymer matrix for controlled release over a period of days. The agent may then be moulded into a solid implant, or externally applied patch, suitable for providing efficacious concentrations of the agents over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers, which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time-release characteristics and release kinetics. The agent may then be moulded into a solid implant suitable for providing efficacious concentrations of the agents over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant. For topical administration, the composition may be in the form of a solution, spray, lotion, cream (for example a non-ionic cream), gel, paste or ointment. Alternatively, the composition may be delivered via a liposome, nanosome, rivosome, or nutri-diffuser vehicle.

The recognition that selective modulation of receptor signalling may be accomplished also indicates that agents may be identified which have the ability to selectively modulate receptor signalling. Agents so identified (for example agonists and antagonists) are candidates for use in therapeutic intervention in a large number of diseases, states or conditions, and thus can be used in the preparation of a medicament for the prevention and/or treatment of such diseases, states or conditions.

Accordingly, in another embodiment the present invention provides a method of identifying an agent that selectively modulates signalling through one or more signalling pathways controlled by a cell receptor, the method including identifying an agent that modulates signalling by the receptor through one or more signalling pathways without substantially modulating signalling by the receptor through one or more other signalling pathways.

Determination that an agent modulates signalling through one or more signalling pathways without substantially modulating signalling by one or more other signalling pathways may be achieved by a suitable method known in the art.

In one embodiment, the cell receptor is a cell surface molecule, such as a cytokine receptor.

Examples of cytokine receptors include Hematopoetin Receptors such as IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, CD4, IL-17 receptor, IL-17E receptor, IL-19 receptor, IL-21 receptor, IL-22 receptor, GMCSF receptor, GCSF receptor, EPO receptor, LIF receptor, OSM receptor I, OSM receptor II, and CNTF receptor; Interleukin-1 Receptors such as IL-1RI, IL-1RII, ST2, IL-18 receptor, IL-IRrp2, TIGGR-1, IL1RAPL, Toll-1, Toll-2, Toll-3, Toll-4, Toll-5, Toll-6, Toll-7, Toll-9; and TNF receptors such as TNFR1, TNFR2, LTβR, HVEM, CD27, 4-1BB, FAS, OX40, SITR, DR3, CD30, TRAIL-R1, TRAIL-R2, TRAIL-R3, TRAIL-R4, RANK, BAFFR, TACI, BCMA, Fn14, CD40, EDAR, XEDAR, DR6, RELT, NGFR, and TROY.

In one embodiment, the cell receptor is TNFR1 or TNFR2. In this case, the agent may for example selectively modulate p38 signalling and/or NFκB signalling upon binding of TNF-α to a TNFR1 or TNFR2, without substantially modulating one or more of the JNK, ERK1/2, and PI3K signalling pathways.

Accordingly, in another embodiment the present invention provides a method of identifying an agent that selectively modulates p38 signalling by TNFR1 and/or TNFR2 without substantially modulating JNK and/or ERK1/2 signalling by the receptor, the method including identifying an agent that modulates p38 signalling by TNFR1 and/or TNFR2 signalling without substantially modulating JNK and/or ERK1/2 signalling by the receptor.

For example, the method may be used to identify an agent that selectively activates p38 signalling and/or NFκB signalling upon binding of TNF-α to a TNFR1 or TNFR2, without substantially activating one or more of the JNK, ERK1/2, and PI3K signalling pathways.

Alternatively, the method may be used to identify an agent that selectively inhibits p38 signalling and/or NFκB signalling upon binding of TNF-α to a TNFR1 or TNFR2, without substantially inhibiting one or more of the JNK, ERK1/2, and PI3K signalling pathways.

The method may also be used to identify an agent that selectively modulates one or more of JNK, ERK1/2, and PI3K signalling pathways upon binding of TNF-α to a TNFR1 or TNFR2, without substantially modulating the p38 and/or NFκB signalling pathways.

Accordingly, in another embodiment the present invention provides a method of identifying an agent that selectively modulates JNK and/or ERK1/2 signalling by TNFR1 and/or TNFR2 without substantially modulating p38 signalling by the receptor, the method including identifying an agent that modulates JNK and/or ERK1/2 signalling without substantially modulating p38 signalling by the receptor.

In one embodiment, the method is used to identify an agent that selectively activates one or more of JNK, ERK1/2, and PI3K signalling pathways upon binding of TNF-α to a TNFR1 or TNFR2, without substantially activating p38 and/or NFκB signalling pathways.

Alternatively, the method may be used to identify an agent that selectively inhibits one or more of JNK, ERK1/2, and PI3K signalling upon binding of TNF-α to a TNFR1 or TNFR2, without substantially inhibiting the p38 signalling and/or NFκB signalling pathways.

In one embodiment, the method of identification includes identifying an agent that modulates signalling through a region of the receptor that is involved in selective modulation of the one or more signalling pathways.

In the case of TNFR1 or TNFR1, the method of identification may involve identifying an agent that modulates TNFR1 or TNFR2 signalling through a region of the receptor associated with p38 signalling and not associated with one or more of JNK, ERK1/2 and PI3K signalling.

Accordingly, in another embodiment the present invention provides a method of identifying an agent that selectively modulates p38 signalling by TNFR1 and/or TNFR2 without substantially modulating JNK and/or ERK1/2 signalling by the receptor, the method including identifying an agent that modulates TNFR1 and/or TNFR2 signalling through a region of the receptor associated with p38 signalling and not associated with JNK and/or ERK1/2 signalling.

For example, in the case where the receptor is TNFR1, the region of the receptor may include one or more of amino acids 209 to 211 of the receptor as provided by SEQ ID NO. 1. In the case where the receptor is TNFR2, the region of the receptor may include one or more of amino acids 253 to 255 of the receptor as provided by SEQ ID NO. 2.

In another embodiment, the present invention provides a method of identifying an agent that selectively modulates JNK and/or ERK1/2 signalling by TNFR1 and/or TNFR2 without substantially modulating p38 signalling by the receptor, the method including identifying an agent that modulates TNFR1 and/or TNFR2 signalling through a region of the receptor associated with JNK and/or ERK1/2 signalling and not associated with p38 signalling.

The method of identifying an agent that modulates cell signalling in the various embodiments of the present invention may utilise a cell receptor in a cell-free in vitro system, a cell receptor present in a cell in in vitro culture, or a cell receptor present in a biological system, such as a subject.

Methods for screening agents involving the high-throughput screening of agents are specifically contemplated. For example, high throughput screening methods are as described in "High Throughput Screening" (2002) Humana Press Inc. edited by William P. Janzen.

For example, the cell receptor may be an isolated cell receptor in a cell free system that allows signalling from the receptor to be determined. In this case, exposure of the agent to the receptor can be used to determine whether the agent selectively modulates cell signalling by the receptor.

Alternatively, the cell receptor may be present in a cell in vitro. For example, the cell receptor may be an endogenous receptor present in a cell, or an exogenous receptor introduced into the cell.

In the case of TNFR1 or TNFR2, suitable cells for use in the methods of identification in the various forms of the present invention include endothelial cells and neutrophils. Exogenous receptors may be introduced into the cells by a method known in the art. Methods for determining whether an agent selectively modulates cell signalling are known in the art.

In the case of a cell receptor present in an entire subject, a suitable animal system for identifying the agent is a mouse or rodent. Transgenic animals may be produced for studying the effects of non-naturally occurring receptors by a method known in the art. Methods for determining whether an agent selectively modulates signalling in an animal are known in the art.

The present invention also provides an agent identified by the various methods of identification of the present invention. Such agents may be agonists or antagonists of one or more signalling pathways, and are candidates as therapeutic agents.

For example, in the case of TNF receptors, the present invention also provides the use of such agents in the preparation of a medicament for preventing and/or treating one or more of the various diseases, condition and states described previously herein, including for example infection by a virus, infection by a pathogen, cancer, an inflammatory disease, cell or tissue rejection, asthma, an allergic reaction, atherosclerosis, diabetes (Type I and Type II, and complications thereof including nephropathy, neuropathy, retinopathy, and cardiovascular disease), cystic fibrosis, rheumatoid arthritis, sepsis, pain, p38-mediated diseases, conditions or states, Il-1 mediated diseases, conditions and states, TNF-mediated diseases, conditions and states, and IL-8 mediated diseases, conditions and states.

The method of identification may also be used to identify an agent that selectively modulates a biological response of interest in a cell, biological system or an entire subject.

Accordingly, in another embodiment the present invention also provides a method of identifying an agent that selectively modulates a biological response of interest produced by signalling through a cell receptor involved in signalling through multiple signalling pathways, the method including identifying an agent that selectively modulates the biological response of interest by signalling through one or more specific signalling pathways and which does not substantially modulate one or more other biological responses produced by signalling through the one or more other signalling pathways.

In the case of TNFR1 or TNFR2, in one embodiment the agent may selectively modulate p38 signalling and/or NFκB signalling upon binding of TNF-α to a TNFR1 or TNFR2, without substantially modulating one or more of the JNK, ERK1/2, and PI3K signalling pathways.

For example, the method may be used to identify an agent that selectively modulates a biological response of interest produced by activation of p38 signalling and/or NFκB signalling and which does not substantially modulate one or more other biological responses produced by signalling through one or more of the JNK, ERK1/2, and PI3K signalling pathways.

In another embodiment, the method may be used to identify an agent that selectively modulates a biological response of interest produced by inhibition of p38 signalling and/or NFκB signalling and which does not substantially modulate one or more other biological responses produced by signalling through one or more of the JNK, ERK1/2, and PI3K signalling pathways.

Alternatively, the agent may selectively modulate one or more of JNK, ERK1/2, and PI3K signalling upon binding of TNF-α to a TNFR1 or TNFR2, without substantially modulating the p38 and/or NFκB signalling pathways.

For example, the method may be used to identify an agent that selectively modulates a biological response of interest produced by activation of one or more of JNK, ERK1/2, and PI3K signalling and which does not substantially modulate one or more other biological responses produced by signalling through the p38 and/or NFκB signalling pathways.

Alternatively, the method may be used to identify an agent that selectively modulates a biological response of interest produced by inhibition of one or more of JNK, ERK1/2, and PI3K signalling and which does not substantially modulate one or more other biological responses produced by signalling through the p38 and/or NFκB signalling pathways.

As discussed previously herein, the method of identification may include identifying an agent that modulates signalling through a region of the receptor that is involved in selective modulation of the one or more signalling pathways. In the case of TNFR1 or TNFR2, the agent may for example modulate TNFR1 or TNFR2 signalling through a region of the receptor associated with p38 and/or NFκB signalling and not associated with one or more of JNK, ERK1/2 and PI3K signalling.

In the case where the receptor is TNFR1, the region of the receptor includes one or more of amino acids 209 to 211 of the receptor as provided by SEQ ID NO. 1.

In the case where the receptor is TNFR2, the region of the receptor includes one or more of amino acids 253 to 255 of the receptor as provided by SEQ ID NO. 2.

The biological response of interest are as previously discussed herein, for example, one or more of immunity against infection by a virus or a pathogen, phagocyte and/or natural killer cell killing of tumour cells, activation of immune function, suppression of immune function, sepsis and leukocyte activation.

For example, the biological response of interest may be associated with activation of p38 signalling through the TNF receptor, such as immunity against infection and/or killing of tumour cells.

In one embodiment, the one or more other biological responses is a pathogenetic response associated with activation of JNK and/or ERK1/2 signalling through the TNF receptor.

In another embodiment, the present invention also provides a method of identifying an agent that modulates p38 signalling by a TNF receptor, the method including:
(i) identifying an agent that interacts with a region of TNFR1 that includes one or more of amino acids 209 to 211 of SEQ ID NO. 1 and/or identifying an agent that interacts with a region of TNFR2 that includes one or more of amino acids 253 to 255 of SEQ ID NO.2;
(ii) determining the ability of the agent so identified to modulate p38 signalling by a TNF receptor; and
(iii) identifying the agent as an agent that modulates p38 signalling by the TNF receptor.

In one embodiment, the TNF receptor is TNFR1 or TNFR2.

The method may be used to identify an agent that activates or inhibits p38 signalling by the receptor.

For example, the method may be used to identify an agent that activates p38 signalling and does not substantially activate one or more of JNK, ERK1/2 and PI3K signalling by the receptor, or alternatively, inhibits p38 signalling and does not substantially inhibit one or more of JNK, ERK1/2 and PI3K signalling by the receptor.

As discussed previously herein, the present invention may also be used to identify an agent that modulates signalling by a receptor, by identifying agents that interact with the receptor and/or have the ability to modulate binding of other molecules to the receptor.

Accordingly, in another embodiment the present invention provides a method of identifying an agent that modulates signalling by a cell receptor, the method including:
(i) identifying an agent that interacts with a region of the receptor that is involved in selective modulation of signalling by the receptor; and/or
(ii) identifying an agent that modulates interaction of a molecule to a region of the receptor that is involved in selective modulation of signalling by the receptor;
(iii) determining the ability of the agent to modulate signalling by the receptor; and
(iv) identifying the agent as an agent that modulates signalling by the receptor.

In one embodiment, the cell receptor is a cell surface molecule, such as a cytokine receptor.

Examples of cytokine receptors include Hematopoetin Receptor, including IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, CD4, IL-17 receptor, IL-17E receptor, IL-19 receptor, IL-21 receptor, IL-22 receptor, GMCSF receptor, GCSF receptor, EPO receptor, LIF receptor, OSM receptor I, OSM receptor II, and CNTF receptor; an Interleukin-1 Receptor, including IL-1RI, IL-1RII, ST2, IL-18 receptor, IL-1Rrp2, TIGGR-1, IL1RAPL, Toll-1, Toll-2, Toll-3, Toll-4, Toll-5, Toll-6, Toll-7, Toll-9; and TNF receptors.

In one embodiment, the cell receptor is a TNF receptor.

Accordingly, in another embodiment the present invention provides a method of identifying an agent that modulates signalling by a TNF receptor, the method including:
(i) identifying an agent that interacts with a region of the receptor that is involved in selective modulation of signalling by the receptor; and/or
(ii) identifying an agent that modulates binding of a molecule to a region of the receptor that is involved in selective modulation of signalling by the receptor;
(iii) determining the ability of the agent to modulate signalling by the TNF receptor; and
(iv) identifying an agent that modulates signalling by the TNF receptor.

The present invention also provides an agent identified by the method of identification of the present invention. Such agents may be for example agonists or antagonists of one or more signalling pathways.

Methods for determining whether a molecule interacts with a receptor, or displaces another molecule from a receptor, are known in the art, for example as described in "Protein-Ligand Interactions" (2003) Wiley-VCH Verlag GmbH & Co edited by H-J. Bohm et al.

Methods for determining the ability of an agent to modulate signalling by a receptor are known in the art.

As discussed previously herein, the TNF receptor may be selected from one of the receptors in the group consisting of TNFR1, TNFR2, LTβR, HVEM, CD27, 4-1BB, FAS, OX40, SITR, DR3, CD30, TRAIL-R1, TRAIL-R2, TRAIL-R3, TRAIL-R4, RANK, BAFFR, TACI, BCMA, Fn14, CD40, EDAR, XEDAR, DR6, RELT, NGFR, and TROY. In one embodiment, the TNF receptor is TNFR1 or TNFR2.

In one embodiment, identifying an agent that interacts with a region of the receptor that is involved in selective modulation of signalling by the receptor includes identifying an agent that that interacts with a region of TNFR1 that includes one or more of amino acids 209 to 211 of SEQ ID NO.1.

The step of identifying an agent that interacts with a region of the receptor that is involved in selective modulation of signalling by the receptor may also include identifying an agent that interacts with a region of TNFR2 that includes one or more of amino acids 253 to 255 of SEQ ID NO.3.

In one embodiment, the step of identifying an agent that modulates binding of a molecule to a region of the receptor that is involved in selective modulation of signalling by the receptor includes identifying an agent that modulates binding of a ligand of the TNF receptor to a region that is involved in selective modulation of signalling.

In the case of TNFR1 and TNFR2, in one embodiment the ligand is TNF-α, or a variant or fragment thereof.

Accordingly, the method of identification may include identifying an agent that modulates binding of TNF-α (or a variant or fragment thereof) to a region of TNFR1 and/or TNFR2 receptor that is involved in selective modulation of signalling by the receptor.

In one embodiment, the step of identifying an agent that modulates binding of a molecule to a region of the receptor that is involved in selective modulation of signalling by the receptor includes identifying an agent that modulates binding of a molecule that includes an amino acid sequence of SEQ ID NO.3, or variant thereof, to the TNF receptor.

In another embodiment, the step of identifying an agent that modulates binding of a molecule to a region of the receptor that is involved in selective modulation of signalling by the receptor includes identifying an agent that modulates binding of a molecule that includes an amino acid sequence of SEQ ID NO.4, or a variant thereof, to the TNF receptor.

In another embodiment, the step of identifying an agent that modulates binding of a molecule to a region of the receptor that is involved in selective modulation of signalling by the receptor includes identifying an agent that modulates binding of a molecule that includes an amino acid sequence of SEQ ID NO.5, or a variant thereof, to the TNF receptor.

In one embodiment, the agent may inhibit interaction of the molecule with the receptor.

In another embodiment, the agent may displace the molecule bound to the receptor.

In the case of a TNF receptor, in one embodiment the agent modulates one or more of the p38, JNK, and ERK1/2 signalling pathways.

Accordingly, in another embodiment the present invention provides a method of identifying an agent that modulates one or more of p38, JNK and ERK1/2 signalling by a TNF receptor, the method including:

(i) identifying an agent that interacts with a region of TNFR1 that includes one or more of amino acids 209 to 211 of SEQ ID NO.1; and/or
(ii) identifying an agent that interacts with a region of TNFR2 that includes one or more of amino acids 253 to 255; and/or
(iii) identifying an agent that modulates interaction of a molecule that includes an amino acid sequence of SEQ ID NO.3, or a variant thereof, with the TNF receptor; and/or
(iv) identifying an agent that modulates interaction of a molecule that includes an amino acid sequence of SEQ ID NO.4, or a variant thereof, with the TNF receptor; and/or
(v) identifying an agent that modulates interaction of a molecule that includes the amino acid sequence of SEQ ID NO.5 or a variant thereof, with the TNF receptor;
(vi) determining the ability of the agent to modulate one or more of p38, JNK and ERK1/2 signalling by the TNF receptor; and
(vii) identifying an agent that modulates one or more of p38, JNK and ERK1/2 signalling by the TNF receptor.

For example, the ability of an agent to prevent the binding of Peptide A (SEQ ID NO.4) and/or Peptide B (SEQ ID NO.5), or the ability of an agent to displace Peptide A or Peptide B from the receptor, may be used in a cell-based screen to determine whether the agents have the ability to modulate one or more of p38, JNK and ERK1/2 signalling by TNF receptor, and thus identify agents that are specific agonists or antagonists of the p38, JNK and/or ERK1/2 signalling pathways.

The identification may utilize for example high throughput methods for screening, as discussed previously herein.

The present invention also provides an isolated and/or modified cell receptor, wherein the receptor selectively modulates signalling through one or more signalling pathways.

This embodiment of the present invention is directed to receptors that have been engineered or modified so as to selectively modulate one or more signalling pathways without substantially modulating one or more other signalling pathways. For example, the receptor may be a recombinant form of a naturally occurring receptor, such as a variant of a naturally occurring receptor.

Methods for altering polypeptides and proteins are known in the art, for example as described in Sambrook, J, Fritsch, E. F. and Maniatis, T. Molecular Cloning: A Laboratory Manual 2nd. ed. Cold Spring Harbor Laboratory Press, New York. (1989). A suitable method is by obtaining a nucleic acid encoding the receptor and manipulating the nucleic acid by recombinant DNA technology to produce a protein with a desired amino acid sequence.

In this regard, the term "isolated" is understood to mean an entity, for example a polypeptide, nucleic acid, or a cell, which is removed from its natural environment. In the case of receptor, the receptor may be isolated, for example, by purification or the cloning of the receptor and its expression in another cell type.

Methods for purifying polypeptides and proteins are known in the art.

For example, nucleic acids encoding the receptors may be cloned into a suitable vector and the encoded protein expressed in a suitable organism and purified. Methods for the isolation of nucleic acid sequences and their cloning into a suitable expression vector are described in Sambrook, J, Fritsch, E. F. and Maniatis, T. Molecular Cloning: A Laboratory Manual 2nd. Ed. Cold Spring Harbor Laboratory Press, New York. (1989).

In one embodiment, the isolated and/or modified receptor is a human or animal receptor.

The receptor may be an isolated receptor in vitro, or a receptor present in a cell, including a cell in in vitro tissue culture, a cell in a biological system or a cell in an entire subject. The receptor may be a variant of an endogenous receptor, engineered or modified so as to selectively modulate signalling. Alternatively, the receptor may be an exogenous receptor that selectively modulates signalling.

In one embodiment, the cell receptor is a cell surface molecule, such as a cytokine receptor.

Examples of cytokine receptors include Hematopoetin Receptors such as IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, CD4, IL-17 receptor, IL-17E receptor, IL-19 receptor, IL-21 receptor, IL-22 receptor, GMCSF receptor, GCSF receptor, EPO receptor, LIF receptor, OSM receptor I, OSM receptor II, and CNTF receptor; Interleukin-1 Receptors such as IL-1RI, IL-1RII, ST2, IL-18 receptor, IL-IRrp2, TIGGR-1, IL1RAPL, Toll-1, Toll-2, Toll-3, Toll-4, Toll-5, Toll-6, Toll-7, Toll-9; and TNF receptors such as TNFR1, TNFR2, LTβR, HVEM, CD27, 4-1BB, FAS, OX40, SITR, DR3, CD30, TRAIL-R1, TRAIL-R2, TRAIL-R3, TRAIL-R4, RANK, BAFFR, TACI, BCMA, Fn14, CD40, EDAR, XEDAR, DR6, RELT, NGFR, and TROY.

In one embodiment, the isolated or modified cell receptor is TNFR1 or TNFR2. The amino acid sequences of the human receptors are provided in accession number P19438 for hTNFR1 (SEQ ID NO. 1), and accession number P20333 for hTNFR2 (SEQ ID NO:2).

In this case, the isolated or modified receptor may, for example, modulate p38 and/or NFκB signalling and not substantially modulate one or more of JNK, ERK1/2 and PI3K signalling, upon binding of TNF-α to the receptor.

For example, in one embodiment the isolated or modified receptor activates p38 and/or NFκB signalling and does not substantially activate one or more of JNK, ERK1/2 and PI3K signalling, upon binding of TNF-α to the receptor.

In another embodiment, the receptor modulates one or more of JNK, ERK1/2 and PI3K signalling and not substantially modulate p38 and/or NFκB signalling, upon binding of TNF-α to the receptor.

For example, the receptor may activate one or more of JNK, ERK1/2 and PI3K signalling and not substantially activate p38 and/or NFκB signalling, upon binding of TNF-α to the receptor.

In another embodiment, the present invention also provides a nucleic acid encoding a receptor according to the various forms of the present invention, and a cell including these nucleic acids. Methods for isolating and manipulation nucleic acids are known in the art, for example, as described in described in Sambrook, J, Fritsch, E. F. and Maniatis, T. Molecular Cloning: A Laboratory Manual 2nd. ed. Cold Spring Harbor Laboratory Press, New York. (1989).

In this regard, the accession number for the nucleotide sequence encoding human TNFR1 is NM_001065. The accession number for the nucleotide sequence encoding human TNFR2 is NM_001066.

The nucleic acid encoding the receptor may also form part of a vector. For example, the vector may be a plasmid, all or part of a viral genome, or any other nucleic acid capable of autonomous replication in a prokaryotic or eukaryotic host.

The vector may also further include regulatory elements for the expression of inserted nucleic acids, for example promoters for driving the expression of the receptor in a particular cell, poly A signals for efficient polyadenylation of mRNA transcribed from inserted nucleic acids, or other regulatory elements to control translation, transcription or mRNA stability.

The present invention also provides a prokaryotic or eukaryotic cell including the above nucleic acids.

In another embodiment, the present invention provides a receptor consisting of:
(i) amino acids 209 to 211 as provided in SEQ ID NO. 1, and/or or amino acids 253 to 255 of the receptor as provided in SEQ ID NO. 2, or a variant thereof;
(ii) a transmembrane domain; and
(iii) all or part of a cytoplasmic domain of a receptor, or a functional variant thereof, the all or part of the cytoplasmic domain sufficient to mediate signalling through one or more of the p38, NFκB, JNK and ERK1/2 pathways; and wherein the isolated receptor optionally includes one or more exogenous amino acids.

The receptor may be an isolated receptor. In one embodiment, the receptor is present in a cell.

A receptor of this form retains the ability to activate the p38 signalling pathway upon binding of TNF-α. An example of such a receptor is TNFR1 with the four cysteine rich domains deleted.

The truncated receptor according to this embodiment of the present invention may also optionally include one or more exogenous amino acids. In this case, the term "exogenous amino acids" includes one or more amino acids that are not present at a particular position in the naturally occurring receptor from which the truncated receptor is derived. For example, the receptor may have an amino and/or carboxy terminal fusion of non-receptor derived amino acids, and/or the insertion of one or more amino acids in the region between amino acid 211/253 and the transmembrane domain, and/or the insertion of one or more amino acids in the region between the transmembrane domain and the cytoplasmic domain.

In one embodiment, the receptor is a TNF receptor with all four of the cysteine rich domains deleted.

Accordingly, in another embodiment the present invention provides a TNF receptor with the four cysteine rich domains deleted, wherein the receptor has the ability to signal through one or more of the p38, NFκB, JNK and ERK1/2 pathways, and receptor optionally includes one or more exogenous amino acids.

It will be appreciated that the truncated receptors described above may include a transmembrane domain derived from a TNF receptor, or a transmembrane domain derived from (i) another receptor; or (ii) another molecule; or (ii) be a synthetic transmembrane domain.

In one embodiment, the transmembrane is derived from either TNFR1 or TNFR2,

The cytoplasmic domain is any domain that is capable of mediating signalling through one or more of the p38, NFκB, JNK and ERK1/2 pathways, and as such may be derived from TNFR1 or TNFR2, another receptor, or be a synthetic domain. In one embodiment, the cytoplasmic domain is derived from TNFR1 or TNFR2.

Methods for the constructions and expression of recombinant molecules are as previously described herein.

In one embodiment, the receptor is a truncated TNFR1.

Accordingly, in another embodiment the present invention provides a TNF receptor-1, wherein the receptor consists of:
(i) amino acids 209 to 211 of the receptor as provided in SEQ ID NO. 1, or a functional variant thereof,
(ii) a transmembrane domain; and
(iii) all or part of the cytoplasmic domain of the receptor, or a functional variant thereof, the all or part of the cytoplasmic domain sufficient to mediate signalling through one or more of the p38, NFκB, JNK and ERK1/2 pathways; and wherein the isolated receptor optionally includes one or more exogenous amino acids.

In another embodiment, the receptor is a truncated TNFR2.

Accordingly, in another embodiment the present invention provides a TNF receptor-2, wherein the receptor consists of:
(i) amino acids 253 to 255 of the receptor as provided in SEQ ID NO. 2, or a functional variant thereof;
(ii) a transmembrane domain; and
(iii) all or part of the cytoplasmic domain of the receptor, or a functional variant thereof, sufficient to mediate signalling through one or more of the p38, NFκB, JNK and ERK1/2 pathways; and wherein the isolated receptor optionally includes one or more exogenous amino acids.

The present invention also provides an isolated or modified receptor as herein previously described when used as a target to identify an agent that selectively modulates signalling through one or more signalling pathways.

In the case of TNFR1 and TNFR2, the receptor may be used as a target to identify an agent that selectively modulates p38 and/or NFκB signalling upon binding of TNF-α to a TNFR1 or TNFR2.

For example, the receptor may be used as a target to identify an agent to prevent and/or treat a disease, condition or state in a subject requiring administration to the subject of an agent that activates or inhibits p38 signalling.

In another embodiment, the receptor may be used as a target to identify an agent that selectively activates or inhibits JNK and/or ERK1/2 signalling by a TNF receptor.

For example, the receptor may be used as a target to identify an agent to prevent and/or treat a disease, condition or state in a subject requiring administration to the subject of an agent that activates JNK and/or ERK1/2 signalling.

Such diseases, conditions and states are as previously herein described.

The present invention also provides an antagonist of a ligand of cell receptor, wherein the antagonist includes or mimics a region of the receptor that is involved with selective modulation of one or more signalling pathways controlled by the receptor upon binding of the ligand to the receptor.

Such antagonists may be used to inhibit signalling through a receptor upon ligand binding to the receptor, by exposing the receptor to the antagonist.

Examples of antagonists in the various relevant embodiments of the present invention include peptide-based antagonists (such as a peptide, a polypeptide, a protein, an enzyme, an antibody or a part thereof, or a molecule including a peptide) and non-peptide based antagonists (such as small molecule, a nucleic acid, an oligonucleotide, a polysaccharide, a glycoprotein, a lipid, and an aptamer). The antagonists may be produced by a method known in the art.

In one embodiment, the antagonist in the various relevant embodiments of the present invention is a soluble antagonist. Generally, the antagonist may have a size of equal to or less than 10 kD, and typically are less than 2 kD and usually less than 1 kD in size.

In one embodiment, the antagonist is an antagonist of a ligand of a cell surface molecule, such as a cytokine receptor.

Examples of cytokine receptors include Hematopoetin Receptors such as IL-2 receptor, IL-3 receptor, IL-4 receptor, IL-5 receptor, IL-6 receptor, IL-7 receptor, IL-9 receptor, IL-10 receptor, IL-11 receptor, IL-12 receptor, IL-13 receptor, IL-15 receptor, CD4, IL-17 receptor, IL-17E receptor, IL-19 receptor, IL-21 receptor, IL-22 receptor, GMCSF receptor, GCSF receptor, EPO receptor, LIF receptor, OSM receptor I, OSM receptor II, and CNTF receptor; Interleukin-1 Receptors such as IL-1RI, IL-1RII, ST2, IL-18 receptor, IL-IRrp2, TIGGR-1, IL1RAPL, Toll-1, Toll-2, Toll-3, Toll-4, Toll-5, Toll-6, Toll-7, Toll-9; and TNF receptors such as TNFR1, TNFR2, LTβR, HVEM, CD27, 4-1BB, FAS, OX40, SITR, DR3, CD30, TRAIL-R1, TRAIL-R2, TRAIL-R3, TRAIL-R4, RANK, BAFFR, TACI, BCMA, Fn14, CD40, EDAR, XEDAR, DR6, RELT, NGFR, and TROY.

Ligands of the above receptors are known in the art. Cytokine receptors and their ligands are for example as described in "Cytokines and Cytokine Receptors-Physiology and Pathological Disorders" (2000) ed. By C. A. Bona and J-P. Revillard OPA N.V.

In one embodiment, the cell receptor is TNFR1 or TNFR2. In this case, the antagonist may be an antagonist of a ligand of either or both of these receptors, such as TNF-α.

Accordingly, in another embodiment the present invention provides a TNF-α antagonist, wherein the antagonist includes or mimics a region of a TNF receptor that is involved with selective modulation of one or more signalling pathways controlled by the receptor upon binding of TNF-α to the receptor.

Such antagonists may be used to inhibit signalling through one or more pathways controlled by a receptor upon binding of a ligand to the receptor.

In one embodiment, the antagonist includes or mimics a region of a TNFR1 or TNFR2 receptor that is involved with selective modulation of p38 and/or NFκB signalling by the receptor. For example, the antagonist may include or mimic a region of the receptor that is involved with selective activation of p38 and/or NFκB signalling by the receptor.

This antagonist may further include or mimic a region that is not involved with selective modulation of one or more of JNK, ERK1/2 and a PI3K signalling. For example, the antagonist may include or mimic a region that is not involved with selective activation of one or more of JNK, ERK1/2 and a PI3K signalling.

These antagonists inhibit p38 and/or NFκB signalling by the TNF receptor upon binding of TNF-α to the receptor.

In one embodiment, the antagonist may include an amino acid sequence according to any one or more of SEQ ID NO.6, SEQ ID NO.7, SEQ ID NO.8, SEQ ID NO.9 and SEQ ID NO.10, or a variant of any of these sequences.

For example, the antagonist may be selected from the following peptides: Gly-Thr-Thr-OH (SEQ ID NO.6), Leu-Lys-Pro-Gly-Thr-Thr (SEQ ID NO.7), His$_6$-Leu-Lys-Pro-Gly-Thr-Thr (SEQ ID NO.8), Gly-Thr-Glu-Asp-Ser-Gly-Thr-Thr-Val (SEQ ID NO.9) and Glu-Asp-Ser-Gly-Tlir-Thr (SEQ ID NO.10), or a variant of any of these sequences.

In another embodiment, the present invention provides a peptide selected from the group consisting of H-Gly-Thr-Thr-OH ("Peptide M4-2"; SEQ ID NO.6), H-Leu-Lys-Pro-Gly-Thr-Thr-OH ("Peptide "M4-1"; SEQ ID NO.7), His$_6$-Leu-Lys-Pro-Gly-Thr-Thr-OH ("Histisine tag M4"; SEQ ID NO.8), and Gly-Thr-Glu-Asp-Ser-Gly-Thr-Thr-Val (SEQ ID NO.9) and Glu-Asp-Ser-Gly-Thr-Thr (SEQ ID NO.10), or a variant of any of these sequences. In one embodiment, the peptide is an isolated peptide. These peptides are inhibitors of TNF.

In the case of an antagonist that inhibits p38 signalling, the antagonist may not include an amino acid sequence from one or more cysteine rich domains from a TNF receptor.

In another embodiment, the antagonist includes or mimics a region of the receptor that is involved with selective modulation of one or more of JNK, ERK1/2 and PI3K signalling by the receptor.

For example, the antagonist may include or mimic a region of the receptor that is involved with selective activation of JNK, ERK1/2 and PI3K signalling by the receptor.

This antagonist may further include or mimic a region that is not involved with selective modulation of p38 and/or NFκB signalling.

In one embodiment, the antagonist is a soluble antagonist.

In another embodiment, the antagonist is a non-peptidyl compound.

These antagonists may inhibit one or more of JNK, ERK1/2 and PI3K signalling by the TNF receptor upon binding of TNF-α to the receptor.

The present invention also provides a pharmaceutical composition including the antagonist according to the various embodiments of the present invention. Examples of the formulation of pharmaceutical compositions are as previously herein described.

The antagonists may also be used to prevent and/or treat a disease, condition or state in a subject that would benefit from modulation of receptor signalling.

In this regard, the p38 antagonists may also be used to prevent and/or treat a disease, condition or that would benefit from inhibition of p38 signalling from a TNF receptor and/or a disease, condition or state associated with undesired activation of p38 signalling by a TNF receptor, by administering to the subject an effective amount of the antagonist.

Examples of diseases, conditions or states is one or more of infection by a virus, infection by a pathogen, cancer, an inflammatory disease, asthma, an allergic reaction, atherosclerosis, diabetes, and pain.

The present invention also provides the use of a p38 antagonist in the preparation of a medicament for preventing and/or treating a disease, condition or state associated with undesired activation of p38 signalling by a TNF receptor and/or for use in the preparation of a medicament for preventing and/or treating a disease, condition or state that would benefit from inhibition of p38 signalling.

The JNK and/or ERK1/2 antagonists may also be used to prevent and/or treat a disease, condition or state in a subject that would benefit from inhibition of one or more JNK, ERK1/2 and PI3K signalling from a TNF receptor and/or a disease, condition or state associated with undesired activation of one or more of JNK, ERK1/2 and PI3K signalling by a TNF receptor, by administering to the subject an effective amount of an antagonist.

The present invention also provides the use of JNK and/or ERK1/2 antagonist in the preparation of a medicament for preventing and/or treating a disease, condition or state associated with undesired activation of one or more of JNK, ERK1/2 and PI3K signalling by a TNF receptor and/or for use in the preparation of a medicament for preventing and/or treating a disease, condition or state that would benefit from inhibition of one or more of JNK, ERK1/2 and PI3K signalling.

The present invention also provides a soluble TNF-α antagonist including all or part of SEQ ID NO.1 and/or SEQ ID NO.2. Such antagonists inhibit p38 signalling by a TNF receptor upon binding of TNF-α to the receptor.

Such antagonists may also used to inhibit p38 signalling through a TNF receptor upon TNF-α binding to the TNF receptor, by exposing the TNF receptor to the antagonist.

In one embodiment, the antagonist includes an amino acid sequence selected from the group consisting of H-Gly-Thr-Thr-OH (SEQ ID NO.6), H-Leu-Lys-Pro-Gly-Thr-Thr-OH (SEQ ID NO.7), His6-Leu-Lys-Pro-Gly-Thr-Thr-OH (SEQ ID NO.8), and Gly-Thr-Glu-Asp-Ser-Gly-Thr-Thr-Val (SEQ ID NO.9) and H-Glu-Asp-Ser-Gly-Thr-Thr-OH (SEQ ID NO.10), or variants of any of these sequences.

Examples of suitable antagonists include a peptide selected from the group consisting of H-Gly-Thr-Thr-OH (SEQ ID NO.6), H-Leu-Lys-Pro-Gly-Thr-Thr-OH (SEQ ID NO.7), His 6-Leu-Lys-Pro-Gly-Thr-Thr-OH (SEQ ID NO.8), and Gly-Thr-Glu-Asp-Ser-Gly-Thr-Thr-Val (SEQ ID NO.9) and H-Glu-Asp-Ser-Gly-Thr-Thr-OH (SEQ ID NO.10), or a variant of any of these sequences.

In one embodiment, the antagonist does not include an amino acid sequence from one or more cysteine rich domains from a TNF receptor.

In one embodiment, the TNF receptor is TNFR1 or TNFR2.

Methods for producing antagonists are known in the art. For example, in the case of a peptide antagonist, the antagonist may be synthesized by a suitable method known in the art.

The present invention also provides a pharmaceutical composition including the antagonist. Examples of the formulation of pharmaceutical compositions are as previously herein described.

The antagonists may also be used to prevent and/or treat a disease, condition or state in a subject that would benefit from modulation of receptor signalling.

In another embodiment, the present invention also provides an isolated peptide selected from the group consisting of Gly-Thr-Thr (SEQ ID NO.8), Leu-Lys-Pro-Gly-Thr-Thr (SEQ ID NO.9), $His_6$-Leu-Lys-Pro-Gly-Thr-Thr (SEQ ID NO.10), and Gly-Thr-Glu-Asp-Ser-Gly-Thr-Thr-Val (SEQ ID NO.11) and Glu-Asp-Ser-Gly-Thr-Thr (SEQ ID NO.12), or a variant thereof.

Methods are known in the art for producing peptides.

The peptides may also be used to prevent and/or treat a disease, condition or state in a subject that would benefit from modulation of receptor signalling.

The present invention also provides an agonist of a ligand of a cell receptor, wherein the agonist includes or mimics a region of the receptor that is involved with selective modulation of one or more signalling pathways controlled by the receptor upon binding of the ligand to the receptor.

In one embodiment, the cell receptor is a cytokine receptor. Examples of cytokine receptors are as previously discussed herein.

In one embodiment, the cytokine receptor is a TNF receptor, such as TNFR1 or TNFR2.

In one embodiment, the agonist includes or mimics a region of the receptor that is involved with selective modulation of p38 and/or the NFκB signalling by the receptor.

In another embodiment, the agonist includes or mimics a region that is involved with selective modulation of one or more of JNK, ERK1/2 and a PI3K signalling.

In one embodiment, the agonist includes an amino acid sequence according to SEQ ID NO:6, or a variant thereof.

In another embodiment the agonist is a non-peptidyl compound, including a mimetic of SEQ ID NO.6.

The present invention also provides a pharmaceutical composition including the agonist, and the use of an agonist to prevent and/or treat a disease, condition or state. Examples of diseases, conditions or states are as previously discussed herein.

The present invention also provides a method of preventing and/or treating a disease, condition or state in a subject that would benefit from inhibition of p38 signalling from a TNF receptor and/or a disease, condition or state associated with undesired activation of p38 signalling by a TNF receptor, by administering to the subject an effective amount of such a soluble TNF-α antagonist.

Examples of such diseases, conditions or states include infection by a virus, infection by a pathogen, cancer, an inflammatory disease, asthma, an allergic reaction, atherosclerosis, diabetes, and pain.

The present invention also provides the use of such an antagonist in the preparation of a medicament for preventing and/or treating a disease, condition or state in a subject that would benefit from inhibition of p38 signalling from a TNF receptor and/or for preventing and/or treating a disease, condition or state associated with undesired activation of p38 signalling by a TNF receptor.

Therapeutic delivery of biolomolecules is generally as described in Bladon, C. (2002) "Pharmaceutical Chemistry: Therapeutic Aspects of Biomolecules" John Wiley & Sons Ltd.

Viral and gene therapy techniques are as generally described in "Viral Vectors for Gene Therapy: Methods and Protocols" Edited by Jules G Constant, Curtis A Machida (2003) Humana Press Inc., "Gene Delivery to Mammalian Cells: Viral Gene Transfer Techniques" Edited by William C Heiser (2004) Humana Press Inc., "Viruses in Human Gene Therapy" Edited by J. H. Vos (1995) Carolina Academic Press, and "Viral Therapy Of Human Cancers" Edited by J. G. Sinkovics and J. C. Horwath (2005) Marcel Dekker.

Finally, standard techniques may be used for recombinant DNA technology, oligonucleotide synthesis, and tissue culture and transfection (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989) and Ausubel, F. M. et al. (1989) Current Protocols in Molecular Biology, John Wiley & Sons, New York, N.Y.

DESCRIPTION OF SPECIFIC EMBODIMENTS

Reference will now be made to experiments that embody the above general principles of the present invention. However, it is to be understood that the following description is not to limit the generality of the above description.

Example 1

Materials

RPMI 1640, DMEM, PBS and HBSS were obtained from Cell Image, Women's and Children's Hospital, (Adelaide, South Australia). Gelatin and FCS were purchased from MultiSer, Biosciences Pty Ltd, Australia. Bis-N-methylacridinium nitrate (lucigenin), formyl-methionyl-leucyl-phenylalanine (fMLP), myelin basic protein, protein A-sepharose and general reagents for kinase assays were from Sigma Chemical Company, (St Louis, Mo.). γ-32P ATP (specific activity 4000 Ci/mmol) was obtained from Geneworks, (Adelaide, South Australia). Glutathione-sepharose was from Pharmacia Biotech, Sydney, Australia. Anti-p38 (C-20), anti-ERK2 (C-14), anti-KHS(C-20) (kinase homologous to SPS1/STE20, also known as germinal center kinase related, GCKR), anti-ASK1 (apoptosis signal regulating kinase 1) anti-phospho-JNK and anti-NFkB p65 (C-20) antibodies were obtained from Santa Cruz Biotech, (California, USA). Anti-ACTIVE ERK antibody was purchased from Promega Corp (Madison, Wis.). Anti-human E-selectin antibody was obtained from Becton Dickinson and Co., (San Jose, Calif.). Horseradish peroxidase-conjugated anti-rabbit immunoglobulin G antibody was obtained from Dakopatts, (Copenhagen, Denmark). LipofectAMiNE 2000 was obtained from Invitrogen Australia Pty Lid (Mount Waverely, Victoria, Australia). The p38 inhibitor, SB205580 was purchased from Biomol Research Labs (Plymouth Meeting, Pa.).

Human recombinant TNF was produced by Genentech, Inc. (San Francisco, Calif.), and was kindly provided by Dr. G. R. Adolf (Ernst-Boehringer Ingelheim Institut, Vienna, Austria) (7) and $TNF_{70-80}$ and the control peptide code 205, H-Gly-Gly-Asp-Pro-Gly-Ile-Val-Thr-His-Ser-OH were synthesised by Auspep Pty Ltd, Melbourne, Victoria. While it is difficult to directly equate the TNF activity to $TNF_{70-80}$ because of the lack of tumor cell cytotoxicity of this peptide, previous comparisons on their ability to stimulate nitric oxide production in macrophage show that 5.0 μg/ml of $TNF_{70-80}$ equates to 1000 U/ml of TNF.

Example 2

Cells (i) Neutrophils

Neutrophils were prepared from peripheral blood of healthy donors by a rapid single-step technique (Kumaratilake, L. M., Rathjen, D. A., Mack, P., Widmer, F., Prasertsiriroj, V., and Ferrante, A. (1995) *J. Clin. Invest.* 95: 2315-2323) using Hypaque-Ficoll and according to the institution's guidelines on human ethics. The preparations of neutrophils were routinely of >99% viability and >98% purity. These were either used as cells in suspension or as adhered neutrophils by adding the cells to plasma coated plates as previously described (Powell, W., Gravel, S., Halwani, F., Hii, C. S., Huang, Z. H., Tan, A. M., and Ferrante, A. (1997) *J. Immunol.* 159: 2952-2959).

(ii) Endothelial Cells

Fresh human umbilical cords were obtained from consenting mothers according to the institution's guidelines on human ethics. Umbilical vein endothelial cells (HUVEC) were obtained by collagenase digestion and maintained in RPMI-1640 containing 20% human AB serum, 3.2 mmol/L L-glutamine, 80 U/ml penicillin and 80 μg/ml streptomycin) on gelatin-coated dishes (Huang, Z. H., Bates, E. J., Fenrante, J. V., Hii, C. S., Poulos, A., Robinson, B. S., and Ferrante, A. (1997) *Circ. Res.* 80: 149-158).

(iii) HEK 293T

HEK 293T cells were obtained from the American Type Culture Collection and maintained in DMEM, supplemented with 10% fetal calf serum. Cells, stably transfected with pRK5-TRAF2-FLAG, pRK5-TRAF287-501-FLAG (Dr. V. Dixit, Genentech Inc., South San Francisco) or an empty plasmid using LipofectAMINE 2000, were obtained from Dr P Xia, Hanson Institute, Adelaide, Australia) (Xia, P., Wang, L., Moretti, P. A., Albanese, N., Chai, F., Pitson, S. M., D'Andrea, R. J., Gamble, J. R., and Vadas, M. A. (2002) *J. Biol. Chem.* 277: 7996-8003).

Example 3

Transfection of 70Z/3 Cells with hTNFR1DNA

70Z/3 cells, kindly provided by W. Langdon, University of Western Australia, Perth, Australia, are mouse pre-B lymphocytes which lack binding sites for human TNF and are non-responsive to the cytokine (Kruppa G. et al. (1992) *J. Immunol.* 148: 3152-3157). The cells were maintained in RPMI-1640 medium with 4.5 g/L glucose, 2 mM L-glutamine, 50 mM 2-mercaptoethanol and 10% FCS in an atmosphere of 95% air and 5% CO2. Cells were plated onto 10 cm plates at $4 \times 10^7$ cells in 15 ml culture medium. Before performing transient transfection, plasmid DNA (hTNFR1), kindly provided by Dr M. Kronke, Institute of Medical Microbiology and Hygiene, Medical Center University of Cologne, Koln, Germany (Adam, D., Wiegmann, K., Adam-Klages, S., Ruff A., and Kronke, M. (1996) *J. Biol. Chem.* 271: 14617-22), (20

μg in 1 ml of RPMI1640) was mixed with LipofectAMINE 2000 (Invitrogen) (60 μl in 1 ml of RPMI) and the mixture were left at room temperature for 20 min. The mixture was directly added to the cells and incubated for 24 h. The cells were washed twice with HBSS before use.

Example 4

Chemiluminescence Assay

Neutrophil superoxide production was measured as the chemiluminescence generated by the reduction of lucigenin, essentially as described previously (Kumaratilake, L. M., Rathjen, D. A., Mack, P., Widmer, F., Prasertsiriroj, V., and Ferrante, A. (1995) *J. Clin. Invest.* 95: 2315-2323). Briefly, to $1 \times 10^6$ neutrophils in 400 μl of HBSS was added 100 μl of stimulus and 500 μl of 250 μg/ml of lucigenin. The chemiluminescence was measured in a luminometer (Berthold Technologies, Bad Wildbad, Germany) over a 20 min period and the data imported into Microsoft Excel (Redmond, Wash.).

Example 5

Preparation of Cell Lysates

The cells were lysed in 200 μl of buffer A (20 mM HEPES, pH 7.4, 0.5% (v/v) Nonidet P-40, 100 mM NaCl, 1 mM EDTA, 2 mM $Na_3VO_4$, 2 mM dithiotbreitol, 1 mM phenylmethylsulfonyl fluoride, and 10 μg/ml leupeptin, aprotonin, pepstatin A, and benzamidine) for 2 h at 4° C. with constant mixing (20) After centrifugation (12,000 g×5 min), the supernatants were collected and the protein content of the lysates was determined by Lowry's method of protein determination. Samples were stored at −70° C. until assayed. For Western blot analysis, samples were mixed with Laemmli buffer and boiled before being stored for subsequent electrophoresis.

Example 6

Western Blot Analysis

Western blot analysis was conducted as described previously (Hii, C. S., Huang, Z. H., Bilney, A., Costabile, M., Murray, A. W., Rathjen, D. A., Der, C. J., and Ferrante, A. (1998) *J. Biol. Chem.* 273: 19277-19282). Briefly, equal amounts of denatured protein from each lysate were separated by 12% SDS polyacrylamide gel electrophoresis (PAGE). The proteins were electrophoretically transferred to nitrocellulose membranes (Schleicher and Schuell, Keene, N. H., USA)(3 h at 40V). The amounts of dually phosphorylated ERK1 and ERK2, phospho-JNK and NFκB p65 subunit were detected using rabbit anti-active ERK, mouse anti-phospho JNK and rabbit anti-NFκB antibody, respectively. Immune complexes were visualised by enhanced chemiluminescence (Hii, C. S., Huang, Z. H., Bilney, A., Costabile, M., Murray, A. W., Rathjen, D. A., Der, C. J., and Ferrante, A. (1998) *J. Biol. Chem.* 273: 19277-19282). The blots were stripped and reprobed with anti-ERK2 or anti-JNK antibody to confirm equal loading.

Example 7

Immunoprecipitation of Signalling Molecules

Lysates containing equal amounts of protein (0.5-1 mg) were precleared with protein A sepharose (4° C.) before being incubated with anti-KHS, anti-p38, anti-ASK-1 or anti-ERK2 antibody (3 μg/sample). After mixing for 2 h (4° C.), the immune complexes were precipitated by the addition of protein A sepharose. The immunoprecipitates were collected by centrifugation (16,000 g×15s) and washed once with buffer A (4° C.), once with buffer B (10 mM Tris/HCl, pH 7.6, 100 mM NaCl, 1 mM EDTA and 100 μM $Na_2VO_4$ and once with assay buffer (Hii, C. S., Huang, Z. H., Bilney, A., Costabile, M., Murray, A. W., Rathjen, D. A., Der, C. J., and Ferrante, A. (1998) *J. Biol. Chem.* 273: 19277-19282).

Example 8

GCKR(KHS), ASK-1, p38, ERK and JNK Assays

KHS (hereon referred to as "GCKR") activity was assayed as described previously using myelin basic protein as a substrate (Shi, C. S., Leonardi, A., Kyriakis, J., Siebenlist, U., and Kerhl, J. H. (1999) *J. Immunol.* 163: 3279-3285). ASK-1 activation was determined in immunoprecipitates of ASK-1 by autophosphorylation (Kyriakis, J. M., and Auruch, J. (2001) *Physiol. Rev.* 81: 807-869). p38 and ERK activities were determined as described using myelin basic protein as a substrate (Hii, C. S., Huang, Z. H., Bilney, A., Costabile, M., Murray, A. W., Rathjen, D. A., Der, C. J., and Ferrante, A. (1998) *J. Biol. Chem.* 273: 19277-19282). We have previously demonstrated that p38 immunoprecipitation does not contain ERK1/ERK2, and ERK1/ERK2 immunoprecipitates do not contain p38. Hence, these assays detect the targeted MAP kinase. A solid phase assay using glutathione-S-transferase (GST)-conjugated-jun (1-79) was employed to assay JNK activity (Hii, C. S., Huang, Z. H., Bilney, A., Costabile, M., Murray, A. W., Rathjen, D. A., Der, C. J., and Ferrante, A. (1998) *J. Biol. Chem.* 273: 19277-19282). Phosphorylated ASK-1, myelin basic protein and GST-jun (1-79) were fractionated on 8, 16 and 12% SDS polyacrylamide gels, respectively, and the bands were detected and radioactivity determined using an Instant Imager (Packard Instruments, Canberra, Australia). Activation of ERK1/ERK2 and JNK was also investigated by Western blot analysis using the anti-active ERK and anti-phospho JNK antibodies as appropriate Example 9

Statistical Analyses

The data were analysed for significance using Dunnett's multiple comparisons test with one control, and $p<0.05$ considered significant.

Example 10

Selective Activation of p38 in Endothelial Cells by $TNF_{70-80}$ Compared to TNF We have previously shown that unlike TNF, $TNF_{70-80}$ failed to up-regulate the expression of adhesion molecules on endothelial cells (Hii, C. S., Huang, Z. H., Bilney, A., Costabile, M., Murray, A. W., Rathjen, D. A., Der, C. J., and Ferrante, A. (1998) J. Biol. Chem. 273: 19277-19282). Since JNK has previously been shown to regulate this response, we examined whether or not $TNF_{70-80}$ failed to activate this kinase. The activity of JNK in HUVEC was increased by TNF at concentrations of 100 and 1000 U/ml (FIG. 1a). Interestingly, $TNF_{70-80}$ (1-50 μM) failed to stimulate the activity of JNK in HUVEC (FIG. 1a). Under these experimental conditions, TNF (0, 100 or 1000 U/ml) but not $TNF_{70-80}$ (1-50 μM) stimulated the expression of E-selectin on endothelial cells (data not presented). Similar results were found with respect to activation of the ERKs (FIG. 1b). Thus, TNF stimulated the dual phosphorylation of the ERKs in endothelial cells (FIG. 1b). In contrast, $TNF_{70-80}$ caused only negligible phosphorylation of the ERKs in HUVEC (FIG. 1b). Both TNF and $TNF_{70-80}$ stimulated the activity of p38 in HUVEC (FIG. 1c). The control peptide, 205, failed to stimulate p38 in these cells.

Example 11

Activation of p38 in Neutrophils by $TNF_{70-80}$

While neither TNF nor $TNF_{70-80}$ stimulated the activity of either JNK or ERK in neutrophils in suspension (FIGS. 2a,b), determined by the level of phosphorylated kinase and kinase activity assays (not shown), both TNF and the TNF mimetic peptide enhanced the activity of p38 in these neutrophils (FIG. 2c, $p<0.05$) at concentrations which have been previously shown to promote the antimicrobial activity of neutrophils. The control peptide 205 did not activate p38 (data not presented). Under these experimental conditions, $TNF_{70-80}$ like TNF also stimulated a respiratory burst and primed neutrophils for an increase in agonist-induced chemiluminescence response and adherence (data not presented).

Figure 3:
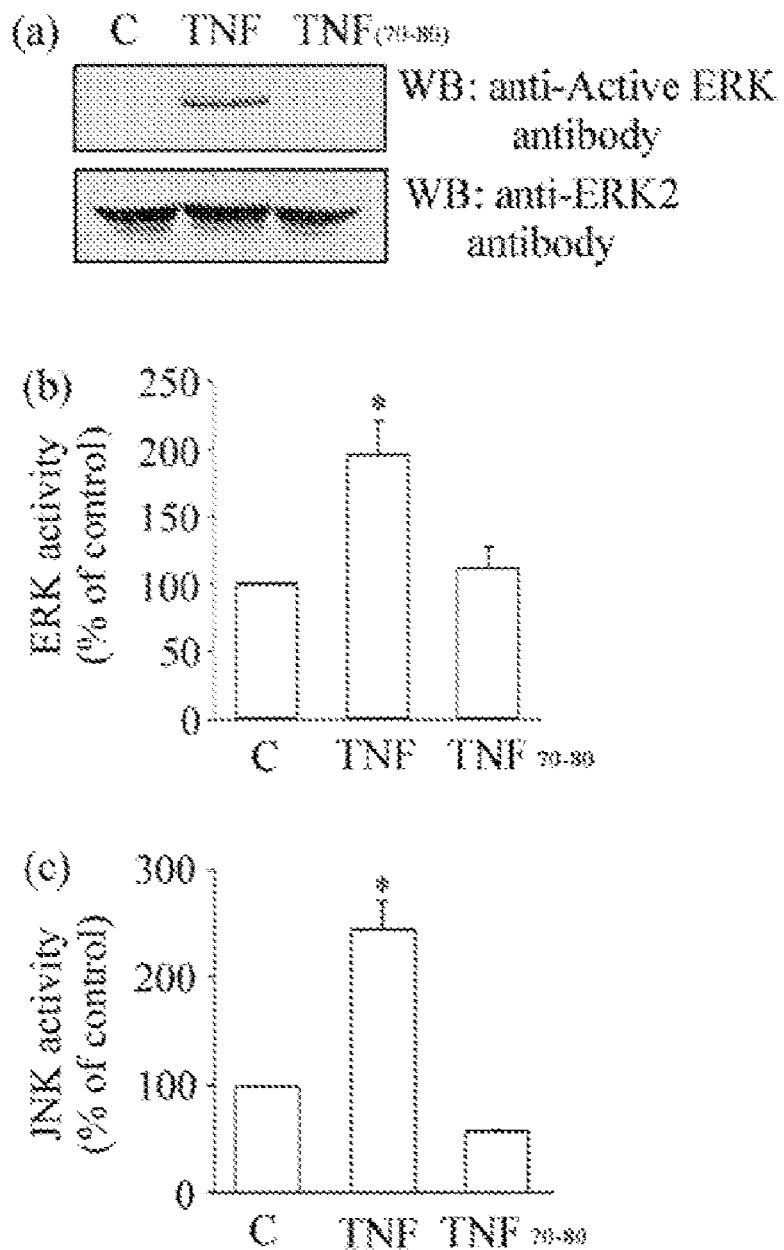
FIG. 3(a)-(c) show that TNF, but not $TNF_{70-80}$, activated ERK and JNK in adherent neutrophils. Neutrophils were adhered to culture dishes which had been precoated with autologous plasma and then incubated with HBSS, TNF (1000 U/ml), or $TNF_{70-80}$ (10 μM) for 15 min. ERK activation was determined by assessing the level of ERK1/ERK2 dual phosphorylation (a) or by kinase activity assay (b) after immunoprecipitation. JNK activity was assayed as described under Experimental using GST-jun (1-79) as the substrate (c). (a) Immunoblot probed with anti-ACTIVE ERK antibody (top panel), stripped, and re-probed with anti-ERK2 antibody (bottom panel). (b) The data is presented as the means+−sem of 3 experiments. (c) Shows GST-jun (1-79) phosphorylation presented as means+−sem of 3 experiments. Significance of difference between control and stimulated cells: *p<0.05.

TNF-stimulated activation of the ERK has previously been reported in adherent neutrophils. Consistent with this observation, ERK activity, determined by western blot analysis and enzymatic assay, was stimulated by TNF in neutrophils that had been pre-adhered to plasma-coated dishes (FIGS. 3a and 3b). Interestingly $TNF_{70-80}$ also failed to stimulate the activation of the ERKs (FIGS. 3a and 3b) in these cells. Under the same conditions, TNF but not $TNF_{70-80}$ stimulated the activity of JNK (FIG. 3c). Thus, $TNF_{70-80}$ shows a selective activation of p38.

Figure 4:
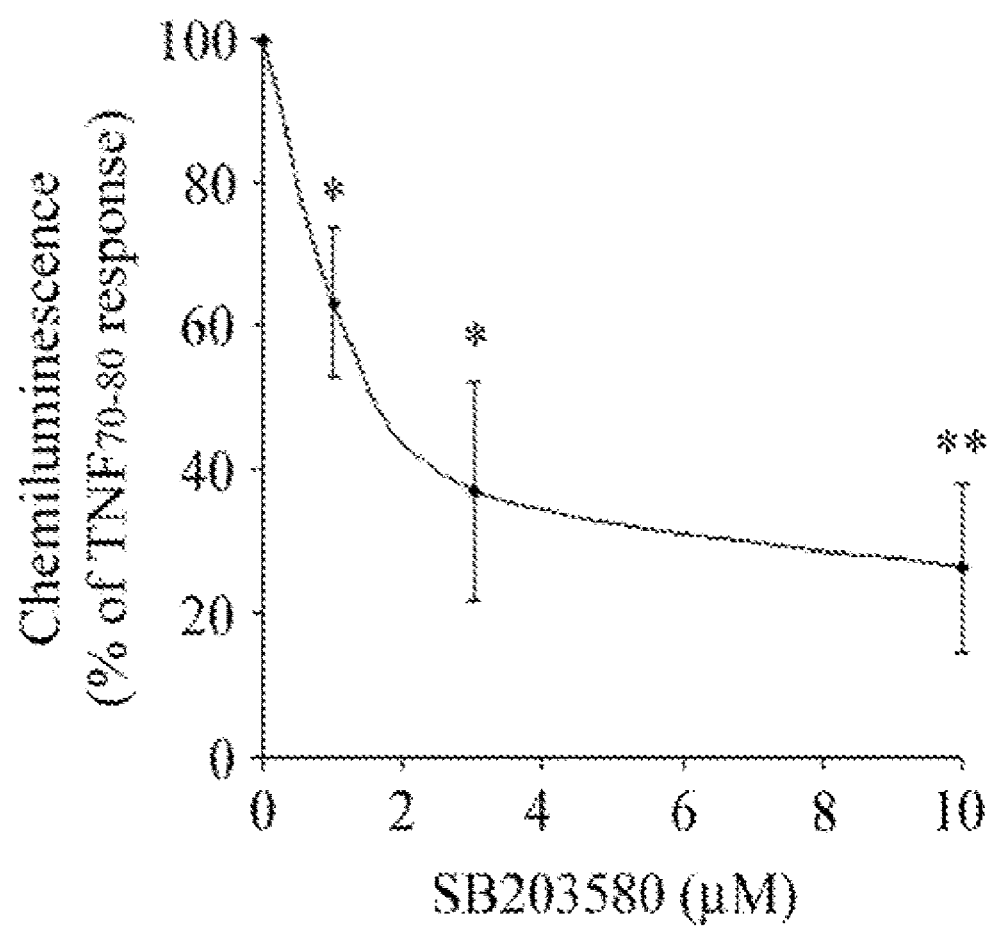
FIG. 4 shows that inhibition of the $TNF_{70-80}$ induced chemiluminescence response in neutrophils by the p38 inhibitor, SB203580. Neutrophils were pre-treated with varying concentrations of SB203580 for 30 min and then exposed to 10 μM $TNF_{70-80}$. The lucigenin enhanced chemiluminescence produced by the cells was measured in a luminometer. The peak initial rate of chemiluminescence produced is presented as the mean±sem of six experiments. The response in the presence of the inhibitor is expressed as a % of the control response. Statistical analyses, *p<0.05 and **P<0.01 when compared with control response.

To determine whether or not the activation of p38 was essential for the biological response of neutrophils, the effects of the p38 inhibitor, SB203580, on $TNF_{70-80}$ stimulated neutrophil superoxide production was examined. Neutrophils were pre-incubated with the inhibitor for 30 min, and then tested for ability to produce superoxide in response to 10 μM of the TNF mimetic by the chemiluminescence assay. The results showed that the neutrophil chemiluminescence response to the TNF mimetic peptide was significantly reduced in neutrophils pre-treated with the p38 inhibitor, in a concentration dependent manner (FIG. 4).

Example 12

$TNF_{70-80}$ Stimulates P38 Through the TNFR

Figure 5:
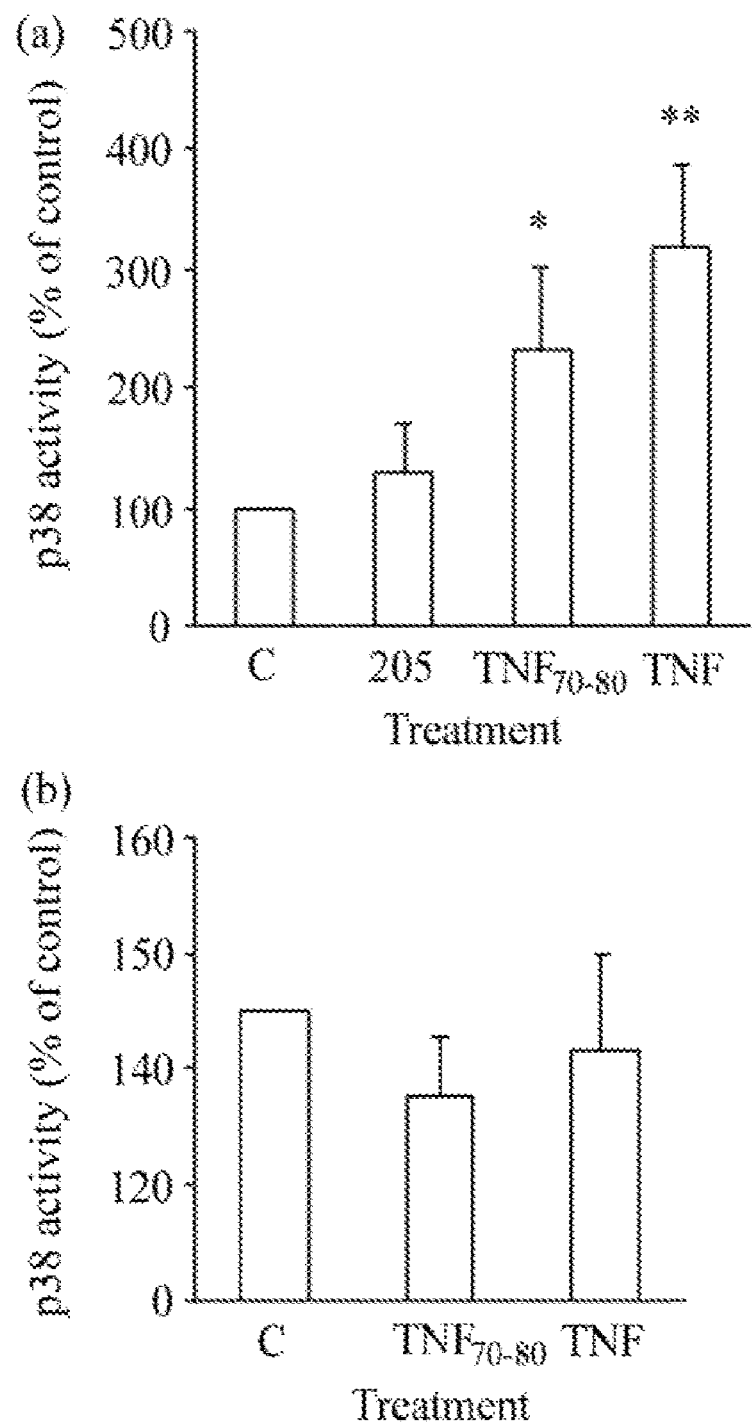
FIG. 5(a) and (b) show the inability of $TNF_{70-80}$ to stimulate p38 activation in cells lacking a TNFR. (a) Transfected (hTNFR1WT) or (b) non-transfected 70Z/3 cells were treated with $TNF_{70-80}$ (10 μM), TNF (1000 U/ml) or control peptide 205 (10 μM) at 37° C. for 5 min. The cells were then lysed, protein contents quantified and subjected to p38 kinase assay by Western blot. The results are presented as the mean+−sem of 3 experiments. Statistical analyses: *p<0.05 and **p<0.01 for the ability of TNF and peptides to activate p38.

Our previous studies have demonstrated that the biological effects of $TNF_{70-80}$ could be inhibited by the addition of soluble TNFR or anti-TNF monoclonal antibody. However, the role of the TNFR in the action of the peptide remained to be clearly defined. Here we took the approach of using cells which lacked TNF receptors and compared their response to the same cells which had been transfected with the TNFR. The mouse pre-B lymphocyte, 70Z/3 cells, lacking binding sites for TNF and being non-responsive to the cytokine, were transiently transfected with DNA (hTNFR1) and verified to express TNFR1 by western blot and flow cytometry analysis. The results presented in FIG. 5 show that neither TNF nor $TNF_{70-80}$ activated p38 in the non-transfected 70Z/3 cells. In comparison both molecules caused the activation of p38 in cells transfected with hTNFR1. The control peptide 205 failed to activate p38 in cells expressing the TNF receptor (FIG. 5).

Example 13

Requirement for TRAF2 in the Activation of p38 by $TNF_{70-80}$

The above data demonstrate that unlike TNF, $TNF_{70-80}$ did not significantly affect the activities of JNK and ERK in either adherent neutrophils or HUVEC. This suggests an inability of peptide-liganded TNF receptors to adequately couple the receptors to upstream elements that control the JNK module. The actions of TNF are mediated via the TNF receptor associated factor 2 (TRAF2) and activation of p38 by TNF has been demonstrated to involve TRAF2, receptor interacting protein (RIP) and apoptosis signal regulating kinase-1 (ASK-1) (Kyriakis, J. M., and Auruch, J. (2001) *Physiol Rev.* 81: 807-869). On the other hand, JNK can be activated by TNF via at least two parallel pathways, one involving TRAF2, a member of the STE20 family of kinases and MAP kinase/ERK kinase kinase 1 (MEKK1), and the other involving TRAF2 and ASK-1 (Kyriakis, J. M., and Auruch, J. (2001) *Physiol. Rev.* 81: 807-869). To attempt to understand how $TNF_{70-80}$ selectively activated the p38 module, it is important to determine whether TRAF2 was involved in the action of the peptide, not only to confirm an inability of the peptide to couple TRAF2 to divergent downstream MAP kinase modules but also to support the idea that the peptide acted via the TNF receptor-TRAF2 axis.

Figure 6:
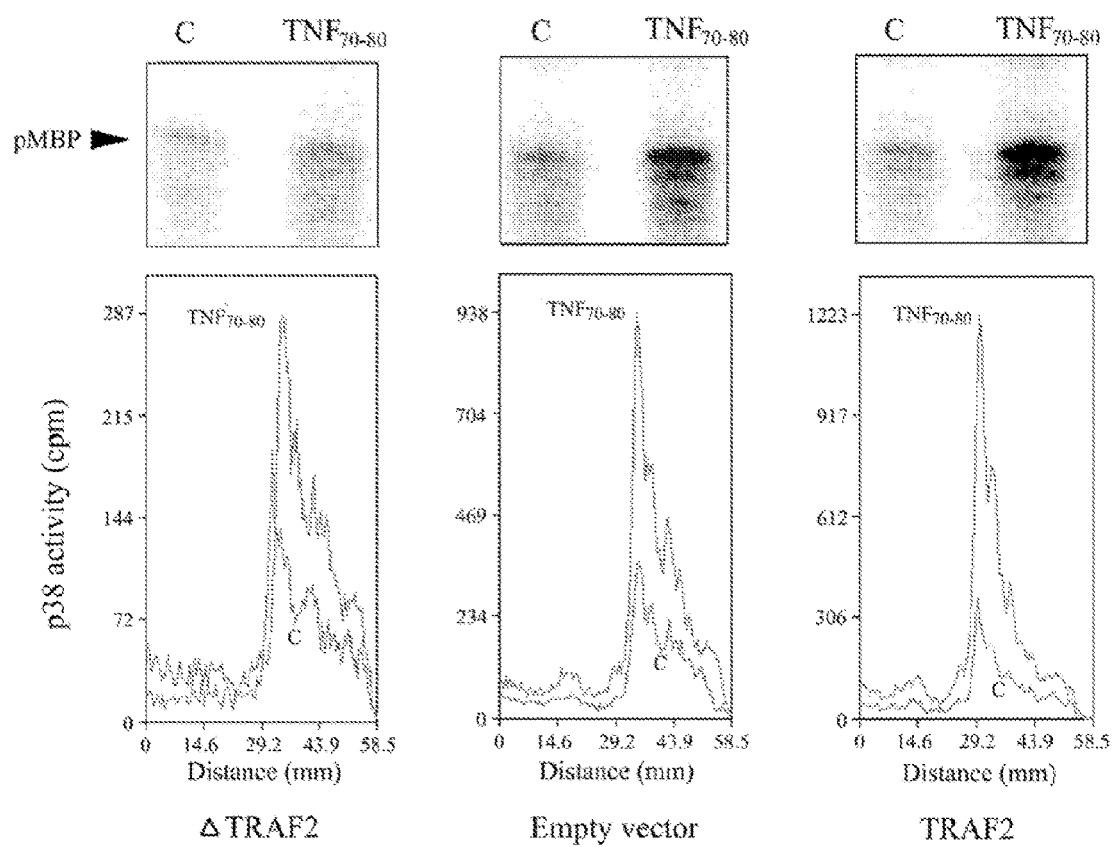
FIG. 6 shows that $TNF_{70-80}$ stimulated p38 activity via TRAF2. HEK 293T cells were stably transfected with wild-type TRAF2, a dominant-negative TRAF2 (ΔTRAF2) or an empty vector. $TNF_{70-80}$ (10 μM) was added and the cells were incubated for 5 min. at 37° C., lysed and p38 immunoprecipitated. Kinase activity was assayed using myelin basic protein as a substrate. The data (representative digital radiogram and profile of phosphorylated MBP) shown are representative of 2 experiments.

Firstly we established that $TNF_{70-80}$ was able to stimulate the activity of p38 in human embryonic kidney HEK293T cells. Then we stably transfected these cells with wild-type TRAF2, a dominant-negative TRAF2 (TRAF287-501, ΔTRAF2) or an empty vector. The data in FIG. 6 demonstrate that while over expression of TRAF2 enhanced the activation of p38 by $TNF_{70-80}$ compared to cells transfected with an empty plasmid, expression of ΔTRAF2 caused a substantial attenuation of this response. The levels of TRAF2 and ΔTRAF2 in the TRAF2-over-expressing and ΔTRAF2-expressing cells were similar (data not shown).

Example 14

$TNF_{70-80}$ Activates the NFκB Signalling Pathway

Figure 7:
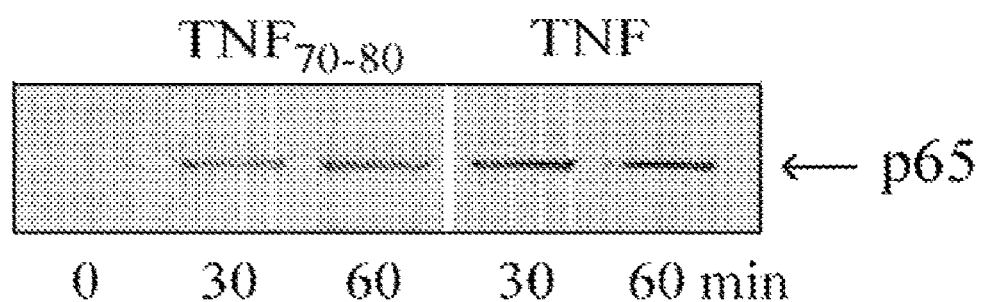
FIG. 7 shows activation of NFκB by TNF and $TNF_{70-80}$ in human neutrophils. Cells were stimulated with either TNF (100 U/ml) or $TNF_{70-80}$ (10 μM) for either 30 min or 1 h at 37° C. After cell lysis, nuclear fractions were prepared, nuclear proteins separated by SDS page (12% gel), transferred to nitrocellulose and probed with an anti NFκB p65 antibody (Santa Cruz). Results represent one experimental run representative of results obtained in two other experiments.

TNF receptors are coupled to the NFκB pathway via TRAF2 and it has been proposed that this action protects cells against TNF-induced apoptosis. We investigated whether $TNF_{70-80}$ was able to couple TNF receptors to the NFκB pathway. This pathway, akin to the p38 pathway, is dependent on TRAF-2 and RIP (Kyriakis, J. M., and Auruch, J. (2001) *Physiol Rev.* 81: 807-869). We measured the nuclear translocation of NFκB as an indicator of the activation of this pathway. The results obtained in neutrophils showed that $TNF_{70-80}$ caused the translocation of NFκB to the nucleus (FIG. 7). This correlated with results showing that both TNF and the mimetic caused the degradation of IκB (data not shown). These data imply that the $TNF_{70-80}$-liganded TNF receptors were able to functionally couple TRAF2 to the NFκB pathway. The data also suggest that the inability of $TNF_{70-80}$ to up regulate the expression of adhesion molecules in HUVEC was unlikely to be due to a lack of activation of the NFκB pathway which is essential for adhesion molecule expression (Read, M. A., Whitley, M. Z., Gupta, S., Pierce, J. W., Best, J., Davis, R. J., and Collins, T. (1997) *J. Biol. Chem.* 272: 2753-2761; Min, W., and Pober, J. S. (1997) *J. Immunol.* 159: 3508-3518).

Example 15

Effects of TNF$_{70-80}$ on Upstream Signalling Molecules

The above data demonstrate that TNF$_{70-80}$ selectively activated p38 but not the JNK and ERK MAP kinases. This unique property of the peptide was likely to be due to the ability of TNF$_{70-80}$-liganded TNF receptors to discriminate between the various signalling molecules downstream of TRAF2 as opposed to the non-discriminatory manner in which TNF-liganded receptors act. For example, in contrast to TNF-ligated receptors, TNF$_{70-80}$-liganded receptors might not couple TRAF2 to the upstream elements of the JNK and ERK pathways, resulting in a lack of activation of these MAP kinases. To address this, we focused on the JNK module as a number of kinases have been demonstrated to couple TRAF2 to JNK. Furthermore, ligand-stimulated activation of many of these signalling molecules has not yet been addressed in neutrophils.

Figure 8:
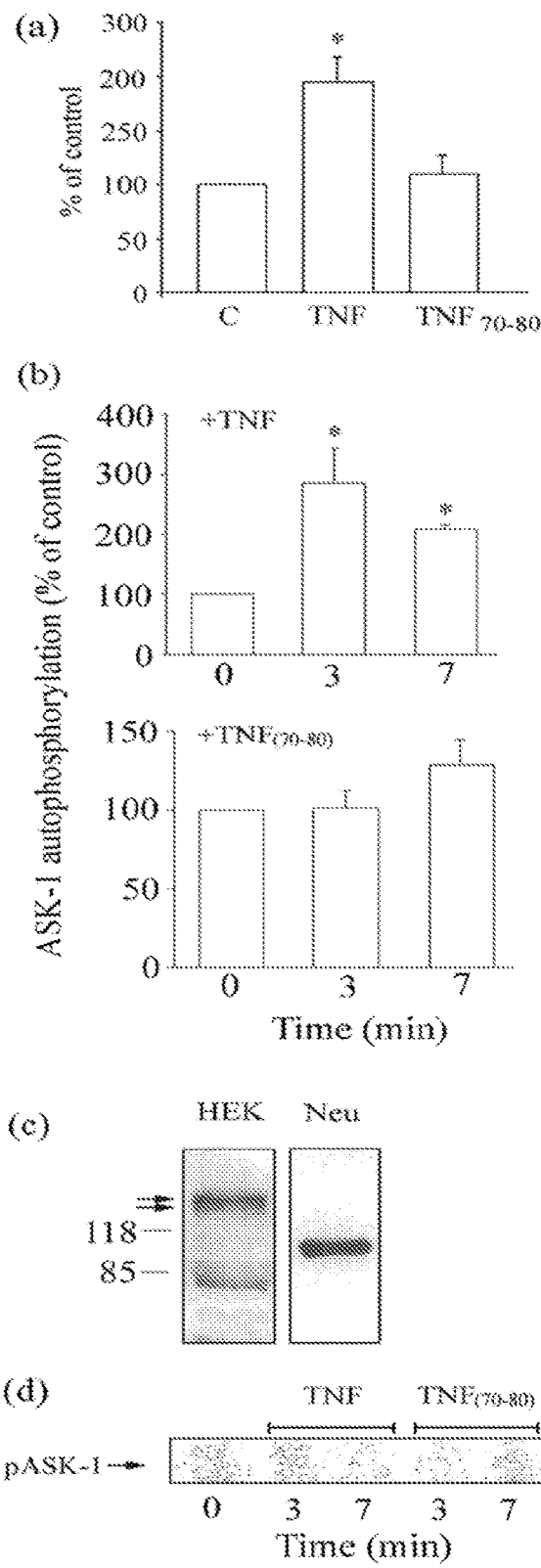
FIG. 8(a)-(d) show that TNF but not $TNF_{70-80}$ activated GCKR in neutrophils and ASK-1 in HEK293T cells, and lack of effect of TNF and $TNF_{70-80}$ on ASK-1 activity in neutrophils. (a) Neutrophils were adhered to autologous plasma coated culture dishes and treated for 15 min with either HBSS, TNF (1000 U/ml) or $TNF_{70-80}$ (10 μM). GCKR was immunoprecipitated from cell lysates and activity assayed using myelin basic protein (MBP) as the substrate. The data for the phosphorylated MBP is presented as mean kinase activity+−sem; (b) HEK293T cells were incubated with TNF or $TNF_{70-80}$ for 3 or 7 min, lysed and autophosphorylation of immunoprecipitated ASK-1 was determined. Results shown are the means+−sem of 3 experiments; (c) Expression of ASK-1 in HEK293T cells and neutrophils as determined by Western blot analysis of cell lysates. Arrows show a dark and light band in HEK293T cells with the expected Mr for ASK-1; both bands were absent in neutrophils but an immunoreactive band with a Mr of approximately 95 kDa was clearly evident; (d) To investigate whether TNF and $TNF_{70-80}$ were able to stimulate the activity of ASK-1 in neutrophils, neutrophils were adhered to dishes which had been precoated with autologous plasma and then incubated with TNF or $TNF_{70-80}$ for 3 or 7 min. Activation of ASK-1 was determined by kinase autophosphorylation. A representative digital radiogram from 3 experiments is shown.

The STE20 family of kinases constitutes a group of upstream regulators of the JNK module, acting directly on MEKK1. Members of the STE20 kinases have also been reported to bind to and are activated by TRAF2. Although TNF has been demonstrated to stimulate the activities of some of these kinases, which include germinal center kinase (GCK), GCKR and GCK-like kinase (GLK) in some cell-types, such an effect has not been reported in neutrophils. We therefore investigated whether TNF and TNF$_{70-80}$ were able to stimulate the activity of GLK and GCKR. Neutrophils were pre-adhered to plasma-coated dishes, stimulated with TNF, lysed and the lysates were incubated with an anti-GCKR antibody which detects both GCKR and GLK. Using kinase assay conditions essentially as described in Shi, C. S., Leonardi, A., Kyriakis, J., Siebenlist, U., and Kerhli, J. H. (1999) J. Immunol. 163: 3279-3285, the data in FIG. 8a show that TNF$_{70-80}$ in comparison to TNF was poor at stimulating GCKR/GLK activity in adherent neutrophils. This finding is consistent with the observation that under this condition, TNF stimulated the activity of JNK (FIG. 2c). There was a requirement for plasma-coated surfaces since TNF failed to stimulate the activity of either GCKR or JNK when neutrophils were pre-adhered to non-coated surfaces (data not shown).

Figure 2:
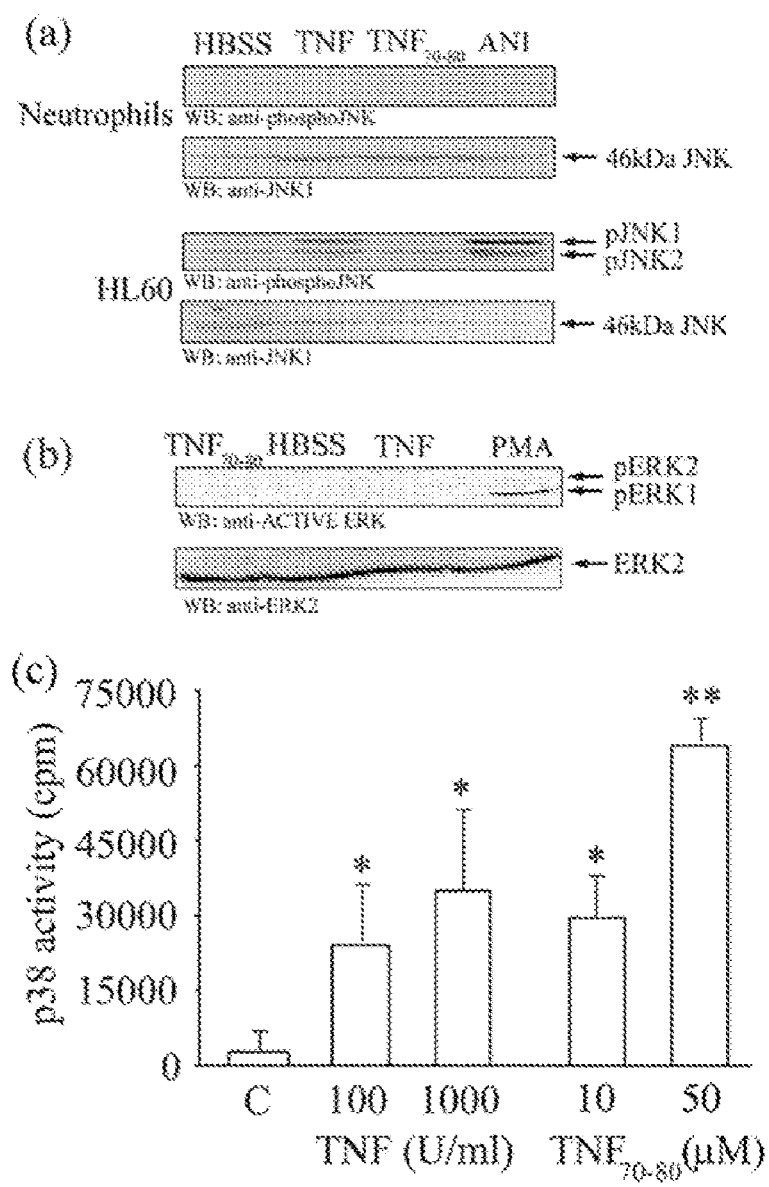
FIG. 2(a)-(c) show the effects of TNF and $TNF_{70-80}$ on MAP kinases in neutrophils. To investigate the activation of JNK (a), neutrophils or HL60 cells were incubated with TNF (100 U/ml), $TNF_{70-80}$ (10 μM) or anisomycin (2.5 μg/ml) for 15 min, the cells were lysed and degree of JNK activation was determined by western blot analysis using an anti-phospho-JNK antibody (upper panel for each cell-type). The blots were stripped and reprobed with anti-JNK1 antibody which detected the p46-kDa JNK1 isotype in each lane. TNF and anisomycin increased JNK phosphorylation in HL60 cells but not in neutrophils. To assess the activation of ERK1/ERK2 (b), neutrophils were incubated in the presence or absence of TNF, $TNF_{70-80}$ or PMA (100 nM) for 15 (TNF and $TNF_{70-80}$) or 5 (PMA) min. The cells were lysed and the lysate assessed by western blot analysis for the level of dual-phosphorylated ERK1/ERK2 (top panel) and ERK2 protein (bottom panel). Only PMA increased the dual phosphorylation of ERK1/ERK2 in neutrophils. To assess the activation of p38 (c), neutrophils were incubated in the absence or presence of TNF (100 or 1000 U/ml) or $TNF_{70-80}$ (10-50 μM) for 5 min., lysed, p38 immunoprecipitated and kinase activity was assayed using myelin basic protein as a substrate. The level of myelin basic protein phosphorylation was quantitated by an Instant Imager. Results presented (a and b) are from one experiment, representative of three-four experiments, each conducted using cells from a different donor. In (c), shows data from 3 experiments (means+−SEM). Significance of difference between control and TNF or $TNF_{70-80}$: *p<0.05; **p<0.01. The control peptide 205 did not cause activation of p38 (data not presented).

The p38 and JNK modules can also be activated by TNF via ASK-1, and this has been demonstrated in cell-types such as HEK293T cells. ASK-1 has also been reported to bind to and is activated by TRAF2. We therefore compared the ability of TNF and TNF$_{70-80}$ to activate ASK-1 in these cells, by determining the level of autophosphorylation of the kinase, a hallmark of ASK-1 activation (Kyriakis, J. M., and Auruch, J. (2001) Physiol. Rev. 81: 807-869). While TNF caused a transient increase in ASK-1 autophosphorylation, peaking at 3 min, TNF$_{70-80}$ did not affect the level of ASK-1 phosphorylation (FIG. 8b). However, treatment of HEK293T cells with TNF$_{70-80}$ for 5 min increased p38 activity by 243+27% over control (p<0.05, n=3). This further confirms the selective signalling by TNF$_{70-80}$ for p38, independently of the cell type used. Since activation of ASK-1 in neutrophils has not yet been reported, we investigated whether TNF was able to activate ASK-1 in these cells and whether TNF$_{70-80}$ again differed from TNF in its ability to stimulate ASK-1. Western blot analysis of neutrophil lysates with the anti-ASK1 antibody revealed the presence of an immunoreactive band which migrated with a Mr of approximately 95,000 (FIG. 8c). In contrast, ASK-1 from HEK293T cells migrated as a doublet with a Mr of approximately 155,000, consistent with the reported Mr of approximately 150,000. Under the conditions in which activation of JNK and GCKR/GLK was observed, neither TNF nor TNF$_{70-80}$ increased the level of ASK-1 phosphorylation in adherent neutrophils (FIG. 8d). ASK-1 phosphorylation was also not altered by TNF or TNF$_{70-80}$ in non-adherent neutrophils (data not shown), despite these conditions being conducive to p38 activation (FIG. 2).

Example 16

Figure 9:
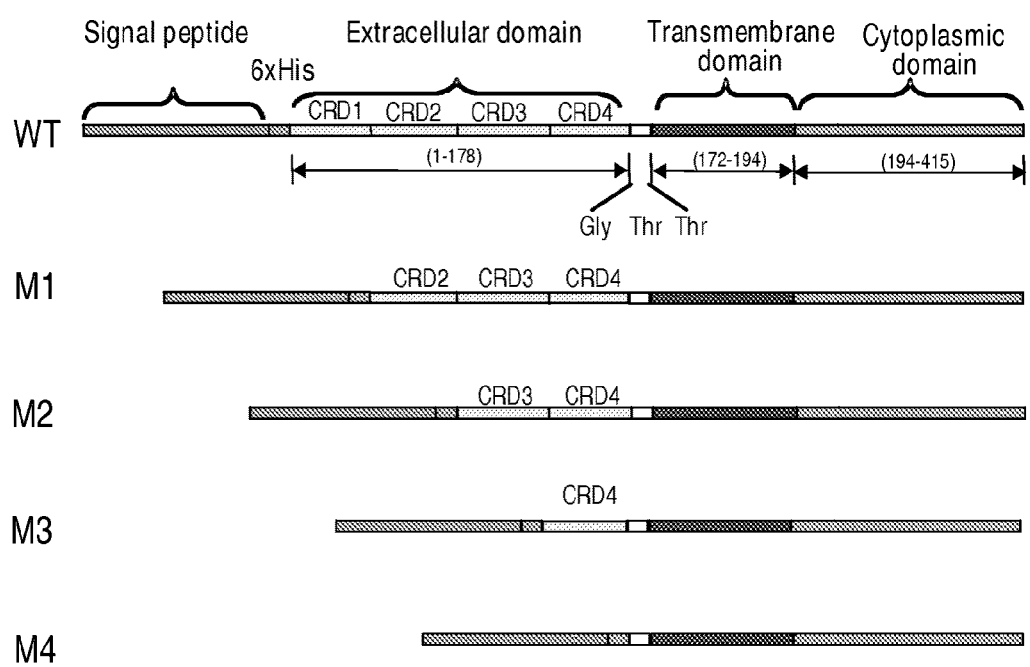
FIG. 9 shows a diagrammatic representation of TNFR I mutants. Abbreviations: WT, wild type; CRD, cysteine-rich domain; His, histidine; M, mutant. The signal peptide is cleaved from the mature receptor protein.

Mapping the Region on the p55 kDa TNF Receptor Through which TNF$_{70-80}$ Acts The extracellular portion of the p55 kDa TNF receptor contains four cysteine-rich domains (C1-C4; FIG. 9). We have made deletion mutants in which C1, C1+C2+C3 and all four cysteine-rich domains are deleted. The mutant or wild type receptor constructs were then transfected into the 70Z preB cell-line which lack TNF receptors. As expected, TNF and TNF$_{70-80}$ did not stimulate the activity of p38 in cells transfected with an empty vector but stimulated the activity of p38 in cells transfected with wild type receptors. When the C1 domain was deleted, both TNF and TNF$_{70-80}$ were able to stimulate the activity of p38. With C1-C3 deleted, the ability of TNF to stimulate p38 was greatly diminished but the peptide was still able to stimulate p38 activity. The peptide retained its ability to stimulate p38 activity when C1-C4 were deleted. TNF was not able to stimulate kinase activity when the cells were transfected with this construct. The data imply that the remaining extracellular sequence juxtaposed to the plasma membrane is sufficient for TNF$_{70-80}$ to stimulate p38 activity.

Example 17

TNF$_{70-80}$-TNF-R1 Interaction

To determine whether the synthetic TNF$_{70-80}$ peptide mediates its effects through the interaction with the TNF-R1, competitive binding of TNF$_{70-80}$ and biotin-labelled TNF$_{70-80}$ to recombinant human soluble TNF receptor inhibitor/Fc chimera (rHusTNFRI) was investigated using a solid-phase binding assay, as described below. Prior attempts to introduce a tyrosine residue into the peptide rendered it inactive and resulted in its failure to associate with membranes.

The solid-phase ligand binding assay involved coating Microtitre plates (Maxisorp; Nunc) with 100 µl/well of 3 µg/ml rHusTNFRI (prepared as a chimaeric protein with the 6× histidine tagged Fc part of human IgG1) (Prospec-Tany TechnoGene Ltd, Rehovot, Israel) in 18 MΩ-cm H$_2$O overnight at 4° C. and blocked with 1% BSA and 0.05% Tween 20 in PBS for 1 hr at 4° C. 10 µM of biotin-labelled TNF$_{70-80}$ (Auspep, Victoria, Australia) plus various concentrations of unlabelled TNF$_{70-80}$ (Auspep, Victoria, Australia) or control peptide (H-GGDPGIVTH-OH; SEQ ID NO. 14) (Peptech) were added to each well and incubated for 3 h at 4° C. After washing the wells four times with was buffer (PBS with 0.05% Tween 20), the plates were incubated with 100 µl/well of poly-horseradish peroxidase streptavidin conjugate (Endogen, Rockford, Ill.) at concentration of 1/6000 (in 1% BSA and 0.05% Tween 20 in PBS) for 45 mins at 4° C. Wells were then washed four times with was buffer and bound enzyme detected by the addition of 3',3',5',5'-tetramethylbenzidine (TMB) substrate (Sigma Chemical Company Ltd, St Louis, Mo.). Absorbance readings were measured using dual filter at 570/450 nm on a Dynatech MR700 Plate Reader.

Figure 10:
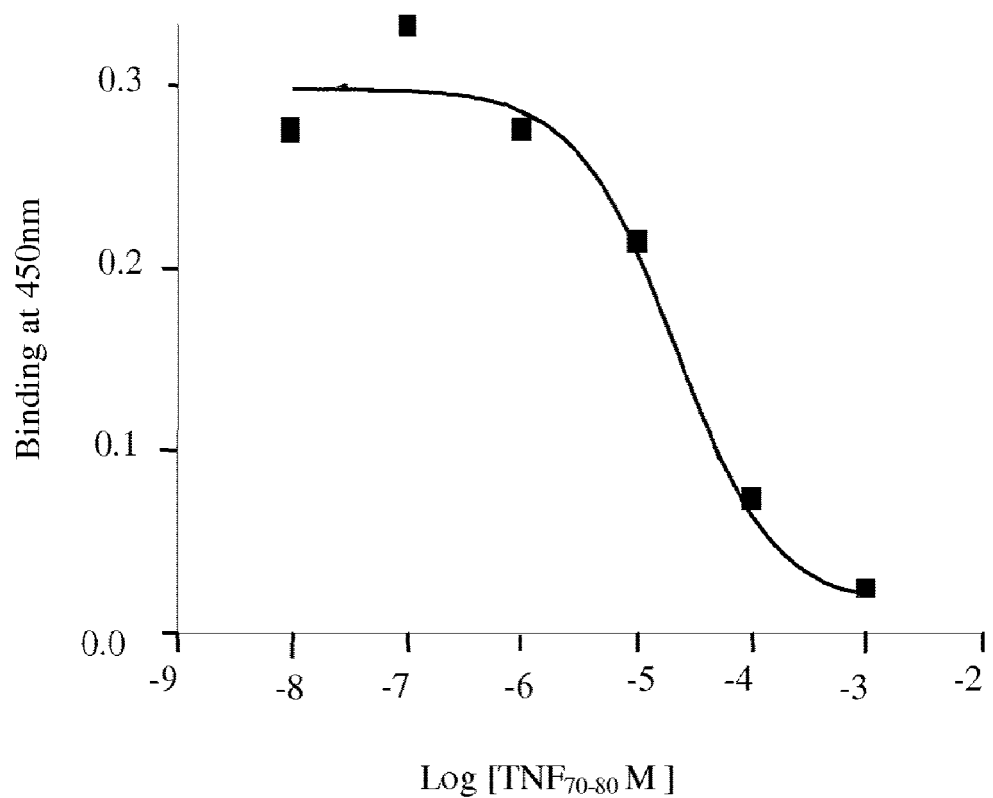
FIG. 10 shows estimation of binding affinities by using a simple microtitre-plate based competition binding assay with biotinylated $TNF_{70-80}$. Displacement curve with increasing concentrations of $TNF_{70-80}$ and the biotinylated $TNF_{70-80}$, captured by immobilised rHusTNFRI on the surface of microtitre plates is shown. 10 μM of biotinylated $TNF_{70-80}$ as the tracer was incubated with the indicated concentrations of $TNF_{70-80}$. The ELISA was performed as described in the Examples. The $IC_{50}$ of ≈21 μM was obtained (mean of duplicate wells from two experiments) using GraphPad Prism 4.

FIG. 10 shows the displacement curve with increasing concentrations of TNF$_{70-80}$ and the biotinylated TNF$_{70-80}$, captured by immobilised rHusTNFRI on the surface of microtitre plates. 10 μM of biotinylated $TNF_{70-80}$ was used as the tracer incubated with the indicated concentrations of $TNF_{70-80}$. The IC50 of ≈21 μM was obtained (mean of duplicate wells from two experiments) using GraphPad Prism 4.

Figure 11:
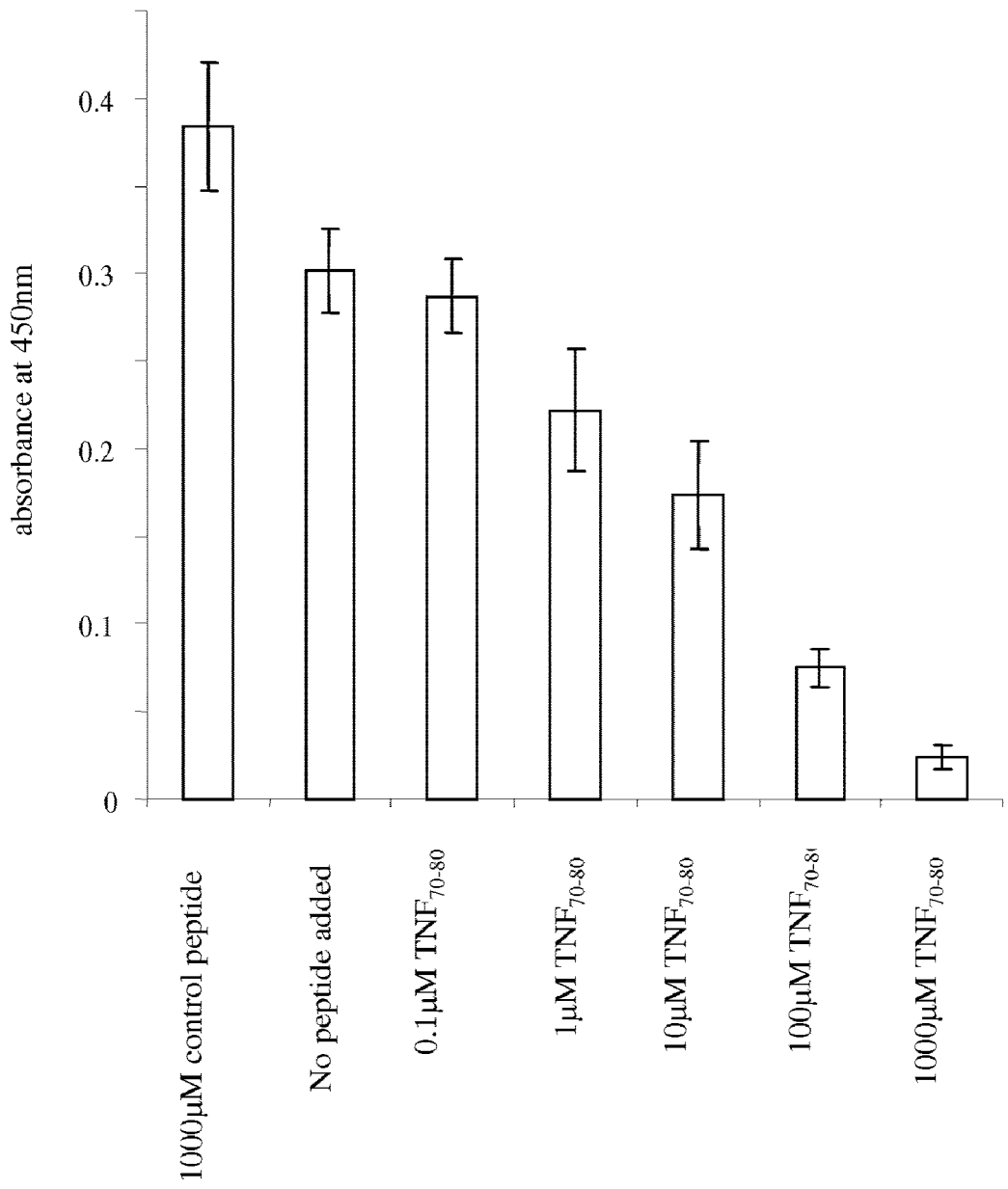
FIG. 11 shows $TNF_{70-80}$ inhibits biotinylated $TNF_{70-80}$ binding to immobilised rHusTNFRI. rHusTNFRI (3 μg/ml) coated each well of a microtitre plate, and biotinylated (10 μM) plus various concentrations of $TNF_{70-80}$ added. Bound biotinylated $TNF_{70-80}$ was detected by the addition of poly-horseradish peroxidase streptavidin. All data represent means±SEM from duplicate wells from two independent experiments.

FIG. 11 shows that $TNF_{70-80}$ inhibits biotinylated $TNF_{70-80}$ binding to immobilised rHusTNFRI. rHusTNFRI (3 μg/ml) was coated onto each well of a microtitre plate, and biotinylated $TNF_{70-80}$ (10 μM) plus various concentrations of $TNF_{70-80}$ added. Bound biotinylated $TNF_{70-80}$ was detected by the addition of poly-horseradish peroxidase streptavidin.

The data shows that unlabelled $TNF_{70-80}$ was able to inhibit $TNF_{70-80}$ binding to immobilised rHusTNFRI in a concentration-dependent manner, with the half-maximal inhibition concentration ($IC_{50}$) of $TNF_{70-80}$ estimated to be ≈21 μM and a Kd of $9\times10^{-5}$ M.

Figure 12:
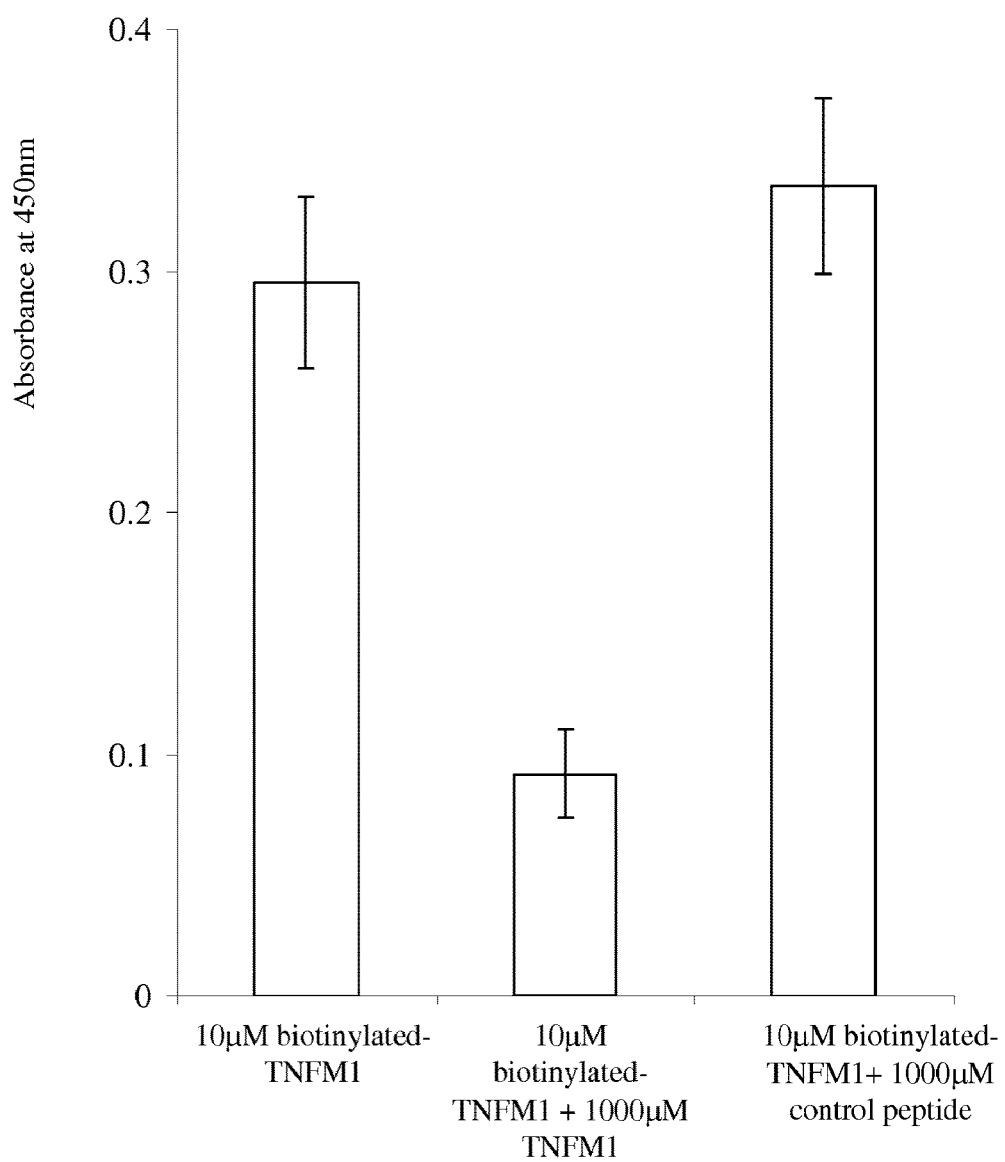
FIG. 12 shows the effect of the control peptide on the specific binding of biotinylated $TNF_{70-80}$ to the immobilised rHusTNFRI. rHusTNFRI (3 μg/ml) coated each well of a microtitre plate, and biotinylated $TNF_{70-80}$ (10 μM) plus 1000 mM of the control peptide were added. Bound biotinylated $TNF_{70-80}$ was detected by the addition of poly-horseradish peroxidase streptavidin. All data represent means±SEM from duplicate wells from two independent experiments.

FIG. 12 shows the effect of the control peptide on the specific binding of biotinylated $TNF_{70-80}$ to the immobilised rHusTNFRI. The 11-mer peptide $TNF_{70-80}$ was shown to compete with biotinylated $TNF_{70-80}$ for binding to TNF-R1. The observed interaction with TNF-R1 is in accordance with indirect evidence where sTNFRI has been able to block bone marrow-derived macrophage activation by $TNF_{70-80}$.

Figure 13:
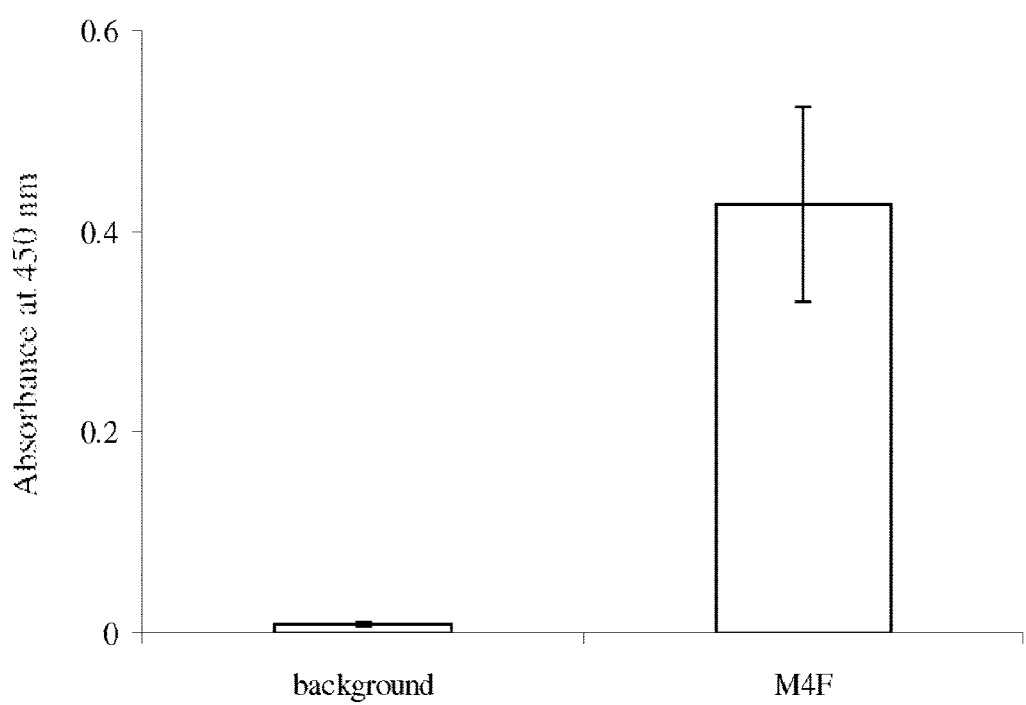
FIG. 13 shows binding of biotinylated $TNF_{70-80}$ to mutant receptor peptide M4. 100 µl of 0.7 mM solution of M4 or 1% BSA in PBS for control was coated on plates overnight for 24 hrs at 37° C. Plates were blocked for 6 hrs at 37° C. with 3% BSA in PBS. 100 µl of 20 µM of B-$TNF_{70-80}$ was added to each well and allowed to incubate for 18 hrs at 37° C. Streptavidin-horseradish peroxidase and TMB $H_2O_2$ was added and bound product was detected by measuring absorbance at 450 nm.

FIG. 13 shows binding of biotinylated $TNF_{70-80}$ to mutant receptor peptide M4. 100 μl of 0.7 mM solution of M4 or 1% BSA in PBS for control was coated on plates overnight for 24 hrs at 37° C. Plates were blocked for 6 hrs at 37° C. with 3% BSA in PBS. 100 μl of 20 μM of B-$TNF_{70-80}$ was added to each well and allowed to incubate for 18 hrs at 37° C. Streptvadin-horseradish peroxidase and TMB $H_2O_2$ was added and bound product was detected by measuring absorbance at 450 nm.

This shows that $TNF_{70-80}$ binds to the truncated receptor and identifies a binding region for $TNF_{70-80}$ on the TNF receptor.

Figure 14:
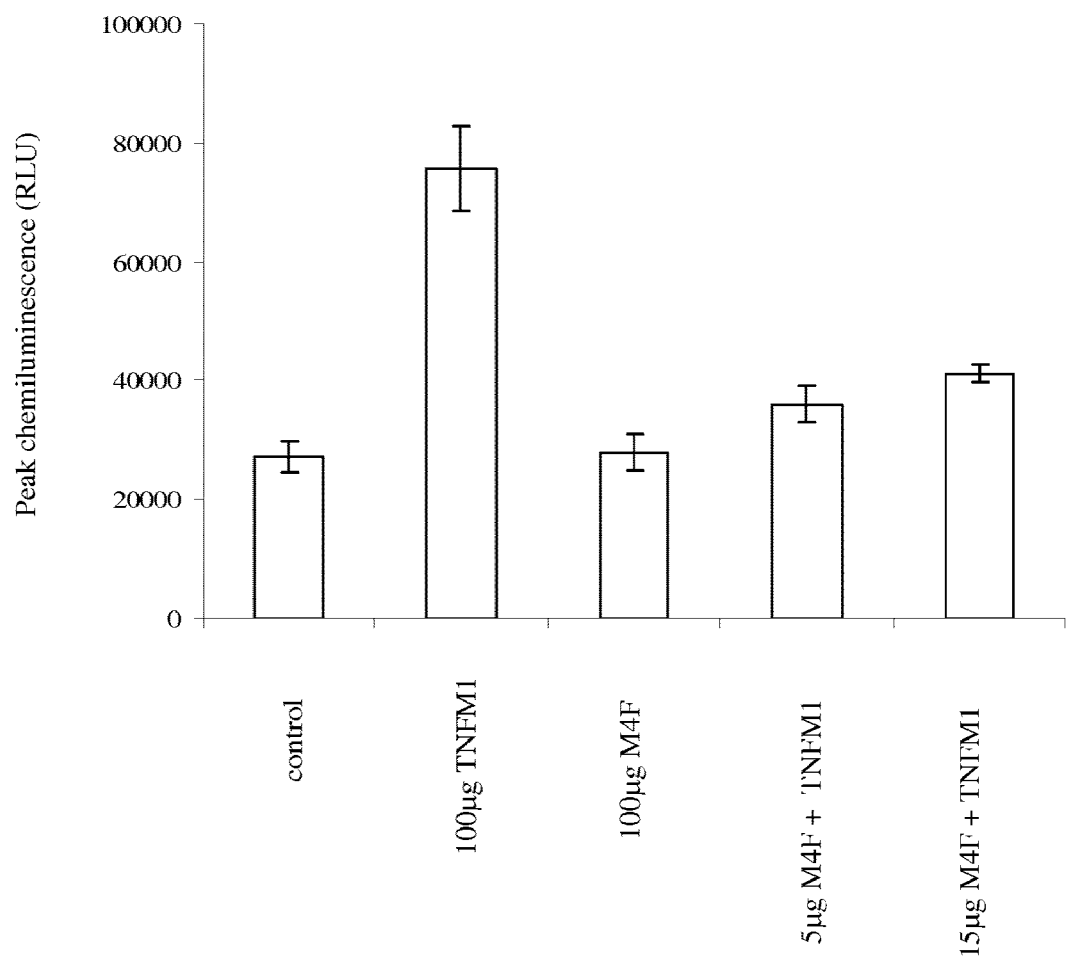
FIG. 14 shows the effect of TNFR1 fragment-M4 on $TNF_{70-80}$-induced superoxide production in neutrophils. Various concentrations of TNFR1 fragment or diluent were added to neutrophils (106 in 100 µl HBSS) and incubated at 37° C. for 30 min 5% $CO_2$ in air. After incubation 500 µl of lucigenin (250 µM, final), 100 µl of $TNF_{70-80}$ (100 µg) were added and the final volume was adjusted to 1 ml. The results are presented as mean±SEM of three independent experiments using neutrophils from different individuals.

FIG. 14 shows the effect of TNFR1 fragment-M4 on $TNF_{70-80}$-induced superoxide production in neutrophils. Superoxide production by human neutrophils was measured by the reduction of the fluorescent lucigenin, (9,9'-bis(N-methyl-acridinium nitrate) (Sigma Chemical Company). Lucigenin-dependant chemiluminescence was measured as described previously (Hardy et al., 1995). Briefly, various concentrations of TNFR1 fragment (H-HHHHHHLKPGTT-OH; SEQ ID NO. 8) were added to 100 μl of $1\times10^6$ neutrophils in a final volume of 400 μl HBSS and incubated at 37° C. for 30 min 5% $CO_2$ in air. After incubation 500 μl of lucigenin (250 μg/ml in HBSS) and 100 μl of $TNF_{70-80}$ (100 μg) were added and the final volume was adjusted to 1 ml. The cells were placed in a water-jacketed luminometer chamber (37° C.) (Autolumat Plus Model LB 953, Berthold Technologies, Bundoora, Australia) and the resulting light output recorded in millivolts (mV) at 10 second intervals. The data was analysed with Multiuser software (Berthold Tubemaster, Bundoora, Australia). The results are expressed as peak superoxide produced.

Various concentrations of TNFR1 fragment or diluent were added to neutrophils (106 in 100 μl HBSS) and incubated at 37° C. for 30 min 5% $CO_2$ in air. After incubation 500 μl of lucigenin (250 μM, final), 100 μl of $TNF_{70-80}$ (100 μg) were added and the final volume was adjusted to 1 ml. These results demonstrate that the peptide representing the M4 region of the TNFR (Gly-Thr-Thr) can block the biological activity of the $TNF_{70-80}$ in a neutrophil chemiluminescence assay.

The data presented demonstrates that the $TNF_{70-80}$ peptide binds specifically to the TNFR in a typical ligand-receptor dynamics. A peptide made of the perceived region to which $TNF_{70-80}$ binds (M4), Gly-Thr-Thr, was able of inhibiting the biological action of $TNF_{70-80}$.

Discussion

The finding that TNF stimulated the activities of JNK, p38 and ERK in endothelial cells and adherent neutrophils, together with our finding that $TNF_{70-80}$ caused little or no stimulation of the activities of JNK and ERK in these cells in contrast to p38, is likely to explain why $TNF_{70-80}$ does not induce the expression of E-selectin on HUVECs. Consistent with this, other studies have reported that maximal transcription of the E-selectin gene by TNF required the activation of JNK and p38 which phosphorylate the transcription factors ATF-2 and/or c-Jun. Over-expression of phosphorylation-defective ATF-2 or expression of kinase-inactive JNK prevented TNF from stimulating the expression of E-selectin. Although NFκB is also required for the upregulation of E-selectin, our data showing that $TNF_{70-80}$ promotes IκBα degradation (unpublished data) and the translocation of NFκB to the nucleus suggest that activation of the NFκB pathway per se is insufficient for stimulating E-selectin transcription.

In non-adherent neutrophils, our data demonstrate that $TNF_{70-80}$ did not differ from TNF in its ability to stimulate the activity of p38 but not of JNK or ERK. Other studies have found that treating human neutrophils with SB203580, a p38 inhibitor, inhibited TNF-induced phosphorylation and activation of cytoplasmic phospholipase A2 and signalling downstream of p38 MAP kinase. In addition, SB203580 has recently shown to inhibit the TNF induced superoxide generation of human neutrophils, but inhibition of the ERK pathway had no effect on the superoxide production induced by TNF. This is consistent with studies that show the lack of activation of ERK in non-adherent neutrophils incubated with TNF. The inability of TNF to stimulate the activity of JNK or ERK in non-adherent neutrophils is in direct contrast to data obtained in other studies from cell types such as mesangial cells, endothelial cells, HL60 cells and adherent neutrophils. The present study, therefore suggests that signalling via the p38 but not JNK and ERK may be important for the stimulation and priming of non-adherent neutrophils for enhanced superoxide production by TNF.

Evidence has also been presented demonstrating that the TNF mimetic peptide acts via the TNFR. Thus p38 could not be stimulated in cells lacking TNFR but was activated in cells transfected with the TNFR1 gene. Previously the role of the TNFR was not clear, and these studies only suggested that $TNF_{70-80}$ acted via this receptor. This is supported by the finding that the actions of the peptide could be inhibited by an anti-TNF antibody which neutralises TNF activity and secondly, that antibodies against the soluble TNFR1 also inhibited $TNF_{70-80}$ activity on macrophages. We have been unable to examine the direct binding to cells because our attempts to make a modified $TNF_{70-80}$ containing a tyrosine residue that could be iodinated for receptor-binding studies, led to loss of activity and the peptide failed to associate with cell membranes. The selective activation of p38 by $TNF_{70-80}$ is conducive with the biological significance of this response where our data show that the $TNF_{70-80}$ induced neutrophil chemiluminescence response could be inhibited by the p38 inhibitor, SB203580.

Binding of the trimeric TNF to the p55 kDa TNF receptor complexes initiates the recruitment of receptor-associated proteins such as TRAF-2, TRADD and FADD to the TNF receptors. It is feasible that $TNF_{70-80}$ being a monomer, was unable to recruit all of these receptor-associated proteins in the same manner as TNF. Consequently, this would have a major impact on the range of signalling molecules that $TNF_{70-80}$ can stimulate. The importance of TRAF2 in TNF-stimulated MAP kinase activation and expression of E-selectin is demonstrated by the observations that N-terminal truncation of TRAF-2 blocked not only TNF-induced JNK activation but also E-selectin gene transcription and overexpression of a dominant negative mutant of TRAF2 inhibited p38 activation by TNF. Since ΔTRAF2 blocked the activation of p38 by $TNF_{70-80}$, the data not only demonstrate that TRAF2 was recruited to the TNF receptors and was required for the activation of p38 by $TNF_{70-80}$ but also imply that $TNF_{70-80}$ was unable to cause the coupling of TRAF2 to elements upstream of JNK. Thus, while TNF stimulated the autophosphorylation of ASK-1 in HEK293T cells, $TNF_{70-80}$ was without effect.

The situation is more complex in neutrophils. Firstly, TNF was not able to stimulate the activity of JNK in non-adherent neutrophils. Secondly, neutrophil lysates contained an anti-ASK-1 immunoreactive band that was of a lower molecular weight than the ASK-1 band in HEK293T cells. Thirdly, in adherent and non-adherent neutrophils, ASK-1 autophosphorylation was not enhanced by either TNF or $TNF_{70-80}$. However, TNF but not $TNF_{70-80}$ stimulated the activity of GCKR/GLK in neutrophils that had been adhered to plasma-coated surfaces. Although a number of other TNF-responsive STE20 kinases exists, it was unlikely that any of these, if expressed, was activated by TNF in non-adherent neutrophils since TNF was unable to stimulate the activity of JNK in such neutrophils. Thus, the inability of $TNF_{70-80}$ to couple TRAF2 to either ASK-1 and/or GCKR/GLK could be a major underlying reason for its intriguing selective biological action. Our data also demonstrate for the first time that TNF can stimulate the activities of GCKR/GLK and JNK activity in neutrophils that had been preadhered to plasma-coated dishes. The inability of TNF70-80 to couple TNF receptors to the ERK module may reflect a similar failure of the peptide to promote the coupling of TRAF2 to an upstream regulator of the ERK module.

The data in the present study raise a number of interesting issues on the coupling of TNF receptor-associated proteins such as TRAF2 to their downstream effectors. Thus, although TNF70-80-stimulated activation of p38 required TRAF2, this was not functionally coupled to ASK-1 or GCKR/GLK in cells stimulated with the peptide, despite that observations that ASK-1, GCKR, GCK, MEKK1 can directly bind to and are activated by TRAF2. Although ASK-1 has been reported to couple TRAF2 to both the p38 and JNK modules, our data clearly show that ASK-1 was dispensable for p38 activation by $TNF_{70-80}$ in both HEK293T cells and neutrophils. In adherent neutrophils, ASK-1 was also dispensable for the activation of JNK by TNF. Another issue is that it has previously been reported that activation of the NFκB pathway by TNF requires RIP. Since a number of recent studies have also shown that RIP-mediated activation of the NFκB pathway requires MEKK1 or MEKK3, which are upstream of JNK, it is surprising that JNK was not activated by $TNF_{70-80}$ but NFκB was. However, although RIP can interact directly with MEKK1 which couples the STE20 kinases to MKK4/MKK7, the immediate upstream regulators of JNK, and over expression of RIP per se activates the JNK module, TNF activation of JNK does not require RIP since gene deletion of RIP did not attenuate JNK activation by the cytokine. Thus our data support the suggestion that the TRAF2-GCKR-MEKK1 mechanism bypasses RIP in the activation of JNK by TNF.

In summary, we have characterised the $TNF_{70-80}$ induced signalling cascades and how it differs from the TNF-induced intracellular signalling. It is evident that $TNF_{70-80}$ activates the TRAF2→p38 and NFκB pathways but not the TRAF2→ASK-1/GCKR/GLK→JNK pathway or the TRAF2→ERK pathway. Thus for the first time, we demonstrate that it is possible to synthesize a cytokine mimetic which acts via the cytokine receptor but stimulates a restricted range of signalling pathways that, interestingly, is related to a restructured biological outcome compared to the parent cytokine. Our previous studies have revealed other TNF mimetic peptides which displayed direct tumor cell cytotoxicity but lacked neutrophil stimulating activity and TNF toxicity, presumably as a result of the activation of signalling molecules which are conducive for this action. Thus it is feasible to envisage that TNF mimetics can be generated which could independently produce one of the three major actions of TNF, immune enhancement, tumor killing and promotion of sepsis. Inevitably our finding opens new opportunities for the development of therapeutics which promote the beneficial effects of TNF, avoiding the toxic side effects associated with normal triggering of the TNF receptor. Above all, this study establishes a novel concept that appropriate small molecules can be used to selectively couple receptors to a restricted number of signalling pathways and this can be exploited to elicit a biological outcome of preference. Our data also suggest that mimetics such as $TNF_{70-80}$ may be a valuable tool to probe TNF receptor signalling.

Example 18

Figure 15:
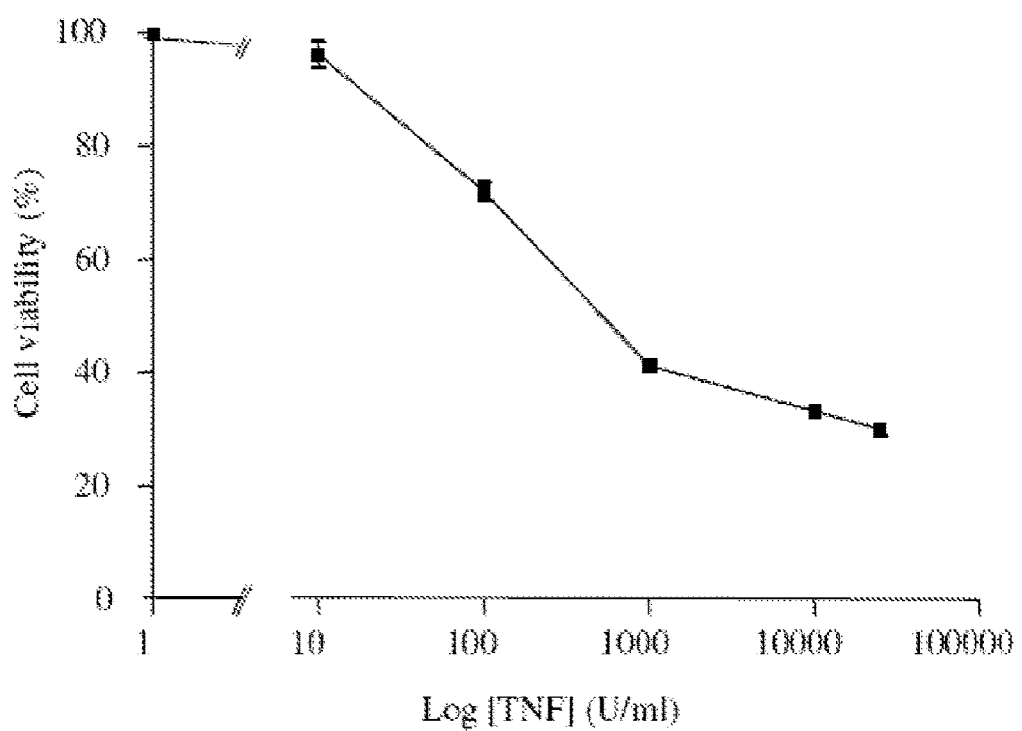
FIG. 15 shows in vitro cytotoxicity of TNF on WEHI-164 fibrosarcoma cells. A 100 µl of $5\times10^4$ cells/well were cultured in 96-well plates and pre-treated with actinomycin D (1 µg/ml) for 15 min before the addition of the different dilutions of TNF and incubated for 20 h. Afterwards 20 µl of 3-[4,5-dimethyl-thiazol-2-yl]-2,5-diphenyltetrazolium bromide dye (MTT) (5 mg/ml) was added and incubated for a further 4 h. The reaction was terminated by the addition of 50 µl of 20% SDS in 20 mM HCl and absorbance read at 540 nm after overnight incubation to solubilise the reduced MTT. Percentage viability was determined by comparison with untreated control cells. Results shown are means of triplicate determinations.
Figure 16:
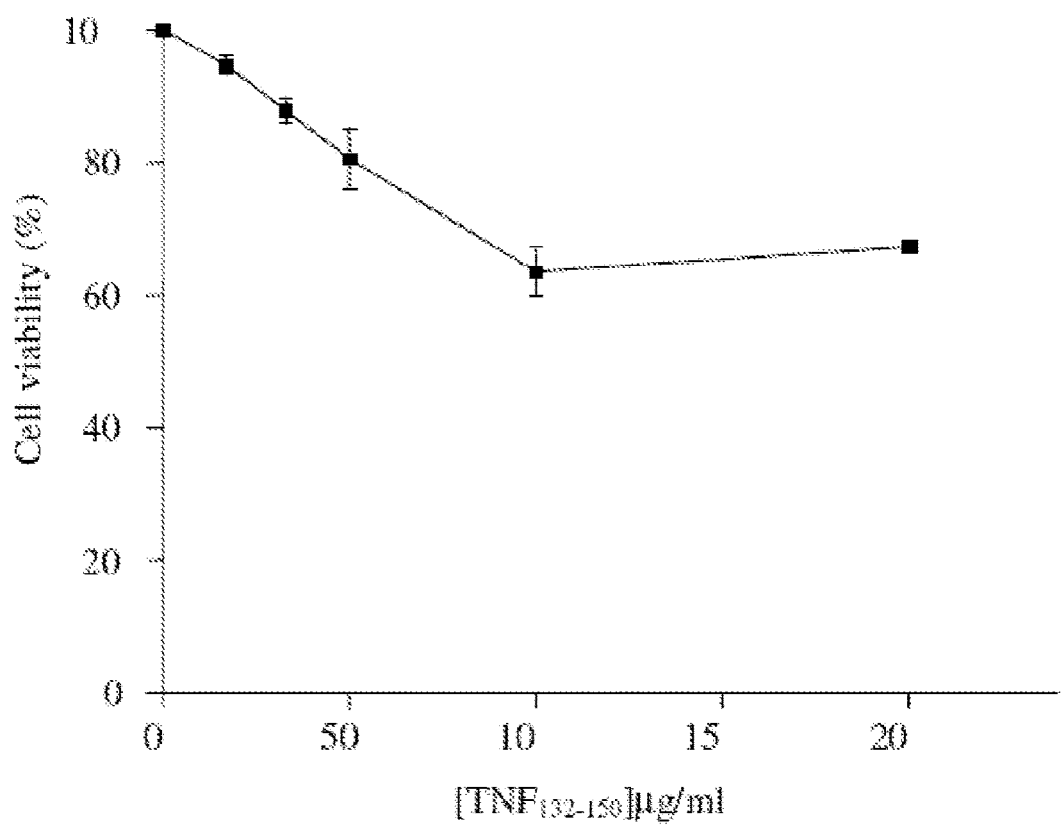
FIG. 16 shows in vitro cytotoxicity of peptide $TNF_{132-150}$ on WEHI-164 fibrosarcoma cells. A 100 µl of $5\times10^4$ cells/well were cultured in 96-well plates and pre-treated with actinomycin D (1 µg/ml) for 15 min before the addition of the different dilutions of $TNF_{132-150}$ and incubated for 20 h. Afterwards 20 µl of 3-[4,5-dimethyl-thiazol-2-yl]-2,5-diphenyltetrazolium bromide dye (MTT) (5 mg/ml) was added and incubated for a further 4 h. The reaction was terminated by the addition of 50 µl of 20% SDS in 20 mM HCl and absorbance read at 540 nm after overnight incubation to solubilise the reduced MTT. Percentage viability was determined by comparison with untreated control cells. Results shown are means of triplicate determinations.

The Effect of TNF and $TNF_{132-150}$ on Cell Survival in the Presence of Actinomycin D It has been previously reported that at low concentrations of TNF-α WEHI-164 cells undergo apoptosis, provided that the nuclear factor kappa B (NF-κB) dependent survival pathways are inhibited by the addition of the transcription inhibitor actinomycin D.
(i) Method The cell survival assay was performed using a modified method from Espevik and Nissen-Meyer (1986) *J Immunol Methods* 95(1):99-105 and O'Toole et al. (2001) *Biochem J.* 359:119-127. Briefly, WEHI-164 cells were grown in 96-well culture dishes to a density of $5 \times 10^4$ cells/well in growth medium with 1 mg/ml actinomycin D. After incubation with specific dilutions of TNF and $TNF_{132-150}$ for 20 h at 37° C. 5% $CO_2$, cells were washed once with PBS and incubated with 3-(4,5 dimethylthiazol-2-yl)-2,5-diphenyl-2H-tetrazolim bromide (MTT) solution (5 mg/ml in PBS; 20 μl/well) for a further 4 h. The reaction was terminated by the addition of 50 μl of 20% SDS in 20 mM HCl and absorbance read at 540 nm after overnight incubation to solubilise the reduced MTT.
(ii) Results The results obtained are shown in FIGS. 15 and 16. The peptide $TNF_{132-150}$ was able to elicit the same cytotoxic effects as that of TNF under the same conditions.

Example 19

The Effect of $TNF_{132-150}$ and TNF on WEHI-164 Map Kinase Activity

Using the optimum cytotoxic concentrations determined in Example 18, we then investigated the effect of this peptide in comparison with TNF on the activation of MAP kinases within this cell line.
(i) Method WEHI-164 cells were cultured in 28 $cm^2$ dishes to approx 80% confluence before the desired treatment. Cells were then treated with TNF or $TNF_{132-150}$ in serum-free medium. After washing twice with cold HBSS, cells were harvested by scraping and lysed in 400 µl of buffer A (20 mM HEPES, pH 7.4, 0.5% (v/v) Nonidet P-40, 100 mM NaCl, 1 mM EDTA, 2 mM $Na_3VO_4$, 2 mM dithiothreitol, 1 mM phenylmethylsulfonyl fluoride, and 10 µg/ml Sigma 104, leupeptin, aprotonin, pepstatin A, and benzamidine) for 2 h at 4° C. with constant mixing (Hii et al. (1998) *J Biol Chem.* 273(30):19277-82). After centrifugation (12,000 g×5 min), the supernatants were collected and the protein content of the lysates was determined by Lowry's method of protein determination. A solid phase assay using glutathione-S-transferase (GST)-conjugated-jun (1-79) was employed to assay JNK activity (Hii et al. (1998) *J Biol Chem.* 273(30):19277-82) GST-jun (1-79) was fractionated on 12% SDS polyacrylamide gels and the bands were detected and radioactivity determined using an Instant Imager (Packard Instruments, Canberra, Australia). For p38 and ERK1/ERK2 activity lysates containing equal amounts of protein (0.5-1 mg) were precleared with protein A sepharose (4° C.) before being incubated with anti-p38 or anti-ERK2 antibody (3 µg/sample). After mixing for 2 h (4° C.), the immune complexes were precipitated by the addition of protein A sepharose. The immunoprecipitates were collected by centrifugation (16,000 g×15s) and washed once with buffer A (4° C.), once with buffer B (10 mM Tris/HCl, pH 7.6, 100 mM NaCl, 1 mM EDTA and 2 mM $Na_3VO_4$ and once with assay buffer (Hii et al. (1998) *J Biol Chem.* 273 (30):19277-82). ERK and p38 activities were determined as described using myelin basic protein as a substrate (Hii et al. (1998) *J Biol Chem.* 273(30):19277-82). Myelin basic protein was fractionated on a 16% SDS polyacrylamide gel, and the bands were similarly detected using an Instant Imager (Packard Instruments, Canberra, Australia).

(ii) Results

Selective Activation of JNK and ERK1/ERK2 by $TNF_{132-150}$ not TNF

Figure 17:
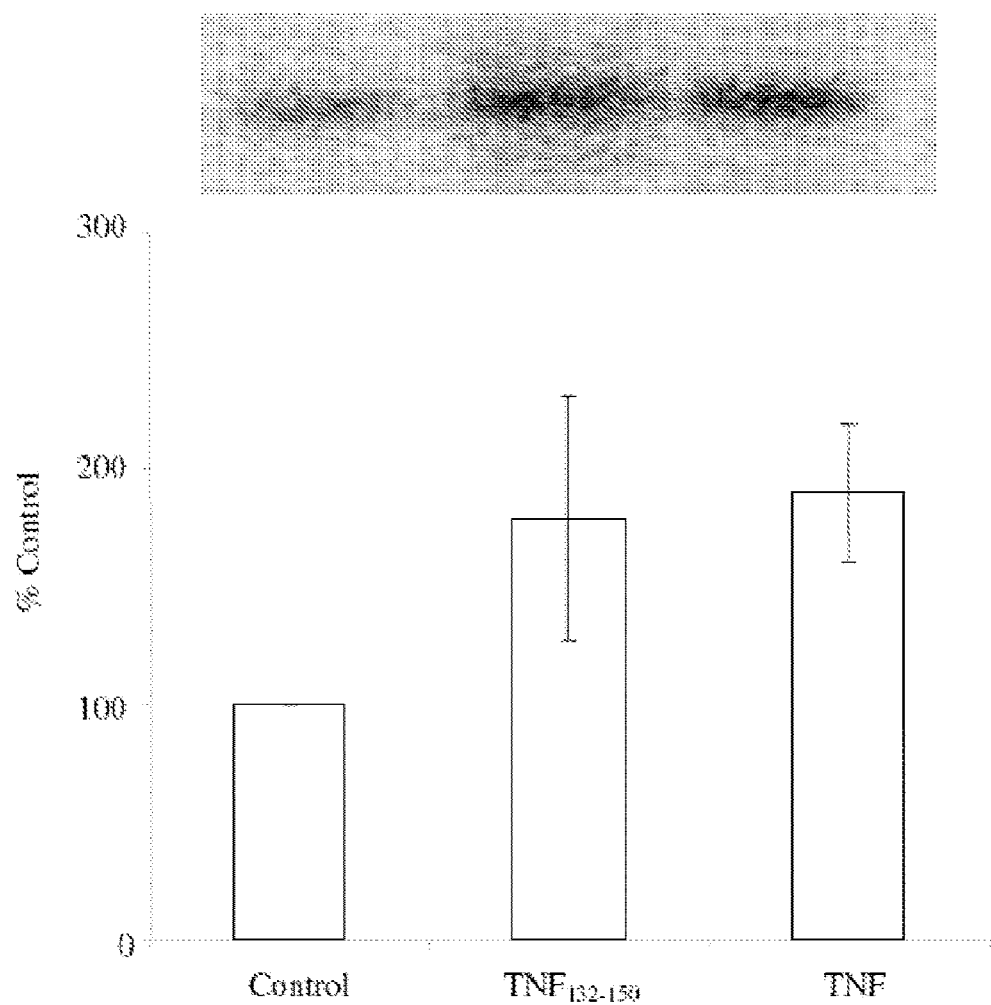
FIG. 17 shows that $TNF_{132-150}$ activates JNK activity similarly to TNF. To investigate the activation of JNK serum-starved WEHI-164 cells incubated with 1000 U/ml TNF or $TNF_{132-150}$ (100 g/ml) for 15 mins at 37° C., the cells were lysed and the degree of JNK activity was assayed using GST-jun (1-79) as a substrate. A representative radiogram from the Instant Imager and pooled data (means±SEM of 3 experiments) are shown.
Figure 18:
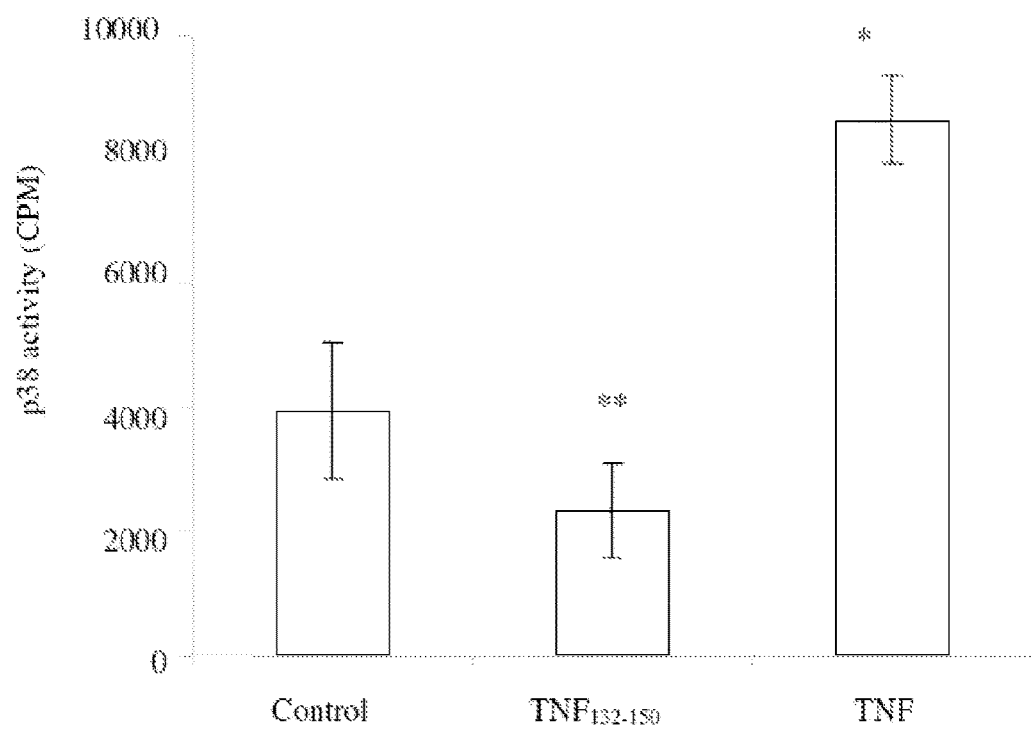
FIG. 18 shows that $TNF_{132-150}$ fails to activate p38 kinase activity. To assess the activation of p38 serum-starved WEHI-164 cells incubated with 1000 U/ml TNF or $TNF_{132-150}$ (100 µg/ml) for 15 mins at 37° C., the cells were lysed p38 immunoprecipitated and kinase activity was assayed using myelin basic protein as a substrate. The level of myelin basic protein phosphorylation was quantitated by an Instant Imager. A representative radiogram from the Instant Imager and pooled data (means±SEM of 3 experiments) are shown. Significance of difference between control and TNF or $TNF_{132-150}$: *p<0.05; **p<0.01.
Figure 19:
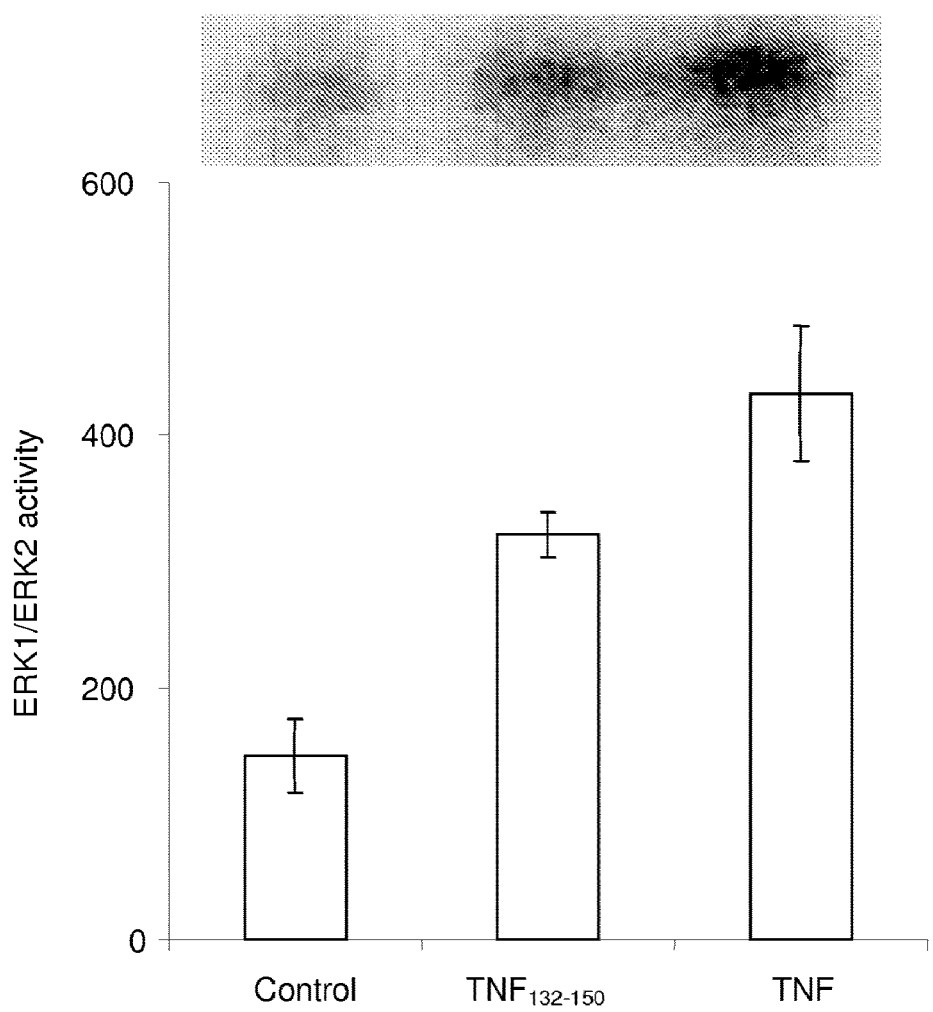
FIG. 19 shows that $TNF_{132-150}$ activates ERK1/ERK2 in manner similar to TNF. To assess the effects on ERK1/ERK2 activation, serum-starved WEHI-164 cells incubated in the presence or absence of TNF (1000 U/ml) or $TNF_{132-150}$ (100 µg/ml) for 15 mins at 37° C., the cells were lysed ERK1/ERK2 activation was determined by kinase activity using myelin basic protein as a substrate. The level of myelin basic protein phosphorylation was quantitated by an Instant Imager. A representative radiogram from the Instant Imager and pooled data (means±SEM of 3 experiments) are shown. Significance of difference between control and TNF or $TNF_{132-150}$: *p<0.05; **p<0.01.

While TNF was able to activate all three MAP kinases in adherent WEHI-64 cells, $TNF_{132-150}$ only enhanced the activity of JNK and ERK1/2 and not p38 at concentrations which we have shown to cause cytotoxicity in WEHI-164 cells following pre-treatment with actinomycin D. $TNF_{132-150}$ (100 µg/ml) was able to activate JNK kinase activity similar to that by TNF (1000 U/mL) (FIG. 17). The degree of ERK1/ERK2 activation between TNF and $TNF_{132-150}$ was slightly less in the latter (FIG. 19). An inability of $TNF_{132-150}$ to activate neutrophils has been previously demonstrated, therefore we examined if this could be due to the inability of $TNF_{132-150}$ to activate the p38 kinase. The activity of p38 was increased by TNF at a concentration of 1000 U/ml. Interestingly, $TNF_{132-150}$ failed to stimulate the activity of p38 in WEHI-164 cells (FIG. 18). This data correlates well, as we have also shown that $TNF_{132-150}$ is unable to stimulate neutrophil superoxide production, which is mediated by p38.

Example 20

The Effect of $TNF_{132-150}$ on Neutrophil Superoxide Production

Superoxide production by human neutrophils was measured by the reduction of the fluorescent lucigenin, (9,9'-bis (N-methyl-acridinium nitrate) (Sigma Chemical Company). This provides a direct and specific measure of agonist-induced superoxide production. Lucigenin-dependant chemiluminescence was measured as described previously Gyllenhannar H. (1987) *J. Immunol. Methods* 97:209-213. Briefly, 50 µl of 100 mg/ml of peptide or diluent and 250 ml of lucigenin was added to neutrophils ($5 \times 10^5$ in 50 µl HBSS).

The cells were placed in a water-jacketed luminometer chamber (37° C.) (Autolumat Plus Model LB 953, Berthold Technologies, Bundoora, Australia) and the resulting light output recorded in millivolts (mV) at 10 second intervals. The data was analysed with Multi-user software (Berthold Tubemaster, Bundoora, Australia).

Figure 20:
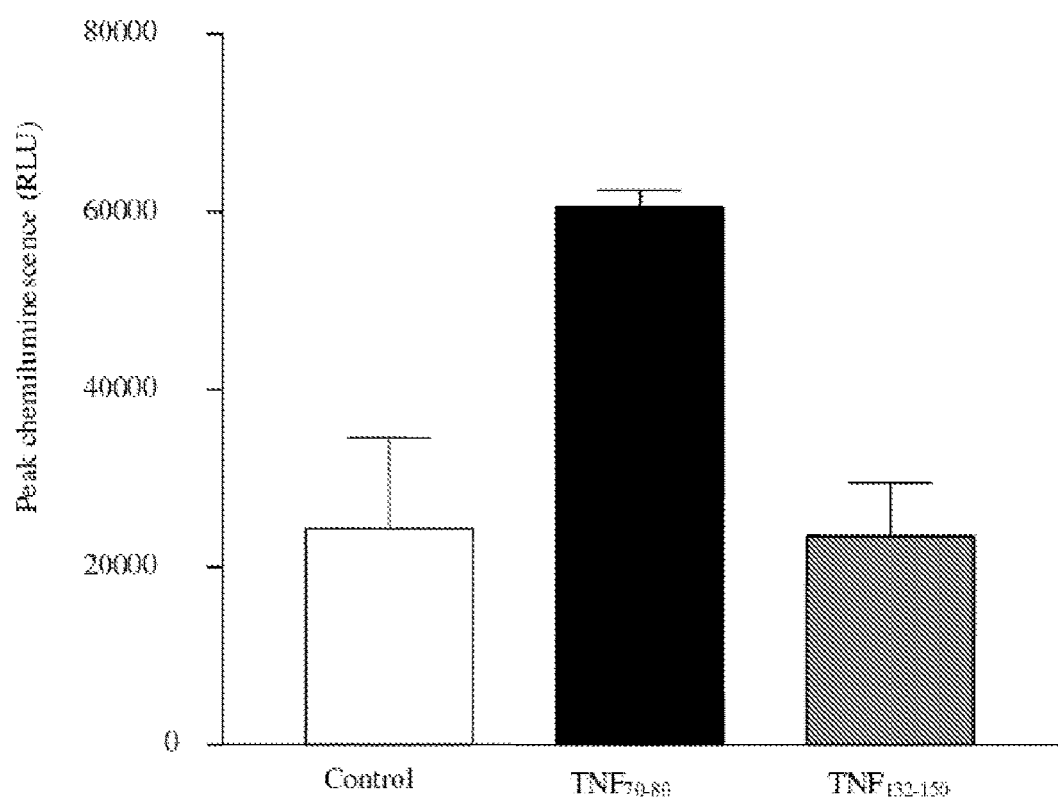
FIG. 20 shows the effect of peptides $TNF_{70-80}$ and $TNF_{132-150}$ on superoxide production in neutrophils. To 50 µl of neutrophils ($5\times10^5$ in HBSS), 501 of 100 µg/ml of peptide or diluent and 250 µl of lucigenin were added. The cells were placed in a water-jacketed luminometer chamber (37° C.) (Autolumat Plus Model LB 953, Berthold Technologies, Bundoora, Australia) and the resulting light output recorded in millivolts (mV) at 10 second intervals. The data was analysed with Multi-user software (Berthold Tubemaster, Bundoora, Australia). The results are expressed as peak superoxide produced. Significance of difference between control and $TNF_{70-80}$ or $TNF_{132-150}$: *p<0.05.

The results are expressed as peak superoxide produced unless specified otherwise, and are shown in FIG. 20. $TNF_{132-150}$ failed to stimulate superoxide production, consistent with its inability to activate p38 kinase.

Example 21

Figure 21:
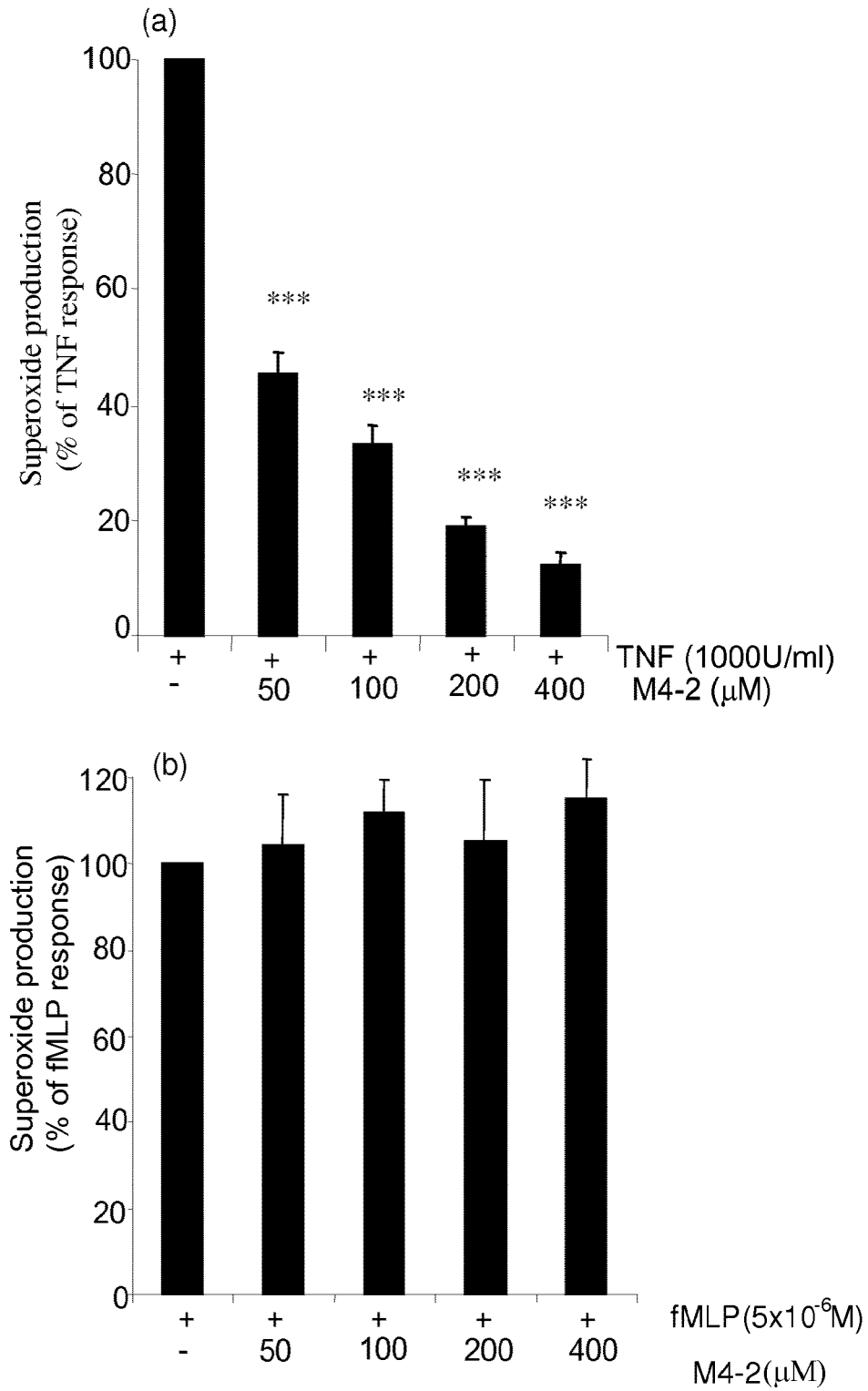
FIG. 21(a) and (b) show the effect of a TNFR1 fragment, H-Gly-Thr-Thr-OH, on TNF-induced superoxide generation of neutrophils (Panel A) and the effect of the peptide on the FMLP-induced chemiluminescence (Panel B).

Peptide H-Gly-Thr-Thr-OH Inhibits TNF-Induced Superoxide Generation by Neutrophils FIG. 21(a) shows the effects of TNFR1 fragment, H-Gly-Thr-Thr-OH (M4-2; SEQ ID NO.6), on TNF-induced superoxide generation of neutrophils. Different concentrations of the peptide was mixed with TNF at 37° C. for 20 min and then added to neutrophils and the resultant chemiluminescence measured in a luminometer. The inhibitory effect of the peptide is shown as a percentage of the maximal activity on TNF-induced superoxide generation in the absence of M4-2. Data are presented as mean±SEM of 3 experiments. Significance of difference: ***$p<0.001$, Tukey-Kramer multiple comparisons test.

FIG. 21(b) shows the effect of the peptide on the FMLP-induced chemiluminescence. Data are presented as % of fMLP-stimulated superoxide production (Mean±SEM of 3 experiments) in the absence of M4-2.

Example 22

Figure 22:
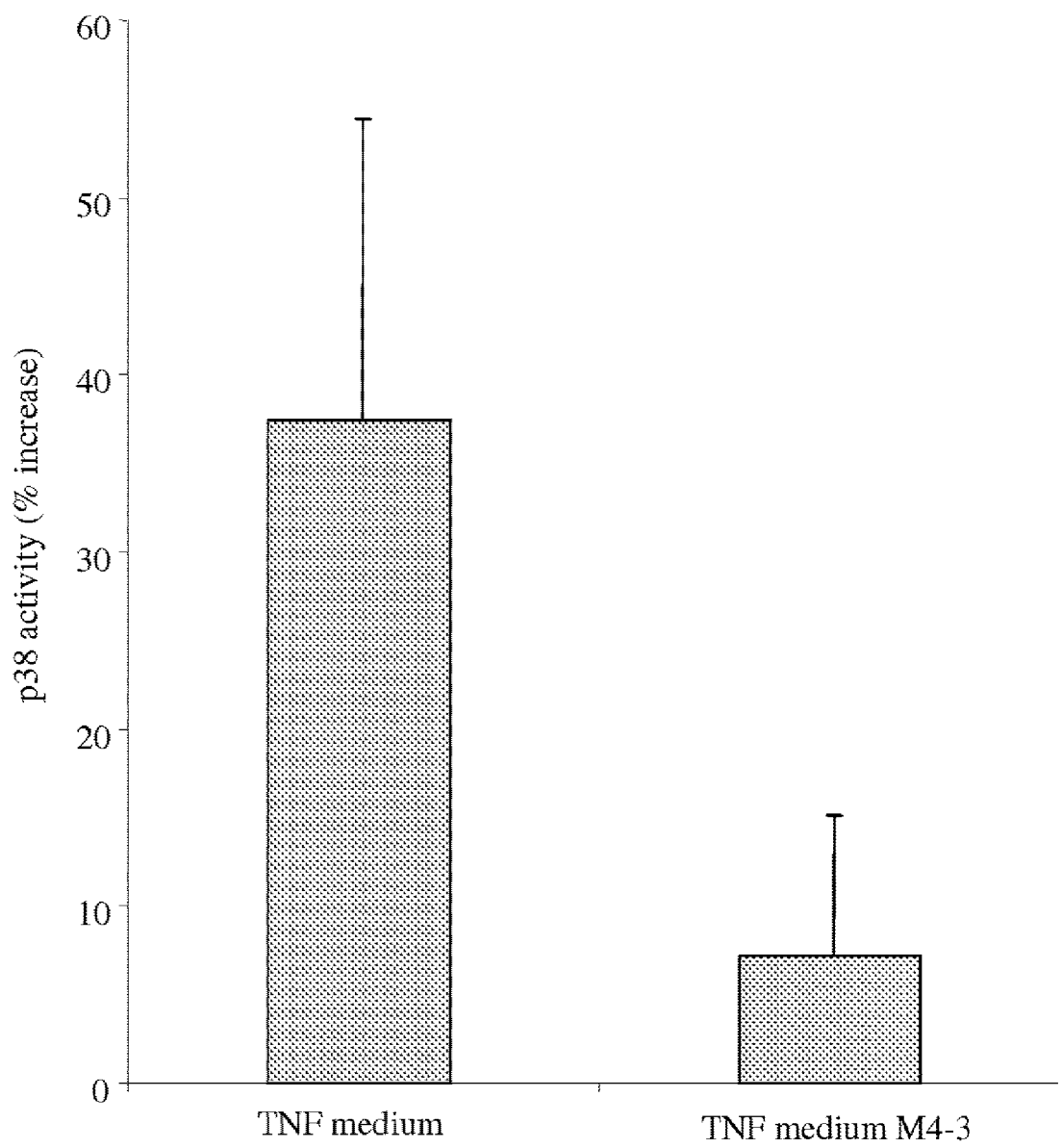
FIG. 22 shows the inhibition of TNF-induced p38 activation in human neutrophils by TNR1 peptide Glu-Asp-Ser-Gly-Thr-Thr (SEQ ID NO: 10).

Inhibition of TNF (Mononuclear Leukocyte Fluid)-Induced p38 Activation in Human Neutrophils by Peptide Glu-Asp-Ser-Gly-Thr-Thr FIG. 22 shows the inhibition of TNF (mononuclear leukocyte fluid)-induced p38 activation in human neutrophils by peptide Glu-Asp-Ser-Gly-Thr-Thr (M4-3; SEQ ID NO. 10). The peptide M4-3 was pre-incubated with TNF medium [1:10 dilution in HBSS≈0.12 ng/ml TNF] at 37° C. for 20 min in 5% CO2. Neutrophils ($1 \times 10^7$) were then added and further incubated for 30 min at 37° C. The cells were lysed, p38 immunoprecipitated and kinase activity was assayed using myelin basic protein as a substrate. The level of myelin basic protein phosphorylation was quantitated by an Instant Imager. The data is presented as % increases of p38 activity (mean±SEM of 2 experiments) are shown.

Example 22

Protein Binding Screen

As described in Example 17, certain peptides derived from the TNF receptor have the ability to inhibit the action of the $TNF_{70-80}$ peptide.

This data indicates generally that libraries of molecules may be tested to identify agents that interact with the TNF receptor, or that libraries of molecules may be used to identify agents that modulate the interaction of other molecules with the TNF receptor.

This example is directed to a method of testing libraries of molecules for the ability to prevent the binding of certain peptides to a TNF receptor, or the screening of molecules for the ability to displace the binding of certain peptides from the receptor. The use of a high throughput screen is contemplated for the screening of the libraries of the candidate molecules.

Part or all of the TNF receptor may be fixed to a solid substrate by a method known in the art and the ability of candidate molecules to inhibit the binding of Peptide A (Pro-Ser-Thr-His-Leu-Ile-Thr-His-Thr-Ile; SEQ ID NO.4) to the receptor, and/or the ability of small molecules to inhibit the binding of Peptide B (Leu-Ser-Ala-Glu-Ile-Asn-Arg-Pro-Asp-Tyr-Leu-Asp-Phe-Ala-Glu-Ser-Gly-Gln-Val; SEQ ID NO. 5) to the receptor may be determined.

The screen may be performed by a method known in the art. Methods for determining the binding of molecules to receptors are described in "Protein-Ligand Interactions" (2003) Wiley-VCH Verlag GmbH & Co edited by H-J. Bohm et al.

Molecules that have either or both of the abilities described above will then be tested in a cell-based screen to determine the ability of the small molecules to trigger one or more of the p38, JNK and ERK1/2 signalling pathways in cells with and without functional TNF receptor. Examples of suitable cell based screens are as previously described herein. This will identify molecules that are specific agonists and antagonists of p38, JNK or ERK1/2.

It will be appreciated that this methodology is also applicable to the screening for agonists and antagonists that module signalling by receptors generally.

Example 23

Anti-Inflammatory Properties of TNFR Peptides in a Model for Cystic Fibrosis

*Pseudomonas aeruginosa* (Pa) is the predominant bronchial pathogen in the majority of cystic fibrosis patients. We will use this bacteria to induce inflammation in mice under conditions which mimic the inflammatory response in CF. A chronic Pa lung infection will be established using bacteria encapsulated in agarose beads by modification of previously reported methods (Cash H A, Woods D E, McCullough, Johnson W G Jr, and Bass J A (1979) *Am. Rev. Respir. Dis.* 119: 453-459). This will be inoculated intratracheally, the lungs removed after 18 h, lung cells prepared and neutrophils quantitated.

In preliminary studies we have found that there is approximately a ten fold increase in neutrophil numbers in infected animals. In these experiments, mice will be injected with different doses of various peptide intravenously 1 h prior to bacterial inoculation and 8 h post infection. In a second set of experiments we will inoculate the peptide into the lungs 8 h after bacteria inoculation. A range of doses of the peptides will be tested.

The effect of local application of these peptides may also be studied. Mice will be treated with varying doses of peptides, according to the above schedules by using aerolization chambers).

The functional state of the neutrophils will also be examined. We have previously demonstrated that neutrophils from Pa infected mice show an eight fold increase in ODRS production. The cells will be examined for the chemiluminescence response. It is expected that peptides will inhibit the neutrophil influx into the lungs and that the cells harvested have reduced production of ODRS.

Methods: Pa lung infection will be established in swiss female specific pathogen free out bred mice using bacteria encapsulated agarose beads by a modification of a previous method (Cash H A, Woods D E, McCullough, Johnson W C Jr, and Bass J A (1979) *Am. Rev. Respir. Dis.* 119: 453-459). For inoculation into the lung, mice will be anaesthetized, the trachea excised, the bacterial preparation injected into the left bronchus and the midline incision sutured. After the experimental period of 18 h the lungs are collected, cut into pieces and digested with dispase. The total lung cells are then prepared through a series of filtration and differential centrifugations. The neutrophils enumerated by cell counts and differential examination of stained smears of the preparation. For functional assays neutrophils will be further purified by density centrifugation on percoll gradients. These will then be examined for chemiluminescence responses.

Finally, it will be appreciated that various modifications and variations of the described methods and compositions of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the art are intended to be within the scope of the present invention.

---

The invention claimed is:

1. A method of identifying an agent that selectively activates p38 and/or NFkB signaling and does not substantially activate signaling through one or more of the JNK and/or ERK1/2 signaling pathways controlled by TNF Receptor-1 (TNFR1), said method comprising identifying an agent that binds to one or more of amino acids 209 to 211 of SEQ. ID NO: 1, wherein an agent that binds to said amino acids is identified as an agent that selectively activates p38 and/or NFkB signaling.

2. A method according to claim 1, wherein the agent selectively activates p38 signaling and/or NFκB signaling upon binding of TNF-α to TNFR1.

3. A method of identifying an agent that selectively activates p38 and/or NFkB signaling downstream of TNF Receptor-1 (TNFR1), comprising:
   (i) providing an intact cell with TNFR1 on its surface;
   (ii) contacting said cell with an agent that binds to one or more of amino acids 209 to 211 of SEQ. ID NO: 1;
   (iii) assaying the activation of the p38 and/or NFkB;
   (iv) assaying the activation of JNK or ERK1/2; and (v) selecting the agent that activates p38 and/or NFkB signaling pathway and does not substantially activate the JNK and/or ERK1/2 signaling pathway.

* * * * *

UNITED STATES PATENT AND TRADEMARK OFFICE
CERTIFICATE OF CORRECTION

PATENT NO. : 8,268,635 B2  
APPLICATION NO. : 12/301429  
DATED : September 18, 2012  
INVENTOR(S) : Ferrante et al.

Page 1 of 1

It is certified that error appears in the above-identified patent and that said Letters Patent is hereby corrected as shown below:

Title Page, Item (54) and Col. 1, Title: Delete "NKKB" and insert -- NFκB --

Signed and Sealed this
Fifth Day of February, 2013

Teresa Stanek Rea
*Acting Director of the United States Patent and Trademark Office*